United States Patent
Midwood et al.

(10) Patent No.: US 10,088,479 B2
(45) Date of Patent: Oct. 2, 2018

(54) BIOMARKER AND USES THEREOF

(71) Applicant: ISIS INNOVATION LIMITED, Summertown, Oxfordshire (GB)

(72) Inventors: Kim Suzanne Midwood, Headington (GB); Patrick John Venables, Headington (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 0 days.

(21) Appl. No.: 15/109,775

(22) PCT Filed: Jan. 13, 2015

(86) PCT No.: PCT/GB2015/050052
§ 371 (c)(1),
(2) Date: Jul. 5, 2016

(87) PCT Pub. No.: WO2015/104563
PCT Pub. Date: Jul. 16, 2015

(65) Prior Publication Data
US 2016/0327556 A1    Nov. 10, 2016

(30) Foreign Application Priority Data

Jan. 13, 2014 (GB) .................. 1400521.9

(51) Int. Cl.
*G01N 33/53* (2006.01)
*G01N 33/564* (2006.01)
*G01N 33/68* (2006.01)

(52) U.S. Cl.
CPC ....... *G01N 33/564* (2013.01); *G01N 33/6893* (2013.01); *G01N 2333/705* (2013.01); *G01N 2440/18* (2013.01); *G01N 2800/102* (2013.01); *G01N 2800/52* (2013.01)

(58) Field of Classification Search
None
See application file for complete search history.

(56) References Cited

FOREIGN PATENT DOCUMENTS

JP    2004138489 A    5/2004
WO    2013088140 A2   6/2013

OTHER PUBLICATIONS

Toshimichi et al. (JP 2004138489) English Translation.*
Dune' et al. (J. Int. Med. 2009 vol. 265, p. 593-603).*
International Search Report and Written Opinion for corresponding PCT/GB2015/050052, dated Apr. 2, 2015 (12 pages).
Chiquet-Ehrismann et al., 2003, "Tenascins: regulation and putative functions during pathological stress," Journal of Pathology, vol. 200, pp. 488-499.
Gulcher et al., 1991, "Structure of the human hexabrachion (tenascin) gene," Proc. Natl. Acad. Sci. USA, vol. 88, pp. 9438-9442.
Wegner et al, 2010, "Autoimmunity to specific citrullinated proteins gives the first clues to the etiology of rheumatoid arthritis," Immunological Reviews, vol. 233, pp. 34-54.

* cited by examiner

*Primary Examiner* — Changhwa J Cheu
(74) *Attorney, Agent, or Firm* — Melissa Hunter-Ensor; Leslie Serunian; Greenberg Traurig, LLP

(57) ABSTRACT

The invention relates to a method of determining the inflammatory disorder status of a subject comprising detecting the presence or absence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample from said subject.

27 Claims, 44 Drawing Sheets
Specification includes a Sequence Listing.

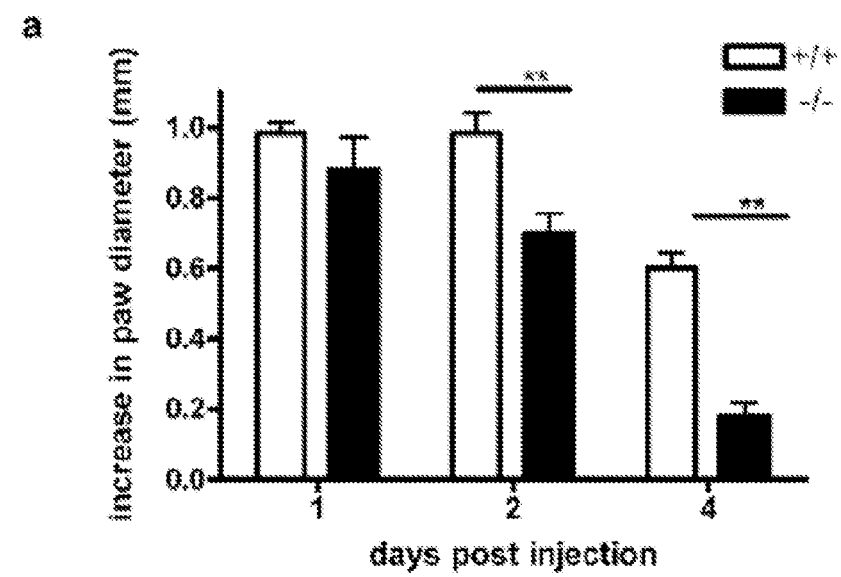
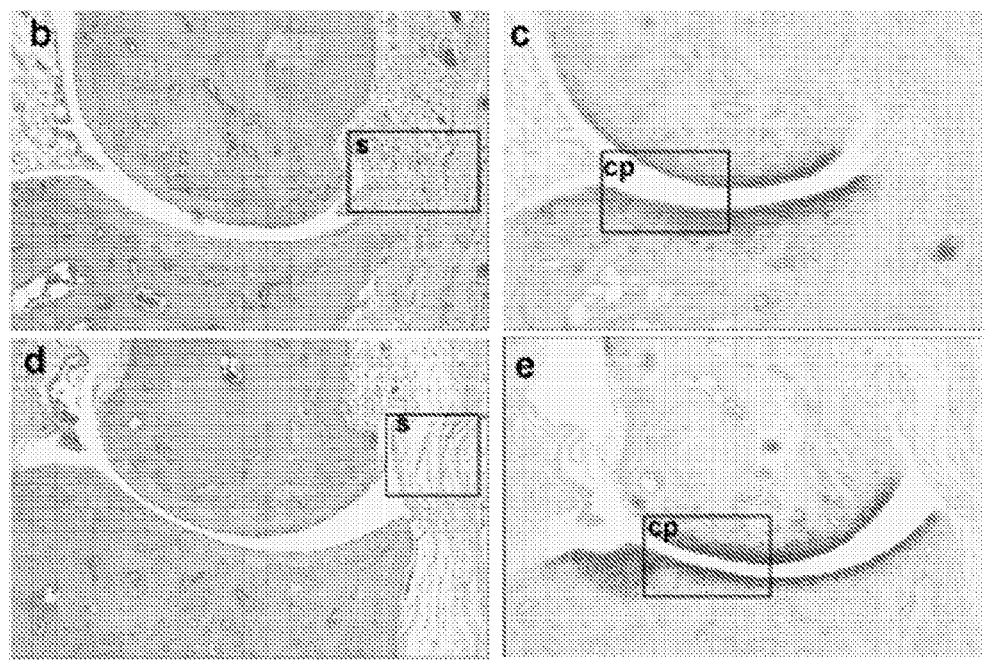
Figure 1

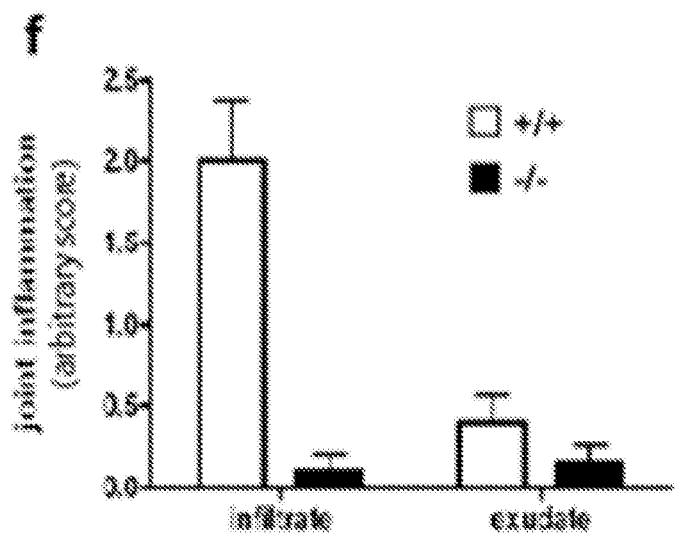
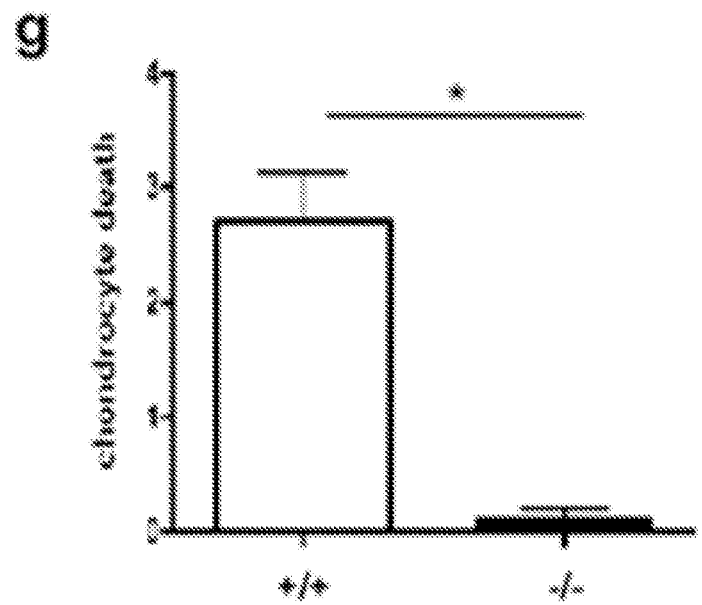
*Figure 1 (con't)*

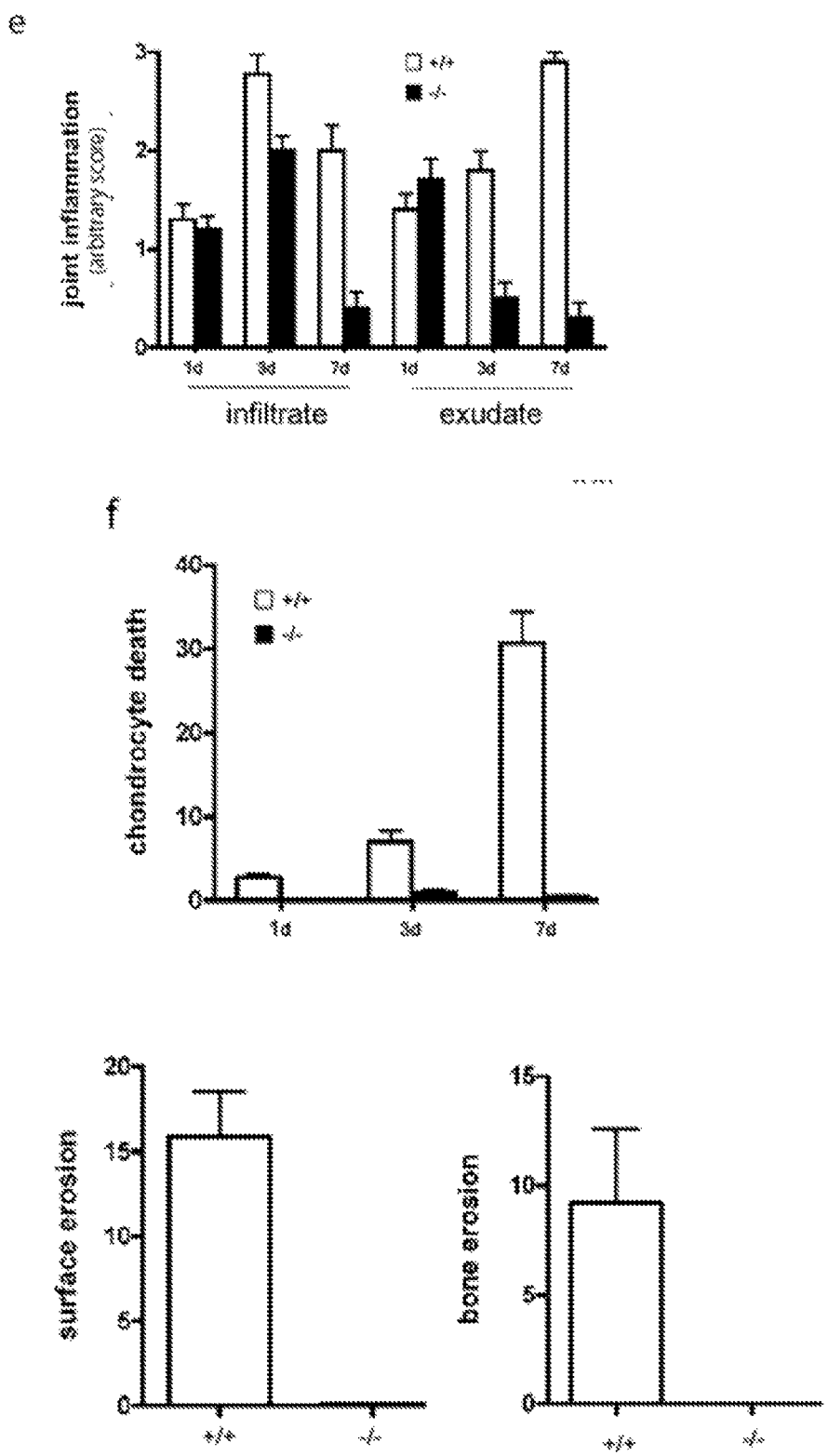
Figure 4 (con't)

a
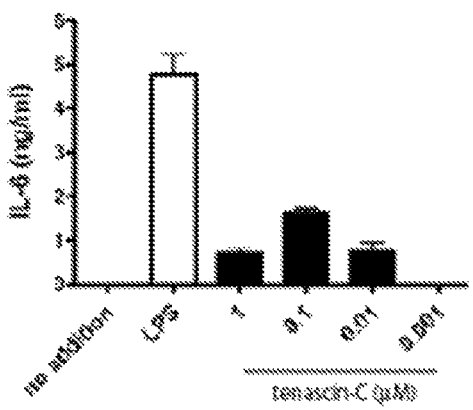
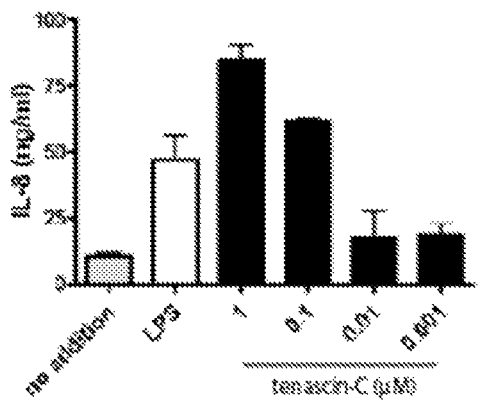
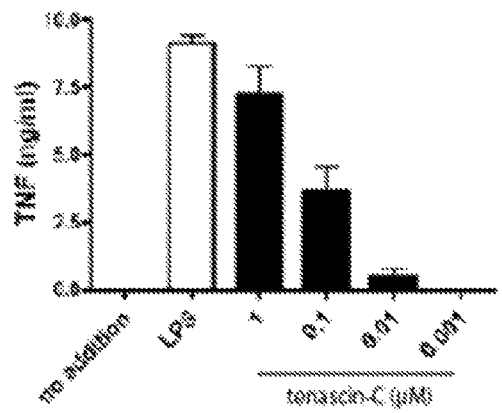
*Figure 5*

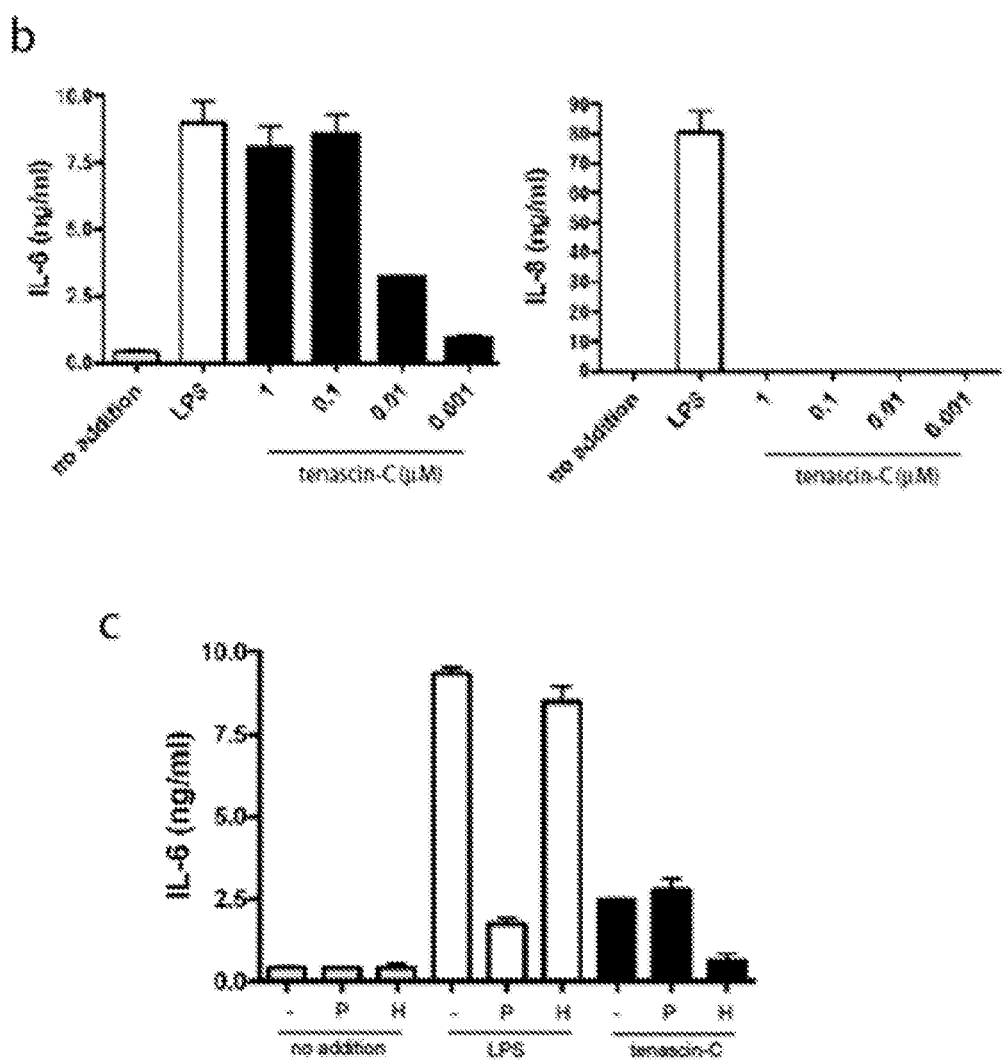
*Figure 5 (con't)*

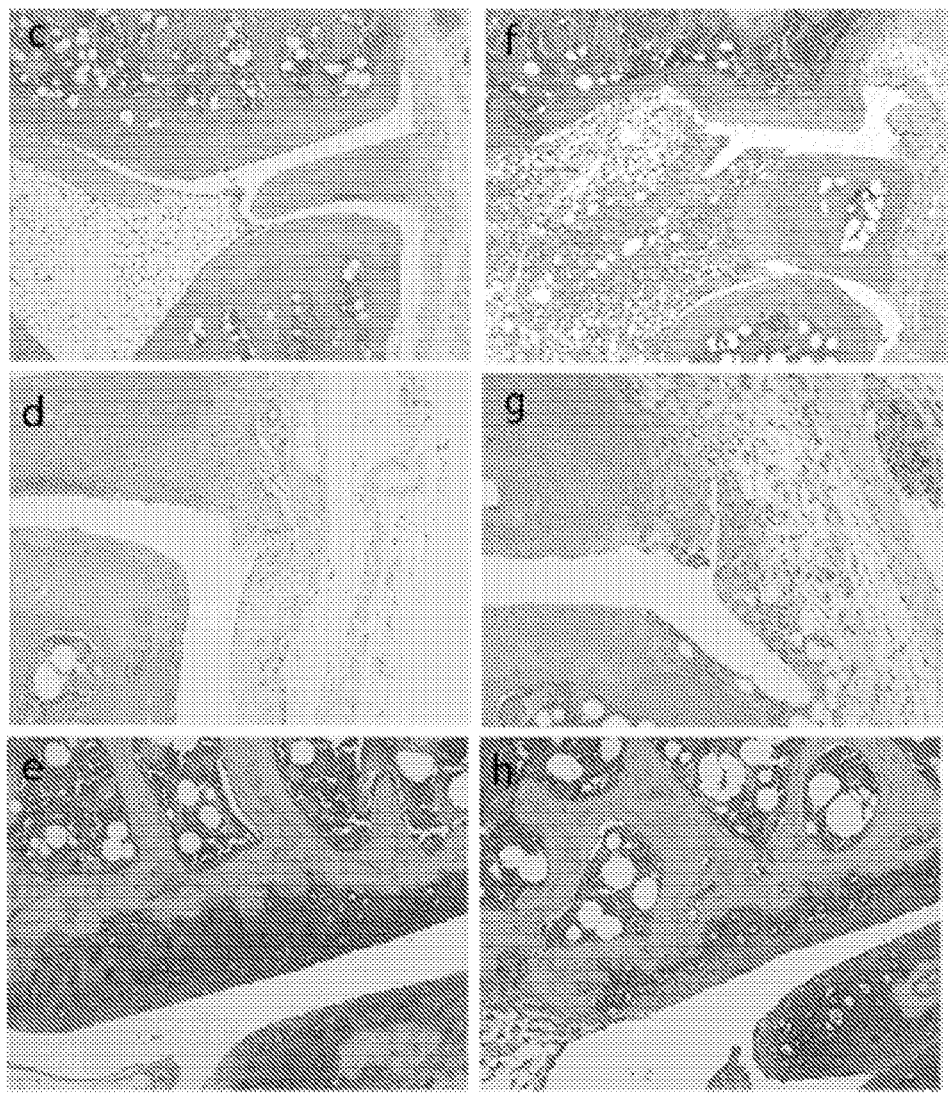
*Figure 6 (con't)*

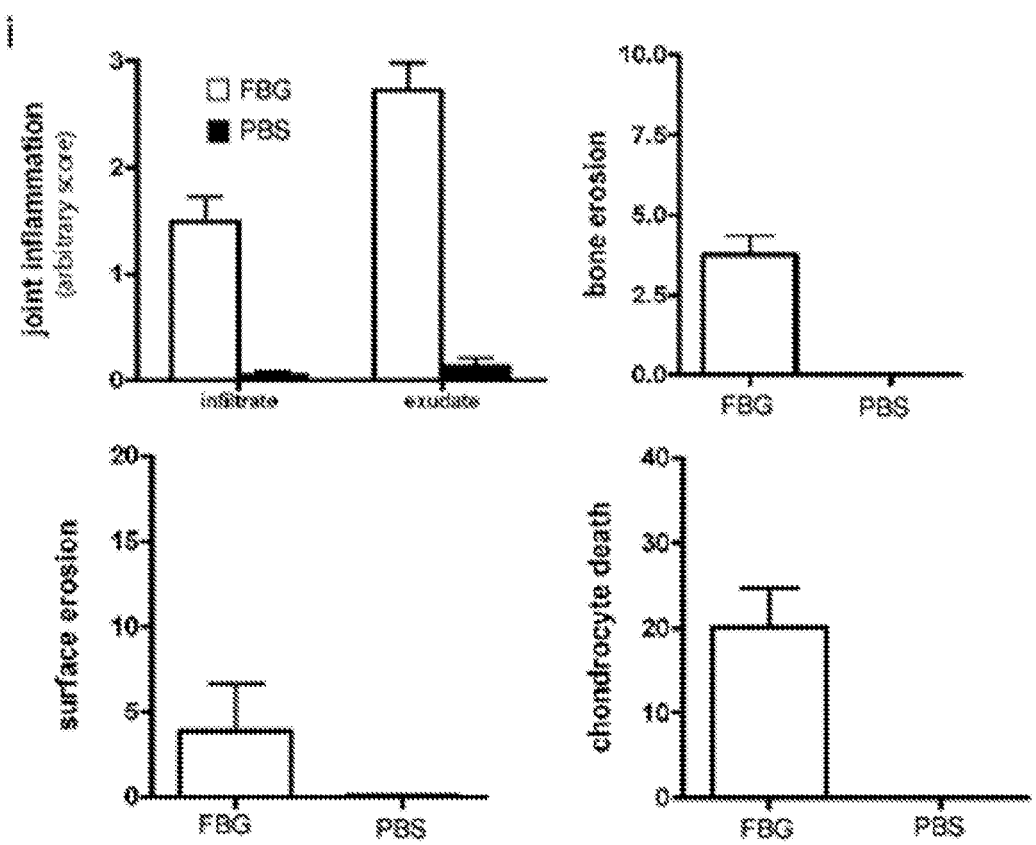
*Figure 6 (con't)*

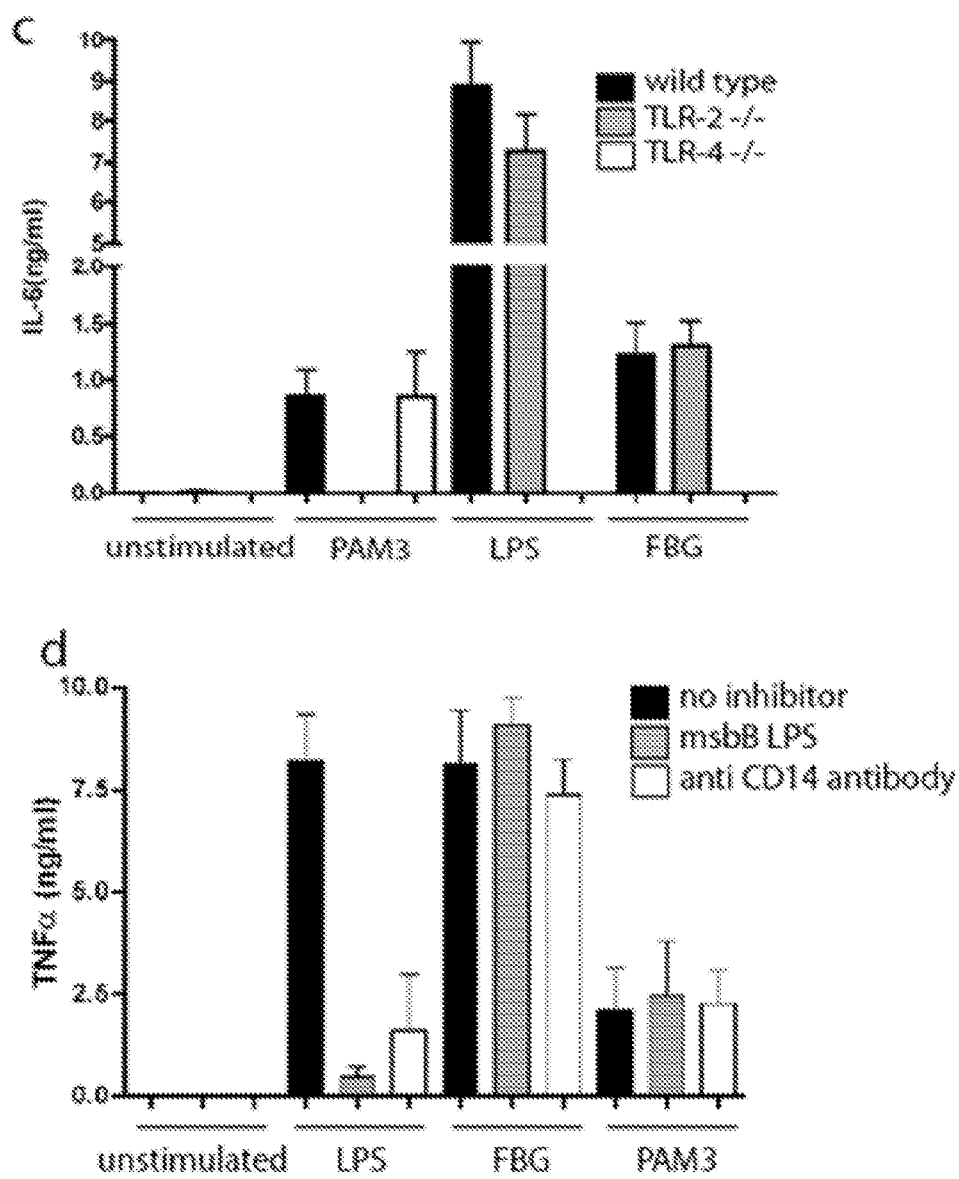
Figure 8 (con't)

TA domain [SEQ ID NO: 65]

```
 23 gvlkkvir hkrqsgvnat lpeen  45
```

EGFL domain [SEQ ID NO: 66]

```
146                              cclqp atgrldtrpf csgrgnfste gcgcvcepgw
181 kgpncsepec pgnchlrgrc idgqcicddg ftgedcsqla cpsdcndqgk cvngvcicfe
241 gyagadcsre icpvpcseeh gtcvdglcvc hdgfagddcn kplclnncyn rgrcvenecv
301 cdegftgedc selicpndcf drgrcingtc yceegftged cgkptcphac htqgrceegq
361 cvcdegfagl dcsekrcpad chnrgrcvdg rcecddgftg adcgelkcpn gcsghgrcvn
421 gqcvcdegyt gedcsqlrcp ndchsrgrcv egkcvceqgf kgydcsdmsc pndchqhgrc
481 vngmcvcddg ytgedcrdrq cprdcsnrgl cvdgqcvced gftgpdcael scpndchgqg
541 rcvngqcvch egfmgkdcke qrcpsdchgq grcvdgqcic hegftgldcg qhscpsdcnn
601 lgqcvsgrci cnegysgedc s     621
```

FNIII domain [SEQ ID NO: 67]

```
622                        evsppkdlv vtevteetvn lawdnemrvt eylvvytpth
661 egglemqfrv pgdqtstiiq elepgveyfi rvfailenkk sipvsarvat ylpapeglkf
721 ksiketsvev ewdpldiafe tweiifrnmn kedegeitks lrrpetsyrc tglapgqeye
781 islhivknnt rgpglkrvtt trldapsqie vkdvtdttal itwfkplaei dgieltygik
841 dvpgdrttic ltedenqysi gnlkpdteye vslisrrgdm ssnpaketft tgldaprnlr
901 rvsqtdnsit lewrngkaai dsyrikyapi sggdhaevdv pksqqattkt tltglrpgte
961 ygigvsavke dkesnpatin aateldtpkd lqvsetaets ltllwktpla kfdryrlnys
1021 lptgqwvgvc lprnttsyvl rglepgqeyn vlltaekgrh kskparvkas teqapelenl
1081 tvtevgwdgl rlnwtaadqa yehfiiqvqe ankveaarnl tvpgslravc ipglkaatpy
1141 tvsiygviqg yrtpvlsaea stgetpnlge vvvaevgwda lklnwtapeg ayeyffiqvq
1201 eadtveaaqn ltvpgglrst dlpglkaath ytitirgvtq dfsttplsve vlteevpdmg
1261 nltvtevswc alrlnwttpd gtydqftiqv qeadqveeah nltvpgslrs meipglragt
1321 pytvtlhgev rghstrplav evvtedlpql gdlavsevgw dglrlnwtaa dnayehfviq
1381 vqevnkveaa qnltlpgslr avdipgleaa tpyrvsiygv irgyrtpvls aeastakepe
1441 ignlnvsdit pesfnlswma tdgifetfti eiidsnrlle tveynisgae rtahisglpp
1501 stdfivylsg lapsirtkti satattealp llenltisdi npygftvswm asenafdsfl
1561 vtvvdsgkll dpqeftlsgt qrklelrgli tgigyevmvs gftqghqtkp lraeivteae
1621 pevdnllvsc atpdgfrlsw tadegvfdnf vlkirdtkkq sepleitlla pertrdltgl
1681 reateyeiel ygiskgrrsq tvsaiattam gspkevifsd itensatvsw raptaqvesf
1741 rityvpitgg tpsmvtvdgt ktqtrlvkli pgveylvsii amkgfeesep vsgsfttald
1801 gpsglvtani tdsealarwq paiatvdsyv isytgekvpe itrtvsgntv eyaltdlepa
1861 teytlrifae kgpqksstit akfttdldsp rdltatevqs etalltwrpp rasvtgyllv
1921 yesvdgtvke vivgpdttsy sladlspsth ytakiqalng plrsnmiqti ftt   1973
```

FBG domain [SEQ ID NO: 68]

```
1974                                                         igllypf
1981 pkdcsqamln gdttsglyti ylngdkaqal evfcdmtsdg ggwivflrrk ngrenfyqnw
2041 kayaagfgdr reefwlgldn lnkitaqgqy elrvdlrdhg etafavydkf svgdaktryk
2101 lkvegysgta gdsmayhngr sfstfdkdtd saitncalsy kgafwyrnch rvnlmgrygd
2161 nnhsqgvnwf hwkghehsiq faemklrpsn frnlegrrkr a    2201
```

*Figure 13*

[SEQ ID NO: 69]

```
   1 attacagagg aaggagctcg ctatataagc cagccaaagt tggctgcacc ggccacagcc
  61 tgcctactgt cacccgcctc tcccgcgcgc agatacacgc cccgcctcc gtgggcacaa
 121 aggcagcgct gctggggaac tcggggaac gcgcacgtgg aaccgccgc agctccacac
 181 tccaggtact tcttccaagg acctaggtct ctcgcccatc ggaaagaaaa taattcttc
 241 aagaagatca gggacaactg atttgaagtc tactctgtgc ttctaaatcc ccaattctgc
 301 tgaaagtgag atacccctaga gccctagagc cccagcagca cccagccaaa cccacctcca
 361 ccatggggc catgactcag ctgttggcag gtgtctttct tgctttcctt gccctcgcta
 421 ccgaaggtgg ggtcctcaag aaagtcatcc ggcacaagcg acagagtggg gtgaacgcca
 481 ccctgccaga agagaaccag ccagtggtgt ttaaccacgt ttacaacatc aagctgccag
 541 tgggatccca gtgttcggtg gatctggagt cagccagtgg ggagaaagac ctggcaccgc
 601 cttcagagcc cagcgaaagc ttcaggagc acacagtgga tggggaaaac cagattgtct
 661 tcacacatcg catcaacatc ccccgccggg cctgtggctg tgccgcagcc cctgatgtta
 721 aggagctgct gagcagactg gaggagctgg agaacctggt gtcttccctg agggagcaat
 781 gtactgcagg agcaggctgc tgtctccagc ctgccacagg ccgcttggac accaggccct
 841 tctgtagcgg tcggggcaac ttcagcactg aaggatgtgg ctgtgtctgc gaacctggct
 901 ggaaaggccc caactgctct gagcccgaat gtccaggcaa ctgtcacctt cgaggccggt
 961 gcattgatgg gcagtgcatc tgtgacgacg gcttcacggg cgaggactgc agccagctgg
1021 cttgccccag cgactgcaat gaccagggca agtgcgtaaa tggagtctgc atctgtttcg
1081 aaggctacgc cggggctgac tgcagccgtg aaatctgccc agtgccctgc agtgaggagc
1141 acggcacatg tgtagatggc tgtgtgtgt gccacgatgg ctttgcaggc gatgactgca
1201 acaagcctct gtgtctcaac aattgctaca accgtggacg atgcgtggag aatgagtgcg
1261 tgtgtgatga gggtttcacg ggcgaagact gcagtgagct catctgcccc aatgactgct
1321 tcgaccgggg ccgctgcatc aatggcacct gctactgcga agaaggcttc acaggtgaag
1381 actgcgggaa acccacctgc ccacatgcct gccacaccca gggccggtgt gaggaggggc
1441 agtgtgtatg tgatgaggc tttgccggtg tggactgcag cgagaagagg tgtcctgctg
1501 actgtcacaa tcgtggccgc tgtgtagacg ggcggtgtga gtgtgatgat ggtttcactg
1561 gagctgactg tgggagctc aagtgtccca atggctgcag tggccatggc cgctgtgtca
1621 atgggcagtg tgtgtgtgat gagggctata ctggggagga ctgcagccag ctacggtgcc
1681 ccaatgactg tcacagtcgg ggccgctgtg tcgagggcaa atgtgtatgt gagcaaggct
1741 tcaagggcta tgactgcagt gacatgagct gccctaatga ctgtcaccag cacggccgct
1801 gtgtgaatgg catgtgtgtt tgtgatgacg gctacacagg ggaagactgc cgggatcgcc
1861 aatgccccag ggactgcagc aacaggggcc tctgtgtgga cggacagtgc gtctgtgagg
1921 acggcttcac cggcccgac tgtgcagaac tctcctgtcc aaatgactgc catggccagg
1981 gtcgctgtgt gaatgggcag tgcgtgtgcc atgaaggatt tatgggcaaa gactgcaagg
2041 agcaaagatg tccccagtgac tgtcatggcc agggccgctg cgtggacggc cagtgcatct
2101 gccacgaggg cttcacagcc ctggactgtg gccacactc ctgccccagt gactgcaaca
2161 cttaggaca atgcgtctcg ggccgctgca tctgcaacag gggctacagc ggagaagact
2221 gctcagaggt gtctcctccc aaagacctcg ttgtgacaga agtgacggaa gagacggtca
2281 accggcctg ggacaatgag atgcgggtca cagagtacct tgtcgtgtac acgcccaccc
2341 acgagggtgg tctggaaatg cagttccgtg tgcctgggga ccagacgtcc accatcatcc
2401 aggagctgga gcctggtgtg gagtacttta tccgtgtatt tgccatcctg gagaacaaga
2461 agagcattcc tgtcagcgcc agggtggcca cgtacttacc tgcacctgaa ggcctgaaat
2521 tcaagtccat caaggagaca tctgtggaag tggagtggga tcctctagac attgcttttg
2581 aaacctggga gatcatcttc cggaatatga ataagaaga tgagggagag atcaccaaaa
2641 gcctgaggag gccagagacc tcttaccggc aaactggtct agctcctggg caagagtatg
2701 agatatctct gcacatagtg aaaaacaata cccggggccc tggcctgaag agggtgacca
2761 ccacacgctt ggatgccccc agccagatcc aggtgaaaga tgtcacagac accactgcct
2821 tgatcacctg gttcaagccc ctggctgaga tcgatggcat tgagctgacc tacggcatca
2881 aagacgtgcc aggagaccgt accaccatcg atctcacaga ggacgagaac cagtactcca
2941 tcgggaacct gaagcctgac actgagtacg aggtgtccct catctcccgc agaggtgaca
3001 tgtcaagcaa cccagccaaa gagaccttca caacaggcct cgatgctccc aggaatctc
```

*Figure 14*

```
3061 gacgtgtttc ccagacagat aacagcatca ccctggaatg gaggaatggc aaggcagcta
3121 ttgacagtta cagaattaag tatgccccca tctctggagg ggaccacgct gaggttgatg
3181 ttccaaagag ccaacaagcc acaaccaaaa ccacactcac aggtctgagg ccgggaactg
3241 aatatgggat tggagtttct gctgtgaagg aagacaagga gagcaatcca gcgaccatca
3301 acgcagccac agagttggac acgcccaagg accttcaggt ttctgaaact gcagagacca
3361 gcctgaccct gctctggaag acaccgttgg ccaaatttga ccgctaccgc ctcaattaca
3421 gtctccccac aggccagtgg gtgggagtgc agcttccaag aaacaccact tcctatgtcc
3481 tgagaggcct ggaaccagga caggagtaca atgtcctcct gacagccgag aaaggcagac
3541 acaagagcaa gcccgcacgt gtgaaggcat ccactgaaca agccctgag ctggaaaacc
3601 tcaccgtgac tgaggttggc tgggatggcc tcagactcaa ctggaccgca gctgaccagg
3661 cctatgagca ctttatcatt caggtgcagg aggccaacaa ggtggaggca gctcggaacc
3721 tcaccgtgcc tggcagcctt cgggctgtgg acataccggg cctcaaggct gctacgcctt
3781 atacagtctc catctatggg gtgatccagg gctatagaac accagtgctc tctgctgagg
3841 cctccacagg ggaaactccc aatttgggag aggtcgtggt ggccgaggtg ggctgggatg
3901 ccctcaaact caactggact gctccagaag gggcctatga gtactttttc attcaggtgc
3961 aggaggctga cacagtagag gcagcccaga acctcaccgt cccaggagga ctgaggtcca
4021 cagacctgcc tgggctcaaa gcagccactc attataccat caccatccgc ggggtcactc
4081 aggacttcag cacaaccccct ctctctgttg aagtcttgac agaggaggtt ccagatatgg
4141 gaaacctcac agtgaccgag gttagctggg atgctctcag actgaactgg accacgccag
4201 atggaaccta tgaccagttt actattcagg tccaggaggc tgaccaggtg gaagaggctc
4261 acaatctcac ggttcctggc agcctgcgtt ccatggaaat cccaggcctc agggctggca
4321 ctccttacac agtcaccctg cacggcgagg tcaggggcca cagcactcga cccttgctg
4381 tagaggtcgt cacagaggat ctcccacagc tgggagattt agccgtgtct gaggttggct
4441 gggatggcct cagactcaac tggaccgcag ctgacaatgc ctatgagcac tttgtcattc
4501 aggtgcagga ggtcaacaaa gtggaggcag cccagaacct cacgttgcct ggcagcctca
4561 gggctgtgga catcccgggc ctcgaggctg ccacgcctta tagtctcc atctatgggg
4621 tgatccgggg ctatagaaca ccagtactct ctgctgaggc ctccacagcc aaagaacctg
4681 aaattggaaa cttaaatgtt tctgacataa ctcccgagag cttcaatctc tcctggatgg
4741 ctaccgatgg gatcttcgag acctttacca ttgaaattat tgattccaat aggttgctgg
4801 agactgtgga atataatatc tctggtgctg aacgaactgc ccatatctca gggctacccc
4861 ctagtactga ttttattgtc tacctctctg gacttgctcc cagcatccgg accaaaacca
4921 tcagtgccac agccacgaca gaggccctgc cccttctgga aaacctaacc atttccgaca
4981 ttaatcccta cgggttcaca gtttcctgga tggcatcgga gaatgccttt gacagctttc
5041 tagtaacggt ggtggattct gggaagctgc tggaccccca ggaattcaca ctttcaggaa
5101 cccagaggaa gctggagctt agaggcctca taactggcat tggctatgag gttatggtct
5161 ctggcttcac ccaagggcat caaaccaagc ccttgagggc tgagattgtt acagaagccg
5221 aaccggaagt tgacaacctt ctggtttcag atgccacccc agacggtttc cgtctgtcct
5281 ggacagctga tgaagggtc ttcgacaatt ttgttctcaa aatcagagat accaaaaagc
5341 agtctgagcc actggaaata accctacttg cccccgaacg taccagggac ataacaggtc
5401 tcagagaggc tactgaatac gaaattgaac tctatggaat aagcaaagga aggcgatccc
5461 agacagtcag tgctatagca acaacagcca tgggctcccc aaaggaagtc attttctcag
5521 acatcactga aaattcggct actgtcagct ggaggcacc cacagcccaa gtggagagct
5581 tccggattac ctatgtgccc attacaggag gtacaccctc catggtaact gtggacggaa
5641 ccaagactca gaccaggctg gtgaaactca tacctggcgt ggagtacctt gtcagcatca
5701 tcgccatgaa gggctttgag gaaagtgaac ctgtctcagg gtcattcacc acagctctgg
5761 atggcccatc tggcctggtg acagccaaca tcactgactc agaagccttg gccaggtggc
5821 agccagccat tgccactgtg gacagttatg tcatctccta cacaggcgag aaagtgccag
5881 aaattacacg cacggtgtcc gggaacacag tggagtatgc tctgaccgac ctcgagcctg
5941 ccacggaata cacactgaga atctttgcag agaaagggcc ccagaagagc tcaaccatca
```

```
6001 ctgccaagtt cacaacagac ctcgattctc caagagactt gactgctact gaggttcagt
6061 cggaaactgc cctccttacc tggcgacccc cccgggcatc agtcaccggt tacctgctgg
6121 tctatgaatc agtggatggc acagtcaagg aagtcattgt gggtccagat accacctcct
6181 acagcctggc agacctgagc ccatccaccc actacacagc caagatccag gcactcaatg
6241 ggcccctgag gagcaatatg atccagacca tcttcaccac aattggactc ctgtaccct
6301 tccccaagga ctgctcccaa gcaatgctga atggagacac gacctctggc ctctacacca
6361 tttatctgaa tggtgataag gctgaggcgc tggaagtctt ctgtgacatg acctctgatg
6421 ggggtggatg gattgtgttc ctgagacgca aaaacggacg cgagaacttc taccaaaact
6481 ggaaggcata tgctgctgga tttggggacc gcagagaaga attctggctt gggctggaca
6541 acctgaacaa aatcacagcc caggggcagt acgagctccg ggtggacctg cgggaccatg
6601 gggagacagc ctttgctgtc tatgacaagt tcagcgtggg agatgccaag actcgctaca
6661 agctgaaggt ggaggggtac agtgggacag caggtgactc catggcctac cacaatggca
6721 gatccttctc cacctttgac aaggacacag attcagccat caccaactgt gctctgtcct
6781 acaaagggc tttctggtac aggaactgtc accgtgtcaa cctgatgggg agatatgggg
6841 acaataacca cagtcagggc gttaactggt ccactggaa gggccacgaa cactcaatcc
6901 agtttgctga gatgaagctg agaccaagca acttcagaaa tcttgaaggc aggcgcaaac
6961 gggcataaat tccagggacc actgggtgag agaggaataa ggcccagagc gaggaaagga
7021 ttttaccaaa gcatcaatac aaccagccca accatcggtc cacacctggg catttggtga
7081 gagtcaaagc tgaccatgga tccctgggc caacggcaac agcatgggcc tcacctcctc
7141 tgtgatttct ttcttgcac caaagacatc agtctccaac atgtttctgt tttgttgttt
7201 gattcagcaa aaatctccca gtgacaacat cgcaatagtt ttttacttct cttaggtggc
7261 tctgggaatg ggagagggt aggatgtaca ggggtagttt gttttagaac cagccgtatt
7321 ttacatgaag ctgtataatt aattgtcatt attttgtta gcaaagatta aatgtgtcat
7381 tggaagccat ccctttttt acatttcata caacagaaac cagaaaagca atactgtttc
7441 cattttaagg atatgattaa tattattaat ataataatga tgatgatgat gatgaaaact
7501 aaggattttt caagagatct ttctttccaa aacatttctg gacagtacct gattgtattt
7561 tttttttaaa taaaagcaca agtactttg agtttgttaa aaaaaaaaaa aaaaaa
```

*Figure 14 (con't)*

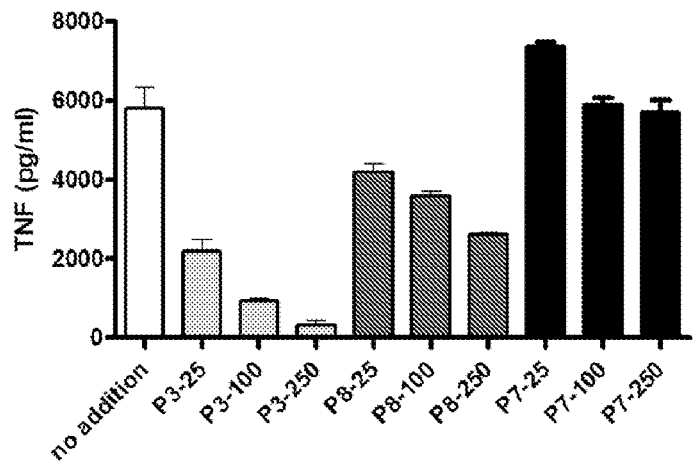
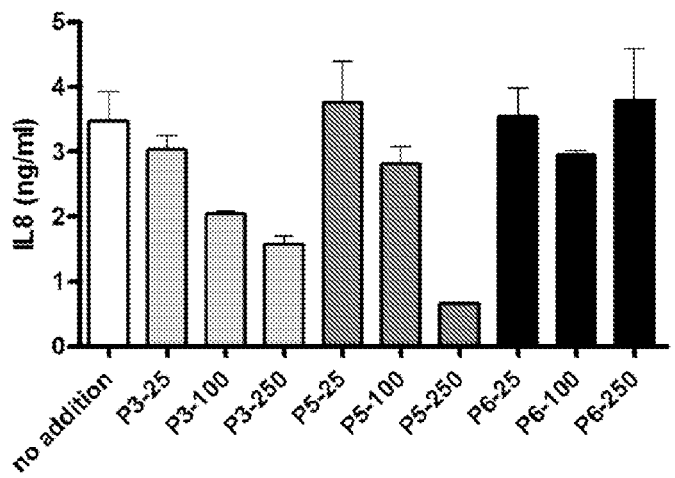
Figure 16

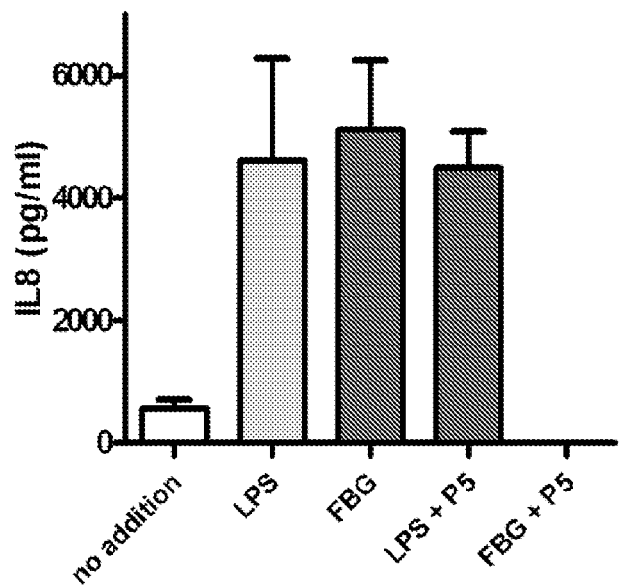
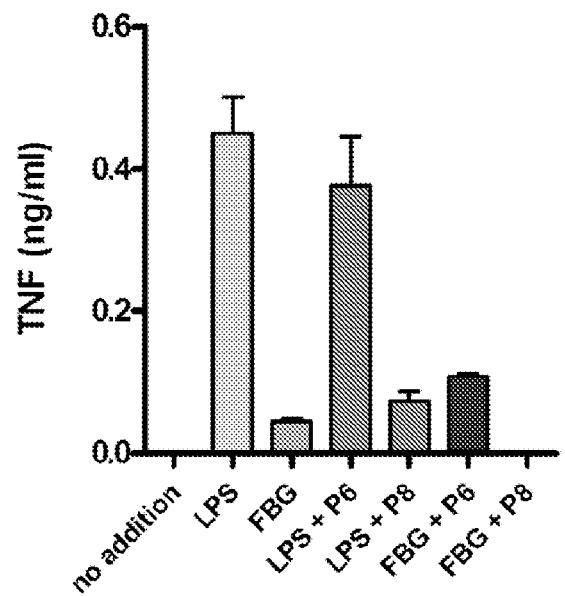
Figure 18

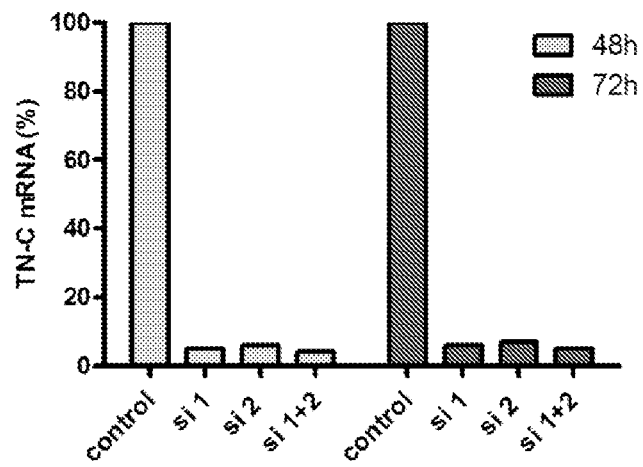
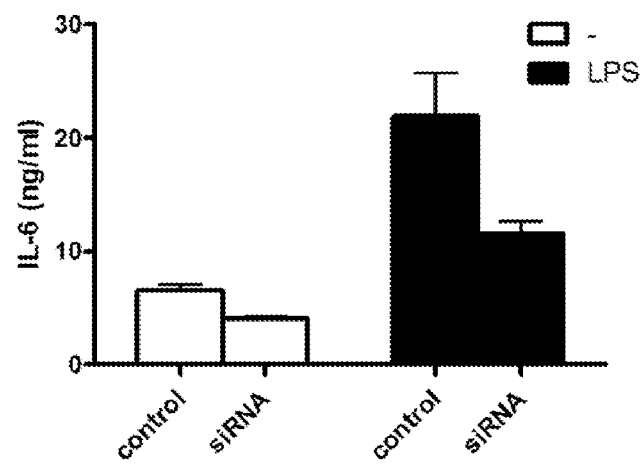
Figure 19

A

BIOMARKER AND USES THEREOF

CROSS REFERENCE TO RELATED APPLICATIONS

This application is the U.S. national phase application, pursuant to 35 U.S.C. § 371, of PCT international application Serial No.: PCT/GB2015/050052, filed Jan. 13, 2015, designating the United States and published in English, which claims the benefit of Great Britain Application No. 1400521.9, filed Jan. 13, 2014, the entire contents of each of which are incorporated herein by reference.

The present invention relates to citrullinated tenascin-C and its activity in chronic inflammation. In particular, the present invention relates to the use of citrullinated tenascin-C and/or autoantibodies with specificity for citrullinated tenascin-C as a biomarker for inflammatory disorders, such as rheumatoid arthritis.

Inflammation is the complex biological response of tissues to harmful stimuli, such as pathogens, tissue damage, or irritants. It is a protective attempt by the tissue to remove the injurious stimuli as well as initiate the healing process for the tissue. Abnormalities associated with inflammation comprise a large, unrelated group of disorders which underlie a variety of human diseases (inflammatory disorders). Examples of diseases with an inflammatory aspect include (but are not limited to) asthma, autoimmune disease, glomerulonephritis, allergy (hypersensitivities), inflammatory bowel diseases, reperfusion injury, rheumatoid arthritis and transplant rejection.

In particular, chronic inflammation is a debilitating and serious condition associated with many of the above diseases and is characterised by persistent inflammation and/or altered immune responses such as in autoimmune disease.

Rheumatoid arthritis (RA) is a typical example of, though by no means the only, a chronic inflammatory disorder. RA is characterized by synovial inflammation and destruction of joint cartilage and bone mediated by persistent synthesis of pro-inflammatory cytokines and matrix metalloproteinases (MMPs). Biological compounds that suppress the synthesis of inflammatory cytokines such as TNFα and IL-6 are successful at treating RA in the short-term. However, repeated treatments are required, which renders this an expensive therapeutic approach, and does not provide long-term remission. Furthermore, total systemic suppression of cytokine function is not without inherent problems such as increased infectious risk. Thus, despite advances in care, there remains an unmet need for an economical mode of treatment of chronic inflammatory that is efficacious over the long term (Smolen (2006) and Williams (2007)).

The mechanisms that underpin disease chronicity remain unclear and the factor(s) that drive the prolonged expression of inflammatory and destructive mediators are currently unknown.

Toll-like receptors (TLRs) play a key role in driving the production of inflammatory mediators in RA and blockade of TLR function may be of significant clinical benefit (reviewed in Brentano (2005) and O'Neill (2002)).

Tenascin-C is an ECM glycoprotein that is associated with tissue injury and wound repair. Tenascin-C is expressed specifically during active tissue remodelling during embryogenesis, being first observed during gastrulation and somite formation. In later stages of development expression is restricted to sites of branching morphogenesis of the mammary gland and the lung, in the developing skeleton, cardiovascular system and in connective tissues at sites of epithelial to mesenchymal transformation. Expression is down regulated once these processes cease and before embryogenesis is complete (Jones (2000)).

Tenascin-C is not normally expressed in healthy adult tissue but, in adults, is specifically and transiently up-regulated during acute inflammation and persistently expressed in chronic inflammation (reviewed in Chiquet-Ehrismann (2003)). Immunohistochemical studies show that little tenascin-C is expressed in normal human joints but levels are greatly increased in RA synovia, in areas of inflammation and fibrosis, specifically below the synovial lining, in the invading pannus and around blood vessels (Cutolo (1992), MacCachren (1992) and Salter (1993)). There is also a significant increase in tenascin-C levels in synovial fluid from RA patients (Chevalier (1994) and Hasegawa (2007)) and in RA cartilage (Salter (1993) and Chevalier (1994)).

Tenascin-C is a large hexameric protein of 1.5 million Da. Each chain comprises different domains, including an assembly domain (TA), EGF-like repeats (EGF-L), fibronectin type III-like repeats (TNIII) and a fibrinogen-like globe (FBG) (reviewed in Orend (2005)). The sequences of tenascin-C and its domains are shown in FIG. 13.

The inventors have shown previously that tenascin-C is an endogenous TLR4 ligand that it is required for destructive joint inflammation observed in arthritis and is involved in the prolonging of the inflammatory response characterising the chronic inflammatory disorder. In particular, tenascin-C has been shown to be an endogenous activator of TLR4 and demonstrated that this molecule is required for destructive joint inflammation (WO 2010/103289).

The tightly regulated pattern of expression of tenascin-C has made it an attractive target for diagnosing chronic inflammation. It is predominantly absent from healthy adults, however expression is specifically induced upon tissue injury. During acute inflammation tenascin-C is transiently expressed: induction often precedes inflammation and both mRNA and protein are absent from the tissue by the time inflammation is resolved (reviewed in Chiquet-Ehrismann (2003)).

Persistent expression of tenascin-C has now been shown to be associated with chronic inflammation. In addition to RA, increased tenascin-C levels are observed in other autoimmune diseases including multiple sclerosis (Gutowski (1999)) and Sjogrens disease (Amin (2001)), and in non-healing wounds and diabetic and venous ulcers (Loots (1998)). De novo synthesis of tenascin-C correlates well with the intensity of inflammation in diseases of the oral mucosa and plasma levels of tenascin-C are a reliable indicator for the activity of inflammatory bowel diseases before and after medication or surgery (reviewed in Chiquet-Ehrismann (2003)).

The inventors have now shown that, surprisingly, tenascin-C can be citrullinated in vitro and that citrullinated tenascin-C is preferentially found in patients with a chronic inflammatory disorder.

Citrullination results from the conversion of arginine residues to citrulline, mediated by peptidyl arginine deiminases (PADs). This post translational modification occurs physiologically in the skin and central nervous system and pathologically at sites of inflammation. The change significantly affects protein conformation, ionic interactions and susceptibility to proteolytic cleavage. Citrullination also creates new epitopes that lead to the generation of specific antibodies. Antibodies to citrullinated proteins (ACPAs) specifically recognise these citrullinated protein antigens. In addition, epitopes created by citrullination may also determine protein binding to HLA DR, T cell receptors and specific ligands within the innate immune system (67).

ACPAs have been found in RA patients and this is one way of diagnosing this disease. More recently, these antibodies have also been shown to actively promote disease. However, the proteins that these antibodies recognise are not well described. Until now, the only citrullinated antigens to have been identified in RA synovial fluid, be epitope-mapped and the specificity of their antibodies reproducibly confirmed in several laboratories (67) are fibrinogen, type II collagen, vimentin and α-enolase The inventors previously identified citrullinated α-enolase as an auto-antigen in RA and demonstrated its importance both in both diagnosis and aetiology (68-74). Recent data from other groups suggest that ACPAs and their antigens also actively contribute to disease pathogenesis. For example, citrullinated fibrinogen-containing immune complexes enhance experimental murine arthritis (75, 76) and synergistically promote cytokine synthesis by activation of toll-like receptor 4 (TLR4) and Fcγ receptors in human monocytes (77, 78).

It has long been known that fibrinogen is citrullinated and that antibodies to this form of fibrinogen are present in RA patients. Sokolove (2011) (16) shows that fibrinogen when citrullinated was a better activator of TLR4 than native fibrinogen and that citrullinated fibrinogen formed complexes with antibodies that activated inflammation via synergistic TLR-Fcγ receptor signalling. In this way modification of this protein exacerbates inflammation in RA.

The inventors previously identified the pro-inflammatory glycoprotein tenascin-C as an endogenous activator of innate and adaptive immune responses and showed that its expression is required for chronic joint inflammation in vivo (79, 80). Furthermore, high levels of tenascin-C were found in RA synovium (81) and serum (82). WO2013/088140 describes the use of tenascin-C as a biomarker for inflammatory disorders, and in particular, its use as a biomarker for erosive RA.

However, it has not previously been considered that tenascin-C may be citrullinated, nor that such citrullination might modulate the pro-inflammatory activity of tenascin-C or that citrullinated tenascin-C might be an autoantigen.

The inventors have now identified that full length tenascin-C, as well as its individual domains, including (but not only) the FBG domain, can be post translationally modified by citrullination in vitro. The inventors show that citrullinated FBG is better at stimulating cytokine (e.g. TNFα) synthesis by primary human macrophages than native FBG. The inventors have found that only RA patients, and not normal healthy controls, possess antibodies that recognise citrullinated tenascin-C and that serum from RA patients and normal healthy controls does not react with native or non citrullinated tenascin-C. The inventors also show that along with the FBG domain, other domains of tenascin-C are citrullinated in RA patients.

This is the first finding that tenascin-C can be citrullinated and the first demonstration that this modification of tenascin-C is relevant in RA. The inventors also show that citrullination acts to enhance the inflammatory capacity of tenascin-C providing at least three new major mechanisms by which this protein drives inflammation in RA. The pro-inflammatory effect of the citrullinated antigen, i.e. tenascin-C, is a finding of major significance, because it shows that both antibody (e.g. via Fcγ receptor signalling) and antigen (e.g. by TLR signalling) components of ACPA-containing tenascin-C immune complexes are pro-inflammatory. Thus citrullinated tenascin-C alone, autoantibodies to citrullinated tenascin-C alone or citrullinated tenascin-C-antibody complexes may drive inflammation in disease.

Even more surprisingly, the inventors have found that the amino acids that are citrullinated and targets of ACPA in FBG-C are not homologues to regions in fibrinogen. This is surprising as one might expect the same sequences to be modified in each protein.

Therefore, this is the first time that it has been shown that domains of tenascin-C, including the FBG domain are citrullinated in RA and that antibodies against citrullinated tenascin-C are found preferentially in RA patients.

According to a first aspect of the invention there is provided a method of determining the inflammatory disorder status of a subject comprising detecting the presence or absence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample from said subject.

The inflammatory disorder may be associated with any condition associated with inappropriate inflammation. Such disorders include, but are not limited to, rheumatoid arthritis (RA), autoimmune conditions, inflammatory bowel diseases (including Crohn's disease and ulcerative colitis), non-healing wounds, multiple sclerosis, cancer, atherosclerosis, sjogrens disease, diabetes, lupus erythrematosus (including systemic lupus erythrematosus), asthma, fibrotic diseases (including liver cirrhosis), pulmonary fibrosis, UV damage, psoriasis, psoriatic arthritis, ankylosing spondylitis, myositis and cardiovascular disease.

Of particular, but non-exclusive interest, the invention is concerned with chronic inflammation associated with rheumatoid arthritis (RA).

The phrase "inflammatory disorder status" includes any distinguishable manifestation of an inflammatory disorder, and includes, without limitation, the presence or absence of an inflammatory disorder, the risk of developing an inflammatory disorder, the stage of an inflammatory disorder, the progression of an inflammatory disorder, and the effectiveness or response of a subject to a treatment for an inflammatory disorder.

In a preferred embodiment, the inflammatory disorder referred to is rheumatoid arthritis, and the method of the invention allows, without limitation, the determination of the presence or absence of rheumatoid arthritis, the risk of developing rheumatoid arthritis, the stage of rheumatoid arthritis, the progression of rheumatoid arthritis, the remission of arthritis, the best likely treatment for rheumatoid arthritis and the effectiveness or response of a subject to a treatment for rheumatoid arthritis.

The method of the invention may be used, for example, for any one or more of the following: to diagnose rheumatoid arthritis in a subject; to assess the chance of a subject developing rheumatoid arthritis; to advise on the prognosis for a subject with rheumatoid arthritis; to monitor disease progression; to advise on treatment options and to monitor effectiveness or response of a subject to a treatment for rheumatoid arthritis.

Preferably the method allows the diagnosis of rheumatoid arthritis in a subject from the analysis of the presence or absence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample provided by the subject. The method may allow a diagnosis of rheumatoid arthritis to be given in a subject with no other symptoms of rheumatoid arthritis.

The presence, and optionally the level, of the citrullinated tenascin-C and/or one or more fragments of citrullinated tenascin-C in a sample may be determined by any suitable assay, which may comprise the use of any of the group comprising immunoassays, spectrometry, western blot, ELISA, immunoprecipitation, slot or dot blot assay, isoelectric focussing, SDS-PAGE and antibody microarray immunohistological staining, radio immuno assay (RIA), fluoroimmunoassay, an immunoassay using an avidin-biotin or streptoavidin-biotin system, etc or combinations thereof. These methods are well known to persons skilled in the art.

The presence, and optionally the level, of citrullinated tenascin-C and/or one or more fragments of citrullinated tenascin-C in a sample may be determined by using an antibody specific to citrullinated tenascin-C and/or one or more fragments of citrullinated tenascin-C that does not bind native tenascin-C and then immunoassaying e.g. by ELISA and/or western blot. For either serum or tissue/cells this is preferably a sandwich ELISA, i.e. one citrullinated tenascin-C (citTNC) Ab used as capture, then adding serum/tissue lysate as suitable dilution, then a second, different citTNC antibody to detect. A second antibody can be labelled for detection or indirect detection—as in any standard ELISA protocol. In the event that two different suitable citTNC antibodies cannot be found, the method uses a direct ELISA made up of serum/tissue lysate on plates and the antibody added directly to this. Alternatively, a non-citrullinated-TNC antibody may be used for capture, and a citrullinated-TNC antibody may be used for detection, or vice versa.

In one embodiment, the ratio of native and citrullinated TNC may be determined. The ratio of citrullinated TNC to native TNC that is predictive or diagnostic for rheumatoid arthritis, and in particular erosive rheumatoid arthritis, may be at least 1:2. The ratio of citrullinated TNC to native TNC hat is predictive or diagnostic for rheumatoid arthritis, and in particular erosive rheumatoid arthritis, may be at least 1:1. The ratio of citrullinated TNC to native TNC hat is predictive or diagnostic for rheumatoid arthritis, and in particular erosive rheumatoid arthritis, may be at least 2:1. The ratio of citrullinated TNC to native TNC hat is predictive or diagnostic for rheumatoid arthritis, and in particular erosive rheumatoid arthritis, may be at least 5:1. The ratio of citrullinated TNC to native TNC hat is predictive or diagnostic for rheumatoid arthritis, and in particular erosive rheumatoid arthritis, may be at least 10:1. The ratio of citrullinated TNC to native TNC hat is predictive or diagnostic for rheumatoid arthritis, and in particular erosive rheumatoid arthritis, may be at least 100:1. The level of citrullinated TNC that is predictive or diagnostic for rheumatoid arthritis, and in particular erosive rheumatoid arthritis, may be a level of more than 20 ng/ml of serum or plasma. In another embodiment, the level of citrullinated TNC that is predictive or diagnostic for rheumatoid arthritis, and in particular erosive rheumatoid arthritis, may be a level of more than 25 ng/ml of serum or plasma. Alternatively, the level of citrullinated TNC that is predictive or diagnostic for rheumatoid arthritis, and in particular erosive rheumatoid arthritis, may be a level of more than 31 ng/ml of serum or plasma. The level of citrullinated TNC that is predictive or diagnostic for rheumatoid arthritis, and in particular erosive rheumatoid arthritis, may be a level of more than 33 ng/ml of serum or plasma. The level of citrullinated TNC that is predictive or diagnostic for rheumatoid arthritis, and in particular erosive rheumatoid arthritis, may be a level of more than 50% increase in serum or plasma cTNC relative to a normal sample level of cTNC. The level of citrullinated TNC that is predictive or diagnostic for rheumatoid arthritis, and in particular erosive rheumatoid arthritis, may be a level of more than 50% increase in serum or plasma cTNC relative to a normal sample level of TNC. For example, a normal sample may be as determined from a sample from a non-RA, or non-erosive RA patient. Alternatively, a normal sample as determined from a sample of the same patient before they were afflicted with RA or erosive RA.

In an embodiment determining the presence of autoantibodies to citrullinated TNC, the presence of autoantibodies to citrullinated TNC may be predictive or diagnostic for rheumatoid arthritis, and in particular erosive rheumatoid arthritis. Alternatively, at least a 50% increase in the presence of autoantibodies to citrullinated TNC may be predictive or diagnostic for rheumatoid arthritis, and in particular erosive rheumatoid arthritis.

Alternatively, tenascin-C and/or fragments of tenascin-C may be immune precipitated and then western blotting or mass spectrometry may be used to determine if the tenascin-C is citrullinated.

Samples containing autoantibodies having specificity for citrullinated tenascin-C and/or fragments of citrullinated tenascin-C may be determined using western blotting with RA serum as in the examples.

Alternatively, the residues that are citrullinated in tenascin-C and/or fragments of citrullinated tenascin-C may be better defined and then a peptide assay may be created (either a western blot as above, and/or an ELISA approach). Only the peptide which is citrullinated is created and, as a control, a non citrullinated peptide. The plate is coated with peptide and RA serum applied and used to detect antibody (see Lundberg (2008) for details of the methods). The citrullinated tenascin-C peptide for use in the assay may comprise any tenascin-C peptide comprising a citrullinated residue selected from any of the group comprising residues 50, 51, 55, 72, 120, 169, 173, 209, 214, 219, 220 and 222; or combinations thereof (residue numbers as determined from SEQ ID NO: 70). The citrullinated tenascin-C peptide for use in the assay may comprise any tenascin-C peptide comprising a citrullinated residue selected from any of the group comprising residues 55, 72, 120, 169, 173, 209, 214, 219, and 220; or combinations thereof. In one embodiment, the peptide may comprise citrullinated residues CIT55, CIT209, CIT214, CIT219, and/or CIT220. In another embodiment, the peptide may comprise citrullinated residue CIT50. In another embodiment, the peptide may comprise citrullinated residue CIT51. In another embodiment, the peptide may comprise citrullinated residue CIT55. Alternatively, the peptide may comprise citrullinated residue CIT209 and/or CIT214. Alternatively, the peptide may comprise citrullinated residue CIT219 and/or CIT220.

Alternatively, the peptide may comprise citrullinated residue CIT222. Combinations of the above peptides may be used in a pool. An equivalent non-citrullinated peptide of the same sequence may be used as the assay control.

The citrullinated tenascin-C peptide, or fragment thereof, for use in a peptide assay may be in a looped or cyclic formation, for example to aid antibody recognition.

The citrullinated tenascin-C peptide, or fragment thereof, for use in a peptide assay may comprise a sequence of part of SEQ ID NO: 70 having one or more citrullinated residues selected from CIT50, CIT51, CIT55, CIT72, CIT120, CIT169, CIT173, CIT209, CIT214, CIT219, CIT220 and CIT222; or combinations thereof. Alternatively, the citrullinated tenascin-C peptide, or fragment thereof, for use in a peptide assay may comprise a sequence of part of SEQ ID NO: 70 having one or more citrullinated residues selected from CIT55, CIT72, CIT120, CIT169, CIT173, CIT209, CIT214, CIT219, and CIT220; or combinations thereof. The citrullinated tenascin-C peptide, or fragment thereof, for use in a peptide assay may comprise a sequence of part of SEQ ID NO: 70 having citrullinated residue CIT50. The citrullinated tenascin-C peptide, or fragment thereof, for use in a peptide assay may comprise a sequence of part of SEQ ID NO: 70 having citrullinated residue CIT51. The citrullinated tenascin-C peptide, or fragment thereof, for use in a peptide assay may comprise a sequence of part of SEQ ID NO: 70 having citrullinated residue CIT55. The citrullinated tenascin-C peptide, or fragment thereof, for use in a peptide assay may comprise a sequence of part of SEQ ID NO: 70 having citrullinated residue CIT72. The citrullinated tenascin-C peptide, or fragment thereof, for use in a peptide assay may comprise a sequence of part of SEQ ID NO: 70 having citrullinated residue CIT120. The citrullinated tenascin-C peptide, or fragment thereof, for use in a peptide assay may comprise a sequence of part of SEQ ID NO: 70 having citrullinated residue CIT169. The citrullinated tenascin-C peptide, or fragment thereof, for use in a peptide assay may comprise a sequence of part of SEQ ID NO: 70 having citrullinated residue CIT173. The citrullinated tenascin-C peptide, or fragment thereof, for use in a peptide assay may comprise a sequence of part of SEQ ID NO: 70 having citrullinated residue CIT209. The citrullinated tenascin-C peptide, or fragment thereof, for use in a peptide assay may comprise a sequence of part of SEQ ID NO: 70 having citrullinated residue CIT214. The citrullinated tenascin-C peptide, or fragment thereof, for use in a peptide assay may comprise a sequence of part of SEQ ID NO: 70 having citrullinated residue CIT219. The citrullinated tenascin-C peptide, or fragment thereof, for use in a peptide assay may comprise a sequence of part of SEQ ID NO: 70 having citrullinated residue CIT220. The citrullinated tenascin-C peptide, or fragment thereof, for use in a peptide assay may comprise a sequence of part of SEQ ID NO: 70 having citrullinated residue CIT222. Two or more different fragments of SEQ ID NO: 70 may be used, which have different citrullinated residues relative to each other. Reference to fragments or sequences of SEQ ID NO: 70 may also include variants thereof. For example, a variant may have a sequence from SEQ ID NO: 70 plus additional amino acid residues or modifications.

The citrullinated tenascin-C peptide or the sequence of part of SEQ ID NO: 70 may comprise between about 5 and about 25 consecutive amino acid residues. The citrullinated tenascin-C peptide or the sequence of part of SEQ ID NO: 70 may comprise between about 10 and about 25 consecutive amino acid residues. The citrullinated tenascin-C peptide or the sequence of part of SEQ ID NO: 70 may comprise between about 15 and about 25 consecutive amino acid residues. The citrullinated tenascin-C peptide or the sequence of part of SEQ ID NO: 70 may comprise between about 18 and about 22 consecutive amino acid residues. The citrullinated tenascin-C peptide or the sequence of part of SEQ ID NO: 70 may comprise between about 8 and about 20 consecutive amino acid residues.

For example, the citrullinated tenascin-C peptide for use in a peptide assay may comprise a peptide sequence selected from any of the group comprising SEQ ID NO: 55, SEQ ID NO: 57, SEQ ID NO: 59, SEQ ID NO: 61, SEQ ID NO: 63 and SEQ ID NO: 64; or variants thereof and/or combinations thereof. The citrullinated tenascin-C peptide for use in a peptide assay may comprise a peptide sequence of SEQ ID NO: 55 or a variant thereof. The citrullinated tenascin-C peptide for use in a peptide assay may comprise a peptide sequence of SEQ ID NO: 57 or a variant thereof. The citrullinated tenascin-C peptide for use in a peptide assay may comprise a peptide sequence of SEQ ID NO: 59 or a variant thereof. The citrullinated tenascin-C peptide for use in a peptide assay may comprise a peptide sequence of SEQ ID NO: 61 or a variant thereof. The citrullinated tenascin-C peptide for use in a peptide assay may comprise a peptide sequence of SEQ ID NO: 63 or a variant thereof. The citrullinated tenascin-C peptide for use in a peptide assay may comprise a peptide sequence of SEQ ID NO: 64 or a variant thereof.

The presence of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample from said subject may be sufficient to conclude the subject has an inflammatory disorder.

The method of the invention may comprise the further step of comparing the level of: (i) citrullinated tenascin-C and/or one or more fragments of citrullinated tenascin-C; and/or (ii) autoantibodies with specificity for citrullinated tenascin-C and/or one or more fragments of citrullinated tenascin-C, determined in the sample with one or more reference values.

Preferably the reference value, to which the determined levels of citrullinated tenascin-C or fragments thereof and/or autoantibodies with specificity for citrullinated tenascin-C or fragments thereof are compared, is the level of citrullinated tenascin-C or fragments thereof and/or autoantibodies with specificity for citrullinated tenascin-C or fragments thereof, observed in one or more subjects that do not have any detectable inflammatory disorder, such as rheumatoid arthritis, or any clinical symptoms of an inflammatory disorder, such as rheumatoid arthritis, and have so called "normal values" of citrullinated tenascin-C or fragments thereof and/or autoantibodies with specificity for citrullinated tenascin-C or fragments thereof.

In a further embodiment the ratio of citrullinated tenascin-C or fragments thereof to native tenascin-C may be considered and compared.

Alternatively the reference value, to which the determined levels of citrullinated tenascin C or fragments thereof and/or autoantibodies with specificity for citrullinated tenascin-C or fragments thereof are compared, may be a previous value obtained for a specific subject. This kind of reference value may be used if the method is to be used to monitor progression of disease or to monitor the response of a subject to a particular treatment.

The presence, or level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, may be used to stratify patients. This stratification may be used to decide the appropriate treatment. For example, the patients may be stratified by detecting specific citrullinated residues in their citrullinated tenascin C or fragments thereof. The patient may be positive for CIT55 (i.e. residue 55 of SEQ ID NO: 70 is citrullinated). Additionally, or alternatively patients may be positive for CIT209 and/or CIT214. The patients may be positive for CIT219 and/or CIT220. In some embodiments, the patient may be positive for CIT55, CIT72, CIT120, CIT169, CIT173, CIT209, CIT214, CIT219, and CIT220; or positive for combinations of these citrullinated residues. In other embodiments, the patient may be positive for CIT50, CIT51, CIT55, CIT72, CIT120, CIT169, CIT173, CIT209, CIT214, CIT219, CIT220 and CIT222; or positive for combinations of these citrullinated residues. Therefore, in one embodiment, the citrullination of specific residues for a patient is determined. The citrullination of one or more of specific residues 50, 51, 55, 72, 120, 169, 173, 209, 214, 219, 220 and/or 222 may be determined for a patient (residues numbered according to SEQ ID NO: 70). Alternatively, the citrullination of one or more of specific residues 55, 72, 120, 169, 173, 209, 214, 219 and/or 220 may be determined for a patient (residues numbered according to SEQ ID NO: 70).

Alternatively or additionally, in an embodiment detecting autoantibodies, the epitope of the autoantibody is differentiated based on having the specific citrullinated residues, for example one or more of CIT50, CIT51, CIT55, CIT72, CIT120, CIT169, CIT173, CIT209, CIT214, CIT219, CIT220 and CIT222; or one or more of CIT55, CIT72, CIT120, CIT169, CIT173, CIT209, CIT214, CIT219, and CIT220. The epitope of the autoantibody may be differentiated based on having the specific citrullinated residue CIT50. The epitope of the autoantibody may be differentiated based on having the specific citrullinated residue CIT51. The epitope of the autoantibody may be differentiated based on having the specific citrullinated residue CIT55. The epitope of the autoantibody may be differentiated based on having the specific citrullinated residue CIT72. The epitope of the autoantibody may be differentiated based on having the specific citrullinated residue CIT120. The epitope of the autoantibody may be differentiated based on having the specific citrullinated residue CIT169. The epitope of the autoantibody may be differentiated based on having the specific citrullinated residue CIT173. The epitope of the autoantibody may be differentiated based on having the specific citrullinated residue CIT209. The epitope of the autoantibody may be differentiated based on having the specific citrullinated residue CIT214. The epitope of the autoantibody may be differentiated based on having the specific citrullinated residue CIT219. The epitope of the autoantibody may be differentiated based on having the specific citrullinated residue CIT220. The epitope of the autoantibody may be differentiated based on having the specific citrullinated residue CIT222.

The presence of different citrullination or related epitopes may define how to target citFBG. For example, if CIT55 was detected the immunogenic activity of FBG may be blocked by a therapeutic agent. If the integrin binding site was citrullinated (e.g. CIT169 and/or CIT173), action of this domain may be blocked by a therapeutic agent.

The method of the invention may also be used to monitor progression of an inflammatory disease, such as rheumatoid arthritis, and/or to monitor the efficacy of treatments administered to a subject. This may be achieved by analysing samples taken from a subject at various time points following initial diagnosis and monitoring the changes in the levels of (i) citrullinated tenascin-C and/or one or more fragments of citrullinated tenascin-C; and/or (ii) autoantibodies with specificity for citrullinated tenascin-C and/or one or more fragments of citrullinated tenascin-C, and comparing these levels to normal and/or reference values. In this case reference levels may include the initial levels of citrullinated tenascin-C or one or more fragments thereof and/or autoantibodies with specificity for citrullinated tenascin-C or one or more fragments thereof in the subject; or the levels of citrullinated tenascin-C or one or more fragments thereof and/or autoantibodies with specificity for citrullinated tenascin-C or one or more fragments thereof in the subject when they were last tested, or both.

The method of the invention may also be used to determine the appropriate treatment for a subject. The method may be used to offer personalised medicine solutions. In one embodiment, the presence of (i) citrullinated tenascin-C and/or one or more fragments of citrullinated tenascin-C; and/or (ii) autoantibodies with specificity for citrullinated tenascin-C and/or one or more fragments of citrullinated tenascin-C in a sample, may be sufficient to result in a diagnosis of an inflammatory disorder such as rheumatoid arthritis, and may be used to indicate what the most appropriate therapy is.

It may be appropriate if a subject has (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample obtained therefrom to use a therapeutically effective amount of one or more of an anti-TNF drug; an anti-IL17 therapy; a T-cell co-stimulation modulator (such as Orencia™—abatacept): an interleukin-6 (IL-6) inhibitor (such as Actemra™—tocilizumab); an anti-CD20 antibody (such as Rituxan™—rituxumab); or a B cell activating factor (such as anti-BAFF). Other alternative therapies include inhibitors of janus kinase (JAK) (such as Tofacitinib™) I, inhibitors of spleen tyrosine kinase (Syk) (such as Fostamatinib™), antiTNC antibodies or antibodies to citrullinated tenascin-C domains.

Alternatively, or additionally, the therapy may be the administration of a therapeutically effective amount of an agent that modulates the biological activity of citrullinated tenascin-C or one or more fragments of citrullinated tenascin-C. The agent may modulate the biological activity of citrullinated tenascin-C or one or more fragments thereof in one or more of the following ways:

by altering one or more physical properties of citrullinated tenascin-C or one or more fragments thereof;
  by altering the binding properties of citrullinated tenascin-C or one or more fragments thereof;
  by altering the antigenicity of citrullinated tenascin-C or one or more fragments thereof;
  by altering the level of citrullination of citrullinated tenascin-C or one or more fragments thereof;
  by altering the ratio of citrullinated tenascin-C to non-citrullinated tenascin-C, or one or more fragments thereof, for example by altering the citrullination at one or more specific domains (e.g. the FBG domain);
  by altering one or more specific citrullinated residue(s) of tenascin-C, or fragment thereof, to a non-citrullinated form of the residue(s), wherein the specific citrullinated residue(s) may be selected from any of the group comprising residues 55, 72, 120, 169, 173, 209, 214, 219, and 220; or combinations thereof; or
  by altering one or more specific citrullinated residue(s) of tenascin-C, or fragment thereof, to a non-citrullinated form of the residue(s), wherein the specific citrullinated residue(s) may be selected from any of the group comprising residues 50, 51, 55, 72, 120, 169, 173, 209, 214, 219, 220 and 222; or combinations thereof.

The specific citrullinated residues may comprise one or more of CIT55, CIT209, CIT214, CIT219 and CIT220. The specific citrullinated residue may comprise CIT50. The specific citrullinated residue may comprise CIT51. The specific citrullinated residue may comprise CIT55. In another embodiment, the specific citrullinated residues may comprise CIT209 and/or CIT214. Alternatively, the specific citrullinated residues may comprise CIT219 and/or CIT220. The specific citrullinated residue may comprise CIT222. The specific citrullinated residues may be detected in the form of epitopes. For example, the method may comprise the detection of an epitope, wherein the epitope comprises at least one citrullinated residue selected from CIT55, CIT209, CIT214, CIT219 and CIT220; or combinations thereof. The epitope may comprise citrullinated residue CIT50. The epitope may comprise citrullinated residue CIT51. The epitope may comprise citrullinated residue CIT55. The epitope may comprise citrullinated residue CIT209. The epitope may comprise citrullinated residue CIT214. The epitope may comprise citrullinated residue CIT219. The epitope may comprise citrullinated residue CIT220. The epitope may comprise citrullinated residue CIT222.

The agent that modulates the biological activity of citrullinated tenascin-C or one or more fragments thereof may down-regulate or up-regulate the biological activity of citrullinated tenascin-C or one or more fragments thereof.

The agent that modulates the biological activity of citrullinated tenascin-C or one or more fragments thereof may be an inhibitor of citrullination of tenascin-C; or an inhibitor of the binding properties of citrullinated tenascin-C; or a competitive binding inhibitor of citrullinated tenascin-C.

The agent that modulates the biological activity of citrullinated tenascin-C or one or more fragments thereof may be an antagonist of the TLR-4 receptor and/or the Fcγ receptor.

The agent that modulates the biological activity of citrullinated tenascin-C or one or more fragments thereof may be selected from the group consisting of short interfering RNA (SiRNA) molecules, short hairpin RNA molecules (shRNA), antisense oligonucleotides, compounds with binding affinity for citrullinated tenascin-C, antibodies (polyclonal or monoclonal) and antigen-binding fragments thereof, small inhibitor compounds, a domain of citrullinated tenascin-C or variant thereof, polypeptides and proteins. Where the agent is an antibody or antigen-binding fragment it may have specificity for Toll Like Receptor 4 (TLR4), citrullinated tenascin-C or a fragment/domain thereof; or a binding affinity for the FBG domain of citrullinated tenascin-C.

The agent that modulates the biological activity of citrullinated tenascin-C or one or more fragments thereof may modulate the biological activity of the FBG domain of citrullinated tenascin-C.

The agent that modulates the biological activity of citrullinated tenascin-C or one or more fragments thereof may modulate the activity of citrullinated tenascin-C which is citrullinated at least at the FBG domain; only at the FBG domain; or at one or more domains other than the FBG domain (e.g. the fibronectin type III like repeats). The citrullinated tenascin-C or one or more fragments of citrullinated tenascin-C may be citrullinated at one or more specific residue(s) wherein the specific residue(s) may be selected from any of the group comprising residues 50, 51, 55, 72, 120, 169, 173, 209, 214, 219, 220, 222; or combinations thereof (residue numbers as determined from SEQ ID NO: 70). Alternatively, the citrullinated tenascin-C or one or more fragments of citrullinated tenascin-C may be citrullinated at one or more specific residue(s) wherein the specific residue(s) may be selected from any of the group comprising residues 55, 72, 120, 169, 173, 209, 214, 219, and 220; or combinations thereof (residue numbers as determined from SEQ ID NO: 70). The specific citrullinated residues may comprise CIT55, CIT209, CIT214, CIT219, and/or CIT220. The specific citrullinated residue may comprise CIT50. The specific citrullinated residue may comprise CIT51. The specific citrullinated residue may comprise CIT55. In another embodiment, the specific citrullinated residues may comprise CIT209 and/or CIT214. Alternatively, the specific citrullinated residues may comprise CIT219 and/or CIT220. The specific citrullinated residue may comprise CIT222. The specific citrullinated residues may be detected in the form of epitopes. For example, the method may comprise the detection of an epitope, wherein the epitope comprises at least one citrullinated residue selected from CIT55, CIT209, CIT214, CIT219, and CIT220; or combinations thereof. Alternatively, the method may comprise the detection of an epitope, wherein the epitope comprises at least one citrullinated residue selected from CIT50, CIT51, CIT55, CIT209, CIT214, CIT219, CIT22 and CIT222; or combinations thereof. The epitope may comprise citrullinated residue CIT50. The epitope may comprise citrullinated residue CIT51. The epitope may comprise citrullinated residue CIT55. The epitope may comprise citrullinated residue CIT209. The epitope may comprise citrullinated residue CIT214. The epitope may comprise citrullinated residue CIT219. The epitope may comprise citrullinated residue CIT220. The epitope may comprise citrullinated residue CIT222.

The sample may be a sample of blood, serum, plasma, synovial fluid and/or joint tissue derived from the subject.

Preferably the method of the invention is carried out in vitro.

The subject may be mammal, and is preferably a human, but may alternatively be a monkey, ape, cat, dog, cow, horse, rabbit or rodent.

Information regarding the inflammatory disorder status of a subject may be relayed to a third party, such as a doctor, other medical professional, pharmacist or other interested party. This information may be relayed digitally, for example via email, SMS or other digital means.

According to another aspect of the invention there is provided a kit for use in determining the inflammatory disorder status of a subject comprising at least one agent for detecting the presence, of the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample provided by the subject.

In a preferred embodiment the kit is for use in determining the rheumatoid arthritis status of a subject.

The agent may be an antibody if the presence or level of citrullinated tenascin-C or one or more fragments of citrullinated tenascin-C is to be detected/determined. Alternatively, if the presence or level of autoantibodies with specificity for citrullinated tenascin-C or one or more fragments of citrullinated tenascin-C is to be detected/determined, the agent may be citrullinated tenascin-C or an antigenic fragment or peptide of citrullinated tenascin-C. Alternatively, antibodies may be used to determine the presence or level of autoantibodies with specificity for citrullinated tenascin-C or one or more fragments of citrullinated tenascin-C The kit may comprise instructions for suitable operational parameters in the form of a label or separate insert. The instructions may inform a user about how to collect the sample.

The kit may comprise (i) citrullinated tenascin-C and/or one or more fragments of citrullinated tenascin-C; and/or (ii) autoantibodies with specificity for citrullinated tenascin-C and/or one or more fragments of citrullinated tenascin-C, samples to be used as standard(s) for calibration and comparison. The kit may also comprise instructions to compare the level of (i) citrullinated tenascin-C and/or one or more fragments of citrullinated tenascin-C; and/or (ii) autoantibodies with specificity for citrullinated tenascin-C and/or one or more fragments of citrullinated tenascin-C, detected in a sample with a calibration sample or chart. The kit may also include instructions indicating what level of (i) citrullinated tenascin-C and/or one or more fragments of citrullinated tenascin-C; and/or (ii) autoantibodies with specificity for citrullinated tenascin-C and/or one or more fragments of citrullinated tenascin-C, is diagnostic of an inflammatory disorder. The instructions may indicate that the presence of any (i) citrullinated tenascin-C and/or one or more fragments of citrullinated tenascin-C; and/or (ii) autoantibodies with specificity for citrullinated tenascin-C and/or one or more fragments of citrullinated tenascin-C, is diagnostic of an inflammatory disorder.

According to a yet further aspect, the invention provides the use of the determination of the presence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample obtained from a subject as a means of assessing the inflammatory disorder status in the subject. The sample may be blood, serum, plasma, synovial fluid and/or joint tissue In a preferred embodiment the invention provides the use of the determination of the presence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a blood or serum sample as a means of assessing the rheumatoid arthritis status in an individual.

According to another aspect the invention provides the use of (i) citrullinated tenascin-C and/or one or more fragments of citrullinated tenascin-C; and/or (ii) autoantibodies with specificity for citrullinated tenascin-C and/or one or more fragments of citrullinated tenascin-C, as a biomarker for an inflammatory disorder.

According to a further aspect the invention provides (i) citrullinated tenascin-C and/or one or more fragments of citrullinated tenascin-C; and/or (ii) autoantibodies with specificity for citrullinated tenascin-C and/or one or more fragments of citrullinated tenascin-C, for use in a method of determining the appropriate treatment for a subject having an inflammatory disorder.

According to a further aspect the invention provides an assay comprising:
i) measuring the presence of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample from a patient who presents at least one symptom of rheumatoid arthritis for determining the likelihood of rheumatoid arthritis in the patient; and
ii) concluding if (i) citrullinated tenascin-C and/or one or more fragments of citrullinated tenascin-C; and/or (ii) autoantibodies with specificity for citrullinated tenascin-C and/or one or more fragments of citrullinated tenascin-C, are present in the sample this indicates the likelihood of rheumatoid arthritis in the patient.

The assay of this aspect of the invention may include the step of measuring the level of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample from a patient, and comparing the measured or quantified amount of (i) citrullinated tenascin-C and/or one or more fragments of citrullinated tenascin-C; and/or (ii) autoantibodies with specificity for citrullinated tenascin-C and/or one or more fragments of citrullinated tenascin-C, with a reference value, and if the amount of (i) citrullinated tenascin-C and/or one or more fragments of citrullinated tenascin-C; and/or (ii) autoantibodies with specificity for citrullinated tenascin-C and/or one or more fragments of citrullinated tenascin-C, is increased relative to the reference value, identifying the subject as having an increased probability of having rheumatoid arthritis. Preferably the reference value is from a control subject who does not have rheumatoid arthritis.

The invention may provide a method of treating an inflammatory disorder in a subject comprising detecting the presence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, in a sample from the subject and administering a treatment based on the presence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C, observed.

According to a further aspect of the invention there is provided a method of determining the appropriate treatment for a subject having an inflammatory disorder.

In one embodiment the method comprises the steps of:
(i) providing a sample derived from the subject; and
(ii) testing the sample for the presence of (i) citrullinated tenascin-C and/or one or more fragments of citrullinated tenascin-C; and/or (ii) autoantibodies with specificity for citrullinated tenascin-C and/or one or more fragments of citrullinated tenascin-C, wherein the presence or absence of (i) citrullinated tenascin-C and/or one or more fragments of citrullinated tenascin-C; and/or (ii) autoantibodies with specificity for citrullinated tenascin-C and/or one or more fragments of citrullinated tenascin-C, indicates the appropriate treatment.

In a preferred embodiment the presence of (i) citrullinated tenascin-C and/or one or more fragments of citrullinated tenascin-C; and/or (ii) autoantibodies with specificity for citrullinated tenascin-C and/or one or more fragments of citrullinated tenascin-C, determines that the subject should be administered an effective amount of an agent or composition, the agent or composition may be one or more of anti-TNF drug; an anti-IL17 therapy; a T-cell co-stimulation modulator (such as Orencia™—abatacept, a fusion protein comprising the Fc region of IgG1 fused to the extracellular domain of CTLA-4); an interleukin-6 (IL-6) inhibitor (such as Actemra™—tocilizumab, a humanized monoclonal antibody which binds to the IL-6 receptor); an anti-CD20 antibody (such as Rituxan™—rituxumab, a chimeric monoclonal antibody which binds to the B cell surface protein CD20); a B cell activating factor (such as anti-B cell activating factor (BAFF)); an inhibitor of janus kinase (JAK) (such as Tofacitinib™, a chemical compound having IUPAC name 3-[(3R,4R)-4-methyl-3-[methyl(7H-pyrrolo [2,3-d]pyrimidin-4-yl)amino]piperidin-1-yl]-3-oxopropanenitrile); an inhibitor of spleen tyrosine kinase (Syk) (such as Fostamatinib™, a chemical compound having IUPAC name [6-({5-Fluoro-2-[(3,4,5-trimethoxyphenyl)amino]pyrimidin-4-yl}amino)-2,2-dimethyl-3-oxo-2,3-dihydro-4H-pyrido[3,2-b][1,4]oxazin-4-yl]methyl dihydrogen phosphate); anti-recombinant tenascin-C (TNC) antibodies or antibodies to citrullinated tenascin-C domains, and an agent that modulates the biological activity of citrullinated and/or non-citrullinated tenascin-C.

The invention may also provide a method for treating an inflammatory disorder in a subject comprising;
  i) obtaining a sample from a subject;
  ii) analysing the sample for the presence or absence of (i) citrullinated tenascin-C and/or one or more fragments of citrullinated tenascin-C; and/or (ii) autoantibodies with specificity for citrullinated tenascin-C and/or one or more fragments of citrullinated tenascin-C;
  iii) diagnosing the subject as having an inflammatory disorder if (i) citrullinated tenascin-C and/or one or more fragments of citrullinated tenascin-C; and/or (ii) autoantibodies with specificity for citrullinated tenascin-C and/or one or more fragments of citrullinated tenascin-C, is present; and
  iv) administering an anti-inflammatory treatment to the diagnosed subject.

The inflammatory disorder may be as described herein and may be, for example, rheumatoid arthritis.

The anti-inflammatory treatment may be any treatment described herein with reference to any aspect or embodiment of the invention.

According to another aspect the invention provides a method of selecting a subject for treatment for an inflammatory disorder comprising:
  i) obtaining a sample from a subject;
  ii) analysing the sample for the presence or absence, or the level, of (i) citrullinated tenascin-C and/or one or more fragments of citrullinated tenascin-C; and/or (ii) autoantibodies with specificity for citrullinated tenascin-C and/or one or more fragments of citrullinated tenascin-C;
  iii) if (i) citrullinated tenascin-C and/or one or more fragments of citrullinated tenascin-C; and/or (ii) autoantibodies with specificity for citrullinated tenascin-C and/or one or more fragments of citrullinated tenascin-C, are present, or elevated relative to a normal control, selecting the subject for treatment for an inflammatory disorder.

According to a further aspect the invention provides a device for determining the inflammatory status of a subject, wherein the device is capable of emitting an external signal which is indicative of the inflammatory status of the subject. Preferably the device is capable of accepting a sample obtained from a subject, analysing the sample for the presence of (i) citrullinated tenascin-C and/or one or more fragments of citrullinated tenascin-C; and/or (ii) autoantibodies with specificity for citrullinated tenascin-C and/or one or more fragments of citrullinated tenascin-C; and then emitting an external signal if (i) citrullinated tenascin-C and/or one or more fragments of citrullinated tenascin-C; and/or (ii) autoantibodies with specificity for citrullinated tenascin-C and/or one or more fragments of citrullinated tenascin-C, are detected in the sample. The external signal may be in the form of an audible noise, a visual change, a print out, a digital message to the user, an email to the user or a third party, or any other suitable signal.

In the methods, kits, assays or devices of the invention, detecting the presence or absence, or the level, of citrullinated tenascin-C and/or one or more fragments of citrullinated tenascin-C may comprise the detection of tenascin-C, or fragments thereof, comprising one or more specific citrullinated residue(s). The specific citrullinated residue(s) may be selected from any of the group comprising residues 50, 51, 55, 72, 120, 169, 173, 209, 214, 219, 220 and 222; or combinations thereof (residue numbers as determined from SEQ ID NO: 70). Alternatively, the specific citrullinated residue(s) may be selected from any of the group comprising residues 55, 72, 120, 169, 173, 209, 214, 219, and 220; or combinations thereof (residue numbers as determined from SEQ ID NO: 70). The specific citrullinated residues may comprise CIT55, CIT209, CIT214, CIT219 and/or CIT220. The specific citrullinated residue may comprise CIT50. The specific citrullinated residue may comprise CIT51. The specific citrullinated residue may comprise CIT55. In another embodiment, the specific citrullinated residues may comprise CIT209 and/or CIT214. Alternatively, the specific citrullinated residues may comprise CIT219 and/or CIT220. The specific citrullinated residue may comprise CIT222. The specific citrullinated residues may be detected in the form of epitopes. For example, the method may comprise the detection of an epitope, wherein the epitope comprises at least one citrullinated residue selected from CIT55, CIT209, CIT214, CIT219 and CIT220; or combinations thereof. The epitope may comprise at least one citrullinated residue selected from CIT50, CIT51, CIT55, CIT209, CIT214, CIT219, CIT220 and CIT222; or combinations thereof. The epitope may comprise citrullinated residue CIT50. The epitope may comprise citrullinated residue CIT51. The epitope may comprise citrullinated residue CIT55. The epitope may comprise citrullinated residue CIT209. The epitope may comprise citrullinated residue CIT214. The epitope may comprise citrullinated residue CIT219. The epitope may comprise citrullinated residue CIT220. The epitope may comprise citrullinated residue CIT222.

In the methods, kits, assays or devices of the invention, detecting the presence or absence, or the level, of autoantibodies with specificity for citrullinated tenascin-C and/or one or more fragments of citrullinated tenascin-C may comprise the detection of autoantibodies having specific affinity for an epitope comprising one or more specific citrullinated residue(s). The specific citrullinated residue(s) may be selected from any of the group comprising residues 50, 51, 55, 72, 120, 169, 173, 209, 214, 219, 220 and 222; or combinations thereof (residue numbers as determined from SEQ ID NO: 70). Alternatively, the specific citrullinated residue(s) may be selected from any of the group comprising residues 55, 72, 120, 169, 173, 209, 214, 219, and 220; or combinations thereof (residue numbers as determined from SEQ ID NO: 70). The specific citrullinated residues may comprise CIT55, CIT209, CIT214, CIT219 and/or CIT220. The specific citrullinated residue may comprise CIT50. The specific citrullinated residue may comprise CIT51. The specific citrullinated residue may comprise CIT55. In another embodiment, the specific citrullinated residues may comprise CIT209 and/or CIT214. Alternatively, the specific citrullinated residues may comprise CIT219 and/or CIT220. The specific citrullinated residue may comprise CIT222.

The skilled man will appreciate that preferred features of any one embodiment and/or aspect of the invention may be applied to all other embodiments and/or aspects of the invention.

Definitions

By "inflammation" we include the meaning of local accumulation of fluid, plasma proteins, and white blood cells that is initiated by tissue injury, infection or a local immune response.

By "acute inflammation" we include the meaning of the initial stages (initiation) of inflammation and the short-term transient inflammatory response immediately after injury, infection or local immune response. Typically, acute inflammation is rapidly resolved, lasting from a matter of minutes to no longer that a few days.

By "chronic inflammation" we include the meaning of persistent and/or non-resolved inflammation. It is often associated with inappropriate destruction of healthy tissue. This may be progressive and last over a period of weeks or longer. Chronic inflammation is typically associated with persistent infection or disease including, but not limited to, autoimmune conditions.

By "chronic joint inflammation" we include the meaning of persistent inflammation that is progressive and unremitting over a period of weeks to months, resulting in distortion of the affected joint and radiographic evidence of cartilage and bone destruction as observed in human disease (Kelly, Harris, Ruddy and Sledge, Textbook of Rheumatology 4th Edition).

In experimental murine models, chronic joint inflammation is characterised by inflammation that does not subside and causes inappropriate tissue destruction, even over a relatively short period of time. This is characterized (and can be identified) histologically by the prolonged presence of inflammatory cells in the synovium and joint space, chondrocyte death, and cartilage and bone erosion.

By an "agent" we include all chemical entities, for example oligonucleotides, polynucleotide, polypeptides, peptidomimetics and small compounds.

By "citrullinated" we mean the conversion of one or more arginine amino acids in a protein into the amino acid citrulline.

By "a fragment of citrullinated tenascin-C" or "one or more fragments of citrullinated tenascin-C" we mean a citrullinated peptide or domain derived from citrullinated tenascin-C. The fragment of citrullinated tenascin-C may be a citrullinated FBG domain, a citrullinated TA domain, a citrullinated EGF-L domain, a citrullinated TNIII domain or any other sequence from within citrullinated tenascin-C. Preferably the fragment of citrullinated tenascin-C is antigenic. Preferably the fragment of citrullinated tenascin-C is biologically active.

By "fragment" we mean at least 10 nucleotides, for example at least 15, 16, 17, 18, 19, 20, 21, 22, 23, 24 or 25 nucleotides.

By "variant" we mean that the nucleotide sequence shares at least 90% sequence identity with the full length sequence of interest, for example at least 50%, 55%, 60%, 65%, 70%, 75%, 80%, 85%, 90%, 95%, 96%, 97%, 98% or 99% sequence identity.

The percent sequence identity between two polynucleotides may be determined using suitable computer programs, for example the GAP program of the University of Wisconsin Genetic Computing Group and it will be appreciated that percent identity is calculated in relation to polynucleotides whose sequences have been aligned optimally.

The alignment may alternatively be carried out using the Clustal W program (as described in Thompson et al., 1994, *Nuc. Acid Res.* 22:4673-4680). The parameters used may be as follows:

Fast pairwise alignment parameters: K-tuple (word) size; 1, window size; 5, gap penalty; 3, number of top diagonals; 5. Scoring method: x percent.

Multiple alignment parameters: gap open penalty; 10, gap extension penalty; 0.05.

Scoring matrix: BLOSUM.

Alternatively, the BESTFIT program may be used to determine local sequence alignments.

By "antibody" we include substantially intact antibody molecules, as well as chimeric antibodies, humanised antibodies, human antibodies (wherein at least one amino acid is mutated relative to the naturally occurring human antibodies), single chain antibodies, bispecific antibodies, antibody heavy chains, antibody light chains, homodimers and heterodimers of antibody heavy and/or light chains, and antigen binding fragments and derivatives of the same.

By "autoantibody" we mean any antibody manufactured by a subject's immune system that is directed against one or more of the subject's own proteins.

An "autoantigen" is an endogenous antigen that stimulates the production of autoantibodies.

By "antigen-binding fragment" we mean a functional fragment of an antibody that is capable of binding to citrullinated tenascin-C.

The term "subject" means all animals including humans. Examples of subjects include humans, cows, dogs, cats, goats, sheep, and pigs. The term "patient" means a subject having a disorder in need of treatment.

A 'therapeutically effective amount', or 'effective amount', or 'therapeutically effective', as used herein, refers to that amount which provides a therapeutic effect for a given condition and administration regimen. This is a predetermined quantity of active material calculated to produce a desired therapeutic effect in association with the required additive and diluent, i.e. a carrier or administration vehicle. Further, it is intended to mean an amount sufficient to reduce and most preferably prevent, a clinically significant deficit in the activity, function and response of the host. Alternatively, a therapeutically effective amount is sufficient to cause an improvement in a clinically significant condition in a host. As is appreciated by those skilled in the art, the amount of a compound may vary depending on its specific activity. Suitable dosage amounts may contain a predetermined quantity of active composition calculated to produce the desired therapeutic effect in association with the required diluent. In the methods and use for manufacture of compositions of the invention, a therapeutically effective amount of the active component is provided. A therapeutically effective amount can be determined by the ordinary skilled medical or veterinary worker based on patient characteristics, such as age, weight, sex, condition, complications, other diseases, etc., as is well known in the art.

Examples embodying an aspect of the invention will now be described with reference to the following figures:

FIG. 1. Accelerated resolution of acute inflammation in tenascin-C deficient mice.

(a) Paw swelling in wild type (+/+)(white bars) and tenascin-C null (−/−)(black bars) mice over time after injection of zymosan. Data are shown as the mean increase in paw diameter compared to paw diameter before injection+/− SEM (n=24 mice per genotype). **=p<0.01. (b-e) Representative sections of the ankle joint from wild type (b, c) and tenascin-C null (d, e) mice 4 days after zymosan injection, stained with hemotoxylin and eosin (b, d) and safranin-O (c, e). Boxes highlight the joint synovium (s) and cartilage proteoglycan (cp). Magnification ×10. Quantification of joint inflammation (f) and chondrocyte death (g) in knee joints 4 days after injection with zymosan from wild type mice (white bars) and tenascin-C null mice (black bars). Data are expressed as the mean (+/−SD) (n=24 mice per genotype). *=p<0.05.

FIG. 2. Synovial inflammation is induced in tenascin-C deficient mice upon injection of antigen.

(a-b, g) Representative sections of the knee joint of sham injected wild type mice. (c-f, h-i) Representative sections of the knee joint of wild type (c, d, h) or tenascin-C null (e, f, i) mice 24 hours after intra-articular injection of mBSA. Inflammatory cell infiltration in the capsule, meniscus and the joint space of both wild type and tenascin-C null mice is highlighted by (cap), (M) and (J) respectively. (S) highlights the healthy synovium of sham injected mice that is no more than 1-3 cells thick along the entire bone surface and (ST) highlights the synovia of wild type and tenascin-C null mice which are both significantly thickened. Sections are stained with hemotoxylin and eosin (a, c, e, g, h, i) and safranin-O (b, d, f). Magnification ×10 (a-f) or ×40 (g-i). (n=5 mice per genotype).

FIG. 3. Synovial inflammation subsides rapidly in tenascin-C deficient mice.

Representative sections of the knee joint of wild type (a, b, f) or tenascin-C null (c, d, e) mice 3 days after intra-articular injection of mBSA. (a, c) The line highlights increased inflammation of the capsule in wild type mice compared to tenascin-C null mice. (b, d) (cp) highlights increased cartilage proteoglycan loss in wild type mice compared to tenascin-C null mice. (e, f) Significant synovial hyperplasia (line), cell and fibrin deposits in the joint space (arrow) and pannus invasion (arrow heads) are observed in wild type mice compared to tenascin-C null mice. Sections are stained with hemotoxylin and eosin (a, c, e, f) and safranin-O (b, d) Magnification ×10 (a-d) or ×20 (e-f). (n=5 mice per genotype).

FIG. 4. tenascin-C deficient mice are protected from tissue destruction during antigen induced arthritis.

(a-b) Representative sections of the knee joint of wild type mice 7 days after intra-articular injection of mBSA, stained with hemotoxylin and eosin (a) and safranin-O (b). Magnification ×10. (n=24 mice per genotype). Arrowhead highlights area of bone erosion. Arrow highlights pannus invasion into articular cartilage. (c-d) Representative sections of the knee joint of tenascin-C null type mice 7 days after intra-articular injection of mBSA, stained with hemotoxylin and eosin (c) and safranin-O (d). Magnification ×10. (n=24 mice per genotype). J highlights the joint space and AC the intact articular cartilage. (e) Histological score of knee joint inflammation 24 hours, 3 days and 7 days after injection with mBSA from wild type mice (white bars) and tenascin-C null mice (black bars). Data represent the mean+/−SD (n=5 per genotype (24 h, 3d) or 24 per genotype (7d)). (f) Quantification of chondrocyte death, cartilage surface erosion and bone erosion after injection with mBSA in knee joints from wild type mice (white bars) and tenascin-C null mice (black bars). Chondrocyte death is shown at 24 hours, 3 days and 7 days, and cartilage surface erosion and bone erosion at 7d. Data represent the mean+/−SD (n=5 per genotype (24 h, 3d) or 24 per genotype (7d)).

FIG. 5. tenascin-C induces TNF-α, IL-6 and IL-8 synthesis in primary human macrophages and RA synovial fibroblasts.

(a-b) Primary human macrophages (a) and RA synovial fibroblasts (b) were unstimulated (no addition) or stimulated with LPS (1 ng/ml (a) or 10 ng/ml (b)) or recombinant tenascin-C (1.0 µM) for 24 h. Data shown are the mean of triplicate values (+/−SD) from one of three representative experiments. (c) Primary human macrophages were unstimulated (no addition) or stimulated with LPS (1 ng/ml) or recombinant tenascin-C (1.0 µM) for 24 h. (−) indicates cells were pre-incubated with medium alone. (P) Cells were pre-incubated with 25 µg/ml polymyxin B for 30 min before stimulation. (H) Cells were incubated with medium with no addition or containing LPS or tenascin-C that was boiled for 15 minutes before addition to cells. Data shown are the mean of triplicate values (+/−SD) from one of three representative experiments.

FIG. 6. The FBG domain of tenascin-C mediates stimulation of cytokine synthesis in vivo and in vitro.

(a) Primary human macrophages were unstimulated (no addition) or stimulated with LPS (1 ng/ml), recombinant tenascin-C (TNC) or 1.0 µM tenascin-C domains (TA, EGF-L, TNIII-5, TNIII-3, TNIII3-5, TNIII5-7, TNIII6-8 and FBG) for 24 h. Data shown are the mean of triplicate values (+/−SD) from one of three representative experiments. (b) RA synovial membrane cells were unstimulated (no addition) or stimulated with LPS (10 ng/ml) or recombinant FBG (1.0-0.01 µM) for 24 h. Data shown are the mean % change in cytokine levels compared to unstimulated cells (+/−SEM) from five different patients. (c-h) Representative sections of the knee joint of wild type mice 3 days after intra-articular injection of PBS (c-e) or 1 µg FBG (f-h). Sections are stained with hemotoxylin and eosin (c,d,f,g) or Safranin-O (e, h). Magnification ×10 (c, f) or ×25 (d,e,g,h) (n=5 mice per genotype). (i) Quantification of joint inflammation, bone erosion, cartilage surface erosion and chondrocyte death in the knee joints of wild type mice 3 days after intra-articular injection of PBS (black bars) or 1 µg FBG (white bars). Data represent the mean+/−SD (n=5 per genotype).

FIG. 7. FBG mediated cytokine synthesis is MyD88 dependent.

(a) Human RA synovial fibroblasts were either uninfected, infected with adenovirus expressing GFP alone (AdGFP) or infected with adenovirus expressing dominant negative MyD88 (AdMyD88dn). Cells were unstimulated, stimulated with LPS (10 ng/ml) or stimulated with FBG (1 µM) for 24 h. Data shown are the mean of three independent experiments (+/−SEM). (b) Mouse embryonic fibroblasts isolated from wild type (+/+) or MyD88 deficient (−/−) mice were unstimulated (−) or stimulated with PAM3 (100 ng/ml), LPS (100 ng/ml), TNFα (100 ng/ml), IL-1 (5 ng/ml) and FBG (1 µM) for 24 h. Data shown are the mean of three independent experiments (+/−SEM).

FIG. 8. FBG mediated cytokine synthesis is TLR4 dependent but does not require CD14 or MD-2.

(a) Primary human macrophages were pre-incubated with medium alone or medium containing function blocking antibodies to TLR2 (10 µg/ml), TLR4 (25 µg/ml) or isotype control antibodies (25 µg/ml) for 30 min before stimulation. Cells were unstimulated, or stimulated with LPS (1 ng/ml), FBG (1 µM) or PAM3 (10 ng/ml) for 24 h. Data shown are the mean of three independent experiments (+/−SEM). (b) Mouse embryonic fibroblasts isolated from wild type, TLR2 (TLR2 −/−) or TLR4 (TLR4 −/−) deficient mice were unstimulated or stimulated with PAM3 (100 ng/ml), LPS (100 ng/ml), IL-1 (5 ng/ml) and FBG (1 µM) for 24 h. Data shown are the mean of three independent experiments (+/−SEM). (c) Bone marrow derived macrophages isolated from wild type, TLR2 (TLR2 −/−) or TLR4 (TLR4 −/−) deficient mice were unstimulated or stimulated with PAM3 (100 ng/ml), LPS (100 ng/ml) or FBG (1 µM) for 24 h. Data shown are the mean of three independent experiments (+/−SEM). (d) Human macrophages were pre-incubated with no inhibitor, 1 µg/ml msbB LPS or 10 µg/ml anti-CD14 antibody for 30 min before stimulation with LPS (1 ng/ml), FBG (1 µM) or PAM3 (10 ng/ml) for 24 h. Data shown are the mean of three independent experiments (+/−SEM).

FIG. 9. Paw swelling over time after injection of zymosan.

Representative images of the paws of non-injected tenascin-C null mice (a, e) (diameter 1.6 mm), tenascin-C null mice 24 h (d, f) (diameter 2.5 mm) and 4d (b, h) (diameter 1.7 mm) after zymosan injection and from wild type mice 4d after zymosan injection (c, g) (diameter 2.1 mm).

FIG. 10. Synthesis of recombinant proteins.

(a) Domain structure of the tenascin-C monomer comprising different domains, including the assembly domain (TA), 14 and a half EGF-like repeats (EGF-L), 17 fibronectin type III-like repeats (TNIII) (8 constitutively expressed (1-8) and 9 that can be alternatively spliced, and a fibrinogen-like globe (FBG). (b) The regions covered by the recombinant proteins that were synthesized, the corresponding amino acid residues and the molecular weight of each protein.

FIG. 11. Analysis of protein purity.

Silver stained gel showing 1 μg of each recombinant protein analysed by SDS-PAGE under reducing conditions. Lanes: 1 (TA), 2 (EGF-L), 3 (TNIII-5), 4 (TNIII5-7), 5 (TNIII6-8), 6 (TNIII-3), 7 (TNIII3-5) and 8 (FBG).

FIG. 12. FBG-mediated joint inflammation in vivo requires expression of TLR4.

Representative sections of the knee joint of TLR2 (a) and TLR4 (b) null mice 3 days after intra-articular injection of 1 μg FBG. Sections are stained with hemotoxylin and eosin. Magnification ×10 (n=5 mice per genotype). (c) Quantification of joint inflammation, bone erosion, cartilage surface erosion and chondrocyte death in the knee joints of TLR2 (white bars) and TLR4 (black bars) null mice 3 days after intra-articular injection of 1 μg FBG. Data represent the mean+/−SD (n=5 per genotype).

FIG. 13. Amino acid sequence of human tenascin-C and its domains [SEQ ID NOs 65-67]

FIG. 14. Nucleotide sequence of human tenascin-C [SEQ ID NO: 68]

FIG. 15. TNF synthesis in response to specific FBG peptides.

TNF synthesis by RA membrane cultures incubated for 24 h with no addition or 100 μM of each FBG peptide (P1, P3-P9).

FIG. 16. TNF and IL8 synthesis in response to varying concentrations of specific FBG peptides.

TNF and IL8 synthesis by RA membrane cultures incubated for 24 h with no addition or 25, 100 or 250 μM of FBG peptide.

FIG. 17. IL8 synthesis in response to LPS, whole FBG domain or specific FBG peptides.

IL8 synthesis by macrophages after 24 h incubation with no addition, 1 ng/ml LPS, 1 μM whole FBG domain (FBG) or 1 or 20 μM of FBG peptides (P1, P3-P9).

FIG. 18. IL8 and TNF synthesis in response to LPS and FBG following pre-incubation with FBG peptides.

TNF and IL8 synthesis by macrophages after 24 h incubation with no addition, 1 ng/ml LPS or 1 μM whole FBG domain (FBG), either with or without pre-incubation with 20 μM of FBG peptides.

FIG. 19. IL8 and TNF synthesis in response to tenascin-C targeted siRNAs.

Tenascin-C mRNA levels in RA fibroblasts transfected with luciferase specific siRNA (control), or with tenascin-C targeted siRNAs: oligo 1 (si 1), oligo 2 (si 2) or a combination of oligos 1+2 (si 1+2). IL6 synthesis in RA fibroblasts transfected with luciferase siRNA (control) or with a combination of tenascin-C targeted oligos 1+2 (siRNA) in the presence or absence of 10 ng/ml LPS for 24 h.

FIG. 20. Purified fibrinogen and FBG can be citrullinated in vitro

Coomassie stained gel showing purified fibrinogen (lanes 2-5) and FBG (lanes 6-9) that have been left unmodified (lanes 2, 6) or citrullinated by incubation with citrullination buffer, PAD and CaCl (lanes 3, 7). Citrullination of fibrinogen was confirmed by the observation of an increase in MW of this protein. However, changes in the size of FBG were less apparent. Incubation of proteins with PAD in the absence of CaCl or with CaCl in the absence of PAD had no effect on protein size (lanes 4, 5 and 8, 9).

FIG. 21. Purified full length tenascin-C can be citrullinated in vitro

Coomassie stained gel showing purified full length tenascin-C that has been left unmodified (lane 9) or citrullinated by incubation with citrullination buffer, PAD and CaCl (lane 6). Citrullination of tenascin-C was confirmed by the observation of an increase in MW of this protein. Incubation of tenascin with PAD in the absence of CaCl or with CaCl in the absence of PAD had no effect on protein size (lanes 7,8). Purified fibronectin was included as a loading control (lane 2).

FIG. 22. Western blot confirmation of citrullination of FBG and tenascin-C

Western blot of native and citrullinated tenascin-C (lanes 8, 9) and native and citrullinated FBG (lanes 4, 5) probed using the AMC detection kit. Native and citrullinated fibronectin (lanes 2, 3), native and citrullinated fibrinogen (lanes 6,7) and native and citrullinated enolase (lanes 11,10) were included as positive controls known to be citrullinated.

FIG. 23 FBG is citrullinated by PAD in vitro

Purified recombinant FBG was citrullinated in vitro by incubating with different concentrations (2, 7 and 20 Units per mg protein) of rabbit PAD2, human PAD2 and human PAD4 in citrullination buffer (100 mM Tris pH 7.4, 10 mM $CaCl_2$, 5 mM DTT) for 3 h, 8 h and 24 h at 37° C. As a negative control FBG-C was incubated in citrullination buffer without Calcium (—$Ca^{2+}$) or without enzyme (—PAD). (A) 1 ug of each sample were resolved on SDS-PAGE and stained with Coomassie Blue. FBG citrullinated by PAD migrates at a slightly higher molecular weight than non-citrullinated FBG. (B) Proteins were transferred on nitrocellulose membranes and incubated in a chemical modification mix (0.0125% $FeCl_3$, 2.3M $H_2SO_4$, 1.52 M $H_3PO_4$, 0.25 M Acetic Acid, 0.25% 2, 3-butanedione monoxime, 0.125% antipyrine). Citrullinated proteins were detected with an anti-modified citrulline specific antibody.

FIG. 24. Citrullination enhances cytokine production stimulated by FBG

TNF synthesis in primary human macrophages left unstimulated (UN) or stimulated with 0.1-1.0 μM non-citrullinated (nFBG) or citrullinated (cFBG) FBG. Citrullination buffer alone (CIT) and buffer with PAD (CIT+PAD) were included as controls. FBG incubated with citrullination buffer in the absence of PAD or with PAD in the absence of calcium was not citrullinated and exhibited no enhancement of cytokine synthesis (not shown).

FIG. 25. Ten of 50 RA patients (20%) and none of 50 controls react with citrullinated tenascin-C by Western blot.

(A) Coomassie stained gel of native (nTNC) and citrullinated (cTNC) purified human recombinant tenascin-C (top panel). Citrullination of tenascin-C demonstrated by western blot with the AMC (Anti-modified citrulline) kit (bottom panel). (B) Representative western blot of cTNC probed with serum from RA patients (RA) or normal healthy controls (NH) (n=50). No reactivity was observed with any sera in blots of nTNC (not shown).

FIG. 26. Serum from a subset of RA patients exhibits reactivity with citTNC

Western blot of cTNC probed with serum from 7 different RA patients showing one positive patient (lane 4).

FIG. 27. Serum from a subset of RA patients exhibits reactivity with citTNC

Western blot of cTNC probed with serum from 8 further RA patients showing one positive patient (lane 4).

FIG. 28. Serum from normal healthy controls exhibit no reactivity with citTNC

Western blot of cTNC probed with serum from 8 different controls showing no positive patients.

FIG. 29. Shows RA serum against citrullinated tenascin-C plus citrullinated FBG

Western blot of cTNC plus cFBG run together in the same well, probed with serum from 7 different RA patients. Patient subsets were observed that reacted with full length tenascin-C (320 kD) but not FBG (lanes 4, 5) or patients that reacted with cit FBG (27 kd) but not full length tenascin-C (lane 6).

FIG. 30 Defining the sites of citrullination by LC-MS/MS (A) Arginine residues citrullinated by rPAD2 (circle), hPAD2 (rectangle) and hPAD4 (triangle) were determined by LC-MS/MS. Citrullinated sites are underlinded, non-citrullinated sites are dashed-underlined, and sites that were not covered by the LC-MS/MS analysis are marked with *. (B) Sequence of FBG domain. All arginine residues are shown, arginine residues that were modified to citrulline residues are underlined. Arginines marked with * were not covered by the LC-MS/MS analysis.

FIG. 31 Identifying the citrullinated antibody epitope (A) Peptides with sequences corresponding to the amino acid sequence of FBG were designed, with the addition of cysteine residues at the amino and carboxy termini and the exchange of arginine for citrulline residues at positions identified by LC-MS/MS. (B) IgG response to citrullinated FBG peptides and arginine containing control peptides in patients with rheumatoid arthritis (RA; n=20) and healthy controls (n=20). The 95th percentile of the control sera was used to determine positivity (dashed line). Mann-Whitney U test was used to calculate p values for differences between groups (n.s.=no significant difference, *=$p<0.05$ and =$p<0.01$, *=$p<0.001$, ****=$p<0.001$).

FIG. 32 Citrullination of FBG reduces cell adhesion of HDF and RAF (A) The sequence identified to bind integrin $\alpha v \beta 3$ is shown in white (Yokoyama et al., 2000). Within this sequence two Arginines (shown in black) were identified to be citrullinated. (B) Wells of a 96 well plate were coated with different concentrations of FBG, citrullinated FBG (cFBG), FBG incubated in buffer without Calcium (FBG —$Ca^{2+}$), or FBG incubated without PAD (FBG —PAD). As a positive control wells were coated with Fibronectin (FN) (1 ug/ml), and coating with BSA (10 mg/ml) served as negative control. Plates were incubated with human dermal fibroblasts (HDF) or synovial fibroblasts from RA patients (RAF) for 45 minutes and adhesion was measured by determining absorbance of attached cells after staining with crystal violet (0.1%). Data are shown as the mean of at least four independent experiments+s.e.m., *=$p<0.05$, **=$p<0.01$.

EXAMPLE 1

General Methods

Reagents

Zymosan, methylated BSA and Freund's complete adjuvant, anti-FLAG M2 antibody (mouse monoclonal antibody), blasticidin, and isotype control antibodies (Mouse IgG2a, IgG1) were from Sigma-Aldrich (Dorset, UK). Hypnorm was from VetaPharma Ltd. (Leeds, UK). The Limulus amaebocyte lysate assay was from Associates of Cape Cod (Liverpool, UK). Wild type human embryonic kidney (HEK293-EBNA) cells were from Invitrogen (Groningen, Netherlands). M-CSF and murine IL-1β were from Pepro-Tech (Neuilly-Sur-Seine, France). DMEM, RPMI 1640, fetal bovine serum (FBS), penicillin/streptomycin, antibiotic-antimycotic solution PSA and β-Mercaptoethanol were from PAA Laboratories (Yeovil, UK). HEK293 cell lines stably expressing human TLR2 and TLR4/CD14/MD-2, polymyxin B, msbB LPS and the function blocking TLR2 (Clone: TL2.1 Isotype: Mouse IgG2a) and TLR4 antibodies (Clone: HTA125 Isotype: Mouse IgG2a) were from Invivogen (Caine, UK). Phenol-chloroform-purified *Escherichia coli* LPS (rough and smooth) and Pam3Cys-Ser-Lys4 (Pam3C) were from Alexis (Birmingham, UK). Murine TNF-α and IL-1 receptor antagonist (IL-1ra-IL-1F3) were from R&D Systems (Abingdon, UK). Function blocking anti-CD14 antibodies (Isotype: Mouse IgG1) were from Abcam (Cambridge, UK). Human and murine TNF-α, IL-6, and IL-8 ELISAs were from Pharmingen (Oxford, UK).

Purification of Full-Length Tenascin-C

To ensure that cytokine production was not attributed to bacterial contaminants such as LPS and LPS-associated molecules we purified recombinant full-length human tenascin-C from the conditioned medium of the mammalian cell line HEK293 transfected with his-tagged human tenascin-C in the pCEP-pu vector as described (Lange (2007)). tenascin-C was purified to homogeneity as described (Lange (2007) and determined to be free of LPS contamination using the Limulus amaebocyte lysate assay according to the manufacturer's instructions.

Synthesis of Recombinant Proteins

Proteins corresponding to each domain of tenascin-C were synthesized (TA, EGF-L, various TNIII repeats and FBG) and purified. See Example 2.

Measurement of LPS Contamination in Recombinant Proteins

To ascertain the levels of LPS in each recombinant protein the Limulus amaebocyte lysate assay was used according to the manufacturer's instructions (sensitivity ~0.7±0.5 pg LPS per mg protein). All recombinant proteins used in this study had levels of LPS that were less than 10 μg/ml.

Adenoviral Vectors and their Propagation

Recombinant, replication-deficient adenoviral vectors encoding wild type MyD88 (AdMyD88 wt), dominant-negative forms of MyD88 (AdMyD88dn) and the GFP control (AdGFP) were constructed in-house. A description of the synthesis of these viruses is in Andreakos (2004). All viruses used in this study are E1/E3 deleted, belong to the Ad5 serotype. Viruses were propagated in 293 human embryonic kidney cells, purified by ultracentrifugation through two caesium chloride gradients, and viral titres determined by plaque assay as previously described (Sacre (2007)).

Animals

Homozygous tenascin-C deficient mice from the original stock described by Saga (1992) on a 129/sv an inbred strain of mice with a white bellied and agouti appearance background were provided by Prof. Charles French-Constant (University of Edinburgh, UK). Age matched congenic inbred wild type 129/sv mice were obtained from Charles River (Margate, UK). All tenascin-C deficient and wild type 129/sv mice were male and between 8-10 weeks of age at the time of experimentation.

Homozygous TLR2 and TLR4 deficient mice on a C57BL/6 background (an inbred strain of mice with a black coat) were obtained from B&K Universal (Hull, UK) Hoshino (1999) and Takeuchi (1999). Homozygous MyD88 deficient mice on a C57BL/6 background were provided by the Sanger Institute (Cambridge, UK). Age matched congenic inbred wild type C57B/L6 mice were obtained from Charles River (Margate, UK). For isolation of mouse embryo fibroblasts one female aged 8-10 weeks was mated with two males aged 8-10 weeks. For isolation of bone marrow derived macrophages mice were female and between 10-12 weeks of age at the time of experimentation.

All animals were fed standard rodent chow and water ad libitum, and were housed (<6 mice/cage) in sawdust-lined cages in an air-conditioned environment with 12-hour light/dark cycles. All animal procedures were approved by the institutional ethics committee.

Statistical Methods

Mean, SD, SEM, and statistical tests were calculated using GraphPad version 3 (GraphPad Software Inc., San Diego, Calif.). Multiple group means were analyzed by one-way analysis of variance, followed by the Dunnett Multiple Comparisons test, where appropriate. Unpaired t-test was used for experiments involving only two groups.

EXAMPLE 2

Synthesis of Recombinant Proteins

Proteins corresponding to each domain of tenascin-C were synthesized (TA, EGF-L, various TNIII repeats and FBG) and purified. The recombinant proteins synthesized are depicted in FIG. 9.

Reagents

Pfu Turbo polymerase was from Stratagene (Amsterdam, Netherlands). Easy mix 50 PCR tubes were from Molecular Bioproducts (Lutterworth, UK). RNeasy kits and $Ni^{2+}$-NTA-agarose columns were from Qiagen (Crawley, UK). pCR Blunt vector, pCEP4 plasmid vector, human embryonic kidney (HEK293-EBNA) cells and 4-12% Bis-Tris gradient gels were from Invitrogen (Groningen, Netherlands). pET32b vector and BL21 (DE3) Rosetta cells were from Novagen (Kent, UK). HiTrap Q columns, HiTrap S columns, Sephacryl S500 HR column and heparin sepharose columns were from Amersham (Buckinghamshire, UK).

Restriction enzymes were obtained from New England BioLabs (Hitchin, UK). DMEM, foetal bovine serum (FBS) and penicillin/streptomycin were from PAA laboratories (Yeovil, UK). FuGENE6 transfection reagent was from Roche Applied Science (Basel, Switzerland).

Anti-FLAG M2 antibody (mouse monoclonal antibody), anti-FLAG M2-agarose, FLAG peptide were from Sigma-Aldrich (Dorset, UK). Anti-tetra-his antibody (mouse monoclonal antibody) was from Qiagen (Crawley, UK). Alkaline phosphatase-conjugated goat anti-(mouse IgG) IgG and Western Blue stabilized substrate for alkaline phosphatase were from Promega (Southampton, UK). Precision Protein Standards for SDS-PAGE were from BioRad (Hemel Hempstead, UK).

Primer Design

Domain boundaries were determined using alignments published in the human tenascin-C sequence (Siri (1991) accession number P24821 (Swiss-Prot)). To clone each domain we designed PCR primers where both the forward and reverse primers contained 18-21 bases corresponding to the 5' and 3' terminal sequences of the requisite coding sequence. The forward primer contained an Nde1 restriction site, followed by an N terminal his tag, immediately before the coding sequence. The final 3 bases of the Nde1 site form the ATC methionine initiation code. The reverse primer included a TTA stop codon immediately after the coding sequence, followed by a BamH1 or a Kpn1 site to allow unidirectional cloning into pET32b expression vectors.

TABLE 1

| Protein name | Forward primer Reverse primer |
|---|---|
| TA | FW: ATA*CATATG*CATCATCATCATCATCATGGGGTCCTCAAG AAAGTCATCCGG [SEQ ID NO: 1]<br>RV: GCC*GGATCC*TTAGCCTGCTCCTGCAGTACATTG [SEQ ID NO: 2] |
| EGF-L | PCR1<br>FW: ACAGT*GGTACC*ACCATGGGGGCCATGGGGGCCATGACT CAGCTGTTG [SEQ ID NO: 3]<br>RV: *CTTGTCATCGTCGTCCTTGTAGTCAC*CTTCGGTAGCGAG GGCAAG [SEQ ID NO: 4]<br><br>PCR2<br>FW: *GACTAGAAGGACGACGATGACAAG*TGCTGTCTCCAGCC TGCCAC [SEQ ID NO: 5]<br>RV: GACAGC*GGATCC*TTAATGATGATGATGATGATGTGAGCA GTCTTCTCCGCTGTAGC [SEQ ID NO: 6] |
| TN1-5 | FW: ATA*CATATG*CATCATCATCATCATCATGAGGTGTCTCCTCC CAAAGA [SEQ ID NO: 7]<br>RV: GCC*GGTACC*TTAAGTGGATGCCTTCACACGTGC [SEQ ID NO: 8] |
| TN1-3 | FW: ATA*CATATG*CATCATCATCATCATCATGAGGTGTCTCCTC CCAAAGA [SEQ ID NO: 9]<br>RV: GCC*GGTACC*TTATGTTGTGAAGGTCTCTTT GGC [SEQ ID NO: 10] |
| TN3-5 | FW: ATA*CATATG*CATCATCATCATCATCATCGCTTGGATGCC CCCAGCCAGAT [SEQ ID NO: 11]<br>RV: GCC*GGTACC*TTAAGTGGATGCCTTCACACGTGC [SEQ ID NO: 12] |

TABLE 1-continued

| Protein name | Forward primer Reverse primer |
|---|---|
| TN5-7 | FW: ATA*CATATG*CATCATCATCATCATCATGAGTTGGACACG CCCAAGGAC [SEQ ID NO: 13]<br>RV: GCC*GGATCC*TTATGTTGTGAACTTGGCAGTGATGGTTG [SEQ ID NO: 14] |
| TN6-8 | FW: ATA*CATATG*CATCATCATCATCATCATGCCATGGGCTCCCC AAAGGAA [SEQ ID NO: 15]<br>RV: GCC*GGATCC*TTATGTGGTGAAGATGGTCTGGATCAT [SEQ ID NO: 16] |
| FBG | FW: ATA*CATATG*CATATGCATCATCATCATCATCATATTGGACTCCTGTAC CCCTTCC [SEQ ID NO: 17]<br>RV: GCC*GGATCC*TTATGCCCGTTTGCGCCTGCCT TCAA [SEQ ID NO: 18] |

All primers above are written 5' to 3'. Flag sequences are in bold, His tags (CATCATCATCATCATCAT [SEQ ID NO: 19]) are underlined, and restriction enzyme cleavage sites (CATATG=NdeI site, GGATCC=BamH1, GGTACC=Kpn1 site) are in bold italics.

PCR

PCR amplification was carried out using 10 pmol/µl of each primer, 1 µg template, 5 µl DMSO, and 1.25 units Pfu Turbo polymerase in a final volume of 25 µl. This was added to buffer and dNTPs in Easy mix 50 tubes. The template used for all reactions was cDNA prepared from U87MG human glioma cells using RNA isolated with RNeasy kits. The reaction was cycled 40 times with denaturing, annealing and elongation temperatures of 95° C., 55-65° C. (depending on melting temperature (Tm) of primers) and 72° C. respectively.

Cloning

PCR products were ligated into pCR Blunt vectors and sequenced to ensure no errors had been introduced by PCR. Clones were selected that had no errors or silent mutations. Inserts were then ligated into pET32b using NdeI and BamH1 restriction sites engineered into primers (TN5-7 and TN6-8). Human tenascin-C has internal BamH1 sites within the TA domain (position 494) and TNIII2 (position 2509). TA and TN1-8 were therefore cloned using the NdeI site in the FW primer and the Kpn1 site in the cloning site of pCRBlunt. Human tenascin-C contains no internal Kpn1 sites. TN1-5, TN1-3 and TN3-5 were cloned using NdeI and Kpn1 sites in the primers. FBG contains an internal NdeI site (position 6439) and was therefore cloned using a two step ligation of NdeI and BamH1 digestion, followed by NdeI digestion. (Positions refer to sites within the full length nucleotide sequence of tenascin-C, given in FIG. 14).

Bacterial Growth, Induction and Lysis

The plasmids were transformed into BL21 (DE3) Rosetta cells, cultured in 3 L of Luria-Bertani medium containing 50 µg/ml carbenicillin and induced with 1 mM isopropyl-β-D-thiogalactopyranoside. After 3 hours, the cells were harvested by centrifugation at 4,000 rpm for 20 min, washed twice with ice-cold wash buffer (50 mM Tris-HCl, pH 8.0, 100 mM NaCl, and 1 mM EDTA), and lysed with a French press. Inclusion bodies were collected by centrifugation at 12,000 rpm for 20 min at 4° C. With the exception of TA and FBG the proteins were located entirely in the supernatant. Recombinant TA and FBG proteins were extracted from inclusion bodies with 6 M guanidine hydrochloride, 50 mM Tris-HCl, pH 8.0, and 10 mM β-mercaptoethanol at room temperature with constant stirring for 2 hours.

Purification of Bacterial Proteins

The solution containing recombinant protein was applied to a $Ni^{2+}$-NTA-agarose column and washed with 50 mM Tris-HCl, pH 8.0 containing 20 mM imidazole. The column was subsequently washed with 50 mM Tris-HCl, pH 8.0 and the protein was eluted with 50 mM Tris-HCl, pH 8.0 containing 60 mM imidazole. For TA and FBG each washing and elution buffer contained 6 M guanidine hydrochloride. Following Ni chromatography TA and FBG required no subsequent purification. TN1-3 and TN6-8 were further purified by anion exchange chromatography using a HiTrap Q column, TN1-5, TN3-5 and TN5-7 by cation exchange chromatography using a HiTrap S column, and TN1-8 using a HiTrap S column followed by gel filtration using a Sephacryl S500 HR column.

Refolding of Insoluble Proteins

TA and FBG were refolded by diluting to 20 µg/ml with 50 mM Tris-HCl, pH 8.0 containing 6 M guanidine hydrochloride and then treating with 20 mM cystamine with stirring for 16 hours at 4° C. The solution was then dialyzed twice against 15 volumes of 50 mM Tris-HCl, pH 8.0 containing 150 mM NaCl, 10 mM $CaCl_2$, 5 mM β-mercaptoethanol, and 1 mM 2-hydroxyethyl disulfide for 24 hours at 4° C., twice against 20 mM Tris-HCl, pH 8.0 for 8 hours at 4° C. and then centrifuged at 12,000 rpm for 30 min at 4° C. Refolding was assessed by size shifts using SDS PAGE under reducing and non reducing conditions. Protein activity was confirmed by TA domain polymerization and FBG binding to heparin sepharose columns.

Synthesis of EGF-L Domain Using Mammalian Cells

Initial attempts to express and purify the EGF-L repeats region using an *E. coli* expression system were unsuccessful. This is most likely to be attributable to difficulty in achieving protein folding due to a total of 91 cysteines in this region. Therefore, the EGF-like domains of TN-C were expressed using HEK293 cells.

Two PCR reactions were carried out. The first PCR product consisted of a restriction enzyme KpnI site, a Kozak sequence followed by the TN-C signal sequence. The second PCR product consisted of a FLAG peptide, the EGF-like domain sequence, followed by a histidine tag and a BamH1 restriction enzyme sequence.

The two PCR products were ligated together as described by Ho (1989). PCR reactions were carried out as described above. The entire construct was cloned into the PCR blunt vector and sequenced. It was then subcloned into the pCEP4 vector. The DNA was transfected into HEK293 cells using Fugene and cells were selected for hygromycin resistance (200 µg/ml) in Dulbecco's modified Eagle's medium (DMEM) containing 10% (v/v) fetal calf serum, penicillin (100 units/ml) and streptomycin (100 units/ml). 2 liters conditioned medium (collected after cells have been cultured in medium) from stably transfected cells was collected and pooled. The pooled conditioned medium (2 liters) was centrifuged at 3000 rpm to separate cell debris from the medium.

The medium was then applied to an anti-FLAG column. Material was collected in 50 ml fractions for the flow-through. The column was washed with 10 column volumes of 1M NaCl, 50 mM Tris-HCl, pH 7.5 and then washed with 10 column volumes of 60% isopropanol to ensure removal of LPS. The column was then washed with 50 mM Tris-HCl buffer, pH 7.5 and finally the protein was eluted using 200 µg/ml FLAG peptide in 50 mM Tris-HCl buffer, pH 7.5.

Analysis of Protein Purity

Each protein was dialysed against 1000 volumes of 150 mM NaCl and 50 mM Tris pH 7.5. Protein purity was analyzed by SDSPAGE under reducing conditions. To do this 1 µg of each purified recombinant protein was run on a 4-12% Bis-Tris gradient gel and the gel was subsequently silver stained to demonstrate a single band (FIG. 10). Western blotting analyses were also carried out. Proteins separated by SDS-PAGE were electrotransferred to polyvinylidene difluoride membranes. The membranes were blocked with 5% BSA in Tris-buffered saline and then incubated with primary antibodies recognizing FLAG M2 (1:2000 dilution)(EGF-L) or tetra-his antibodies (1:2000) (all other proteins). The blot was then incubated with secondary antibody conjugated to alkaline phosphatase and the protein bands visualized using Western Blue stabilized substrate whereby the gels show a single specific band recognised by each antibody at the expected Mw (not shown).

EXAMPLE 3

Animal Models

Zymosan-Induced Arthritis

Zymosan-induced arthritis (ZIA) was induced in tenascin-C deficient and wild type mice by injection of zymosan (*Saccharomyces cerevisiae*), as described in Keystone (1977). Zymosan was prepared by dissolving 15 mg of zymosan in 1 ml of sterile PBS. The solution was boiled twice and sonicated. Mice were anesthetized by intraperitoneal injection of 150 µl of Hypnorm diluted 1:10 in sterile water, then injected with zymosan (10 µl) into the right footpad (d=0).

Control mice received an injection of 10 µl PBS alone or were not injected. For macroscopic assessment of arthritis, the thickness of each hind paw was measured daily with microcalipers (Kroeplin, Schluchlem, Germany) and the diameter expressed as an average for each inflamed hind paw per mouse.

Following completion of the experiment (day=4), mice were euthanized and hind paws fixed in 10% (v/v) buffered formalin, decalcified with 10% EDTA and processed to paraffin.

Antigen-Induced Arthritis

Antigen-induced arthritis (AIA) was induced in tenascin-C-deficient and wild-type mice as described previously by Brackertz (1977). Briefly, at day 0 mice were anesthetized by intraperitoneal injection of 150 µl of Hypnorm diluted 1:10 in sterile water, then immunized with 200 µg of methylated BSA. mBSA was emulsified in 0.2 ml of Freund's complete adjuvant and injected intra-dermally at the base of the tail.

At day 7, arthritis was induced by intra-articular injection of mBSA (100 µg in 10 µl of sterile PBS) into the right knee joint using a sterile 33-gauge microcannula. Control mice received an injection of 10 l PBS alone or were not injected.

On day 14, mice were euthanized, the knee joints were excised and fixed in 10% (volume/volume) buffered formalin, decalcified, with 10% EDTA and processed to paraffin.

Injection of FBG

Wild type mice were anesthetized by intraperitoneal injection of 150 µl of Hypnorm diluted 1:10 in sterile water and then injected with 100 ng, 1 or 3 µg FBG in 10 µl of sterile PBS into the right knee joint using a sterile 33-gauge microcannula. Control mice received an injection of 10 µl PBS alone or were not injected.

On days 3 and 7, mice were euthanized, the knee joints were excised and fixed in 10% (volume/volume) buffered formalin, decalcified, with 10% EDTA and processed to paraffin.

Histology of Knee Joints

Coronal tissue sections (4 µm) were cut at 7 depths throughout the joint; 80 µm apart and stained with hematoxylin and eosin or Safranin-O to assess joint pathology. Histopathologic changes were scored using the following parameters as described in Van Lent (2006).

Inflammation (the influx of inflammatory cells into synovium (infiltrate) and the joint cavity (exudates), was graded using an arbitrary scale from 0 (no inflammation) to 3 (severe inflammation). Chondrocyte death was determined as the percentage of cartilage area containing empty lacunae in relation to the total area. Cartilage surface erosion was determined as the amount of cartilage lost in relation to the total cartilage area. Bone destruction was determined in 10 different areas of the total knee joint section. Destruction was graded on a scale of 0 (no damage) to 3 (complete loss of bone structure). Histological analysis was performed by an investigator who was blinded to the experimental groups. The mean score for each animal in an experimental group was calculated by averaging the histopathologic scores in at least 5 section depths per joint.

Results

Zymosan Induced Joint Inflammation is not Sustained in Tenascin-C Deficient Mice Zymosan injection into the footpad was used to induce acute synovitis in mice. Wild type mice exhibited rapid paw swelling reaching maximal paw diameter by 24 hours (2.56 mm, an increase of 62% of the starting paw diameter). This was maintained for a further 24 hours. After 2 days paw diameter decreased but paws remained swollen by 4 days (2.08 mm, an increase of 32%) (FIG. 1a). tenascin-C deficient mice exhibited a similar degree of paw swelling to wild type mice 24 hours post injection (2.41 mm, an increase of 57% of starting paw diameter). However, swelling in the tenascin-C null mice subsided faster than in the wild type mice; paw diameter was significantly reduced at 2 days and had declined to 1.7 mm (an increase of only 11%) by 4 days (FIG. 1a). By day 4 post injection the paws of wild type mice were still visibly swollen and red, whereas the paws of tenascin-C null mice were not visibly swollen or red and resembled non-injected paws (FIG. 9).

This difference was reflected histologically at 4 days. The synovia of wild type mice were significantly inflamed and exhibited cellular infiltration and cartilage proteoglycan loss was observed (FIG. 1b, c). In contrast, the synovium of tenascin-C deficient mice exhibited no synovitis, cellular infiltrate or cartilage proteoglycan loss (FIG. 1d, e) and resembled the joints of sham injected and non injected mice (not shown). Quantification of joint inflammation revealed whilst there was little exudate (cellular mass in the joint cavity) in either wild type or tenascin-C null mice, levels of infiltrate (cellular mass in the synovial layer) were significantly reduced in tenascin-C null mice (FIG. 1f). No erosion of cartilage or bone occurred in mice of either genotype (not shown), however a low level of chondrocyte death occurred in wild type mice, that was not observed in tenascin-C null mice (FIG. 1g). Thus tenascin-C expression appears to promote the maintenance of acute inflammation.

Tenascin-C Null Mice are Protected from Persistent Inflammation and Structural Damage During Antigen Induced Arthritis To determine whether tenascin-C also contributes to more destructive inflammatory joint disease, erosive arthritis was induced by intra-articular injection of mBSA into the knee joint following immunization with mBSA. This model involves both cellular and humoral immune responses and induces pathological changes similar to human RA (Brackertz (1977)). Injection of mBSA induced a similar inflammatory response in both tenascin-C null and wild type mice. Cell infiltration and synovial thickening is apparent by 24 hours in mice of both genotypes (FIG. 2c-f, h,i) compared to sham injected (FIG. 2a, b, g) or non injected (not shown) mice.

However, this does not persist in tenascin-C null mice as it does the wild type mice. By 3 days post injection wild type mice exhibit increased inflammation of the meniscus and capsule, synovial hyperplasia, cells and fibrin deposits in the joint space, pannus formation and localized cartilage proteoglycan loss (FIG. 3a, b, f). In contrast, by 3 days in tenascin-C null mice inflammation is limited to the capsule, synovial inflammation has subsided and there are no fibrin/cell aggregates present in the joint space, no pannus formation and no cartilage proteoglycan loss (FIG. 3c, d, e).

By 7 days wild type mice exhibited persistent inflammatory cell infiltration and joint space exudate, extensive synovitis and pannus formation and destruction of articular cartilage and bone erosion (FIG. 4a, b). Sham injected knees and knees from mice that had undergone no injection were healthy and exhibited no inflammation or joint destruction (not shown). tenascin-C deficient mice also had healthy joints that exhibited only mild inflammatory cell infiltration, with no joint space exudate, synovitis, pannus formation, destruction of articular cartilage or bone erosion (FIG. 4c, d). Joints from tenascin-C deficient mice that had been sham injected and or that had undergone no injection were also healthy (not shown).

These histological data are reflected upon scoring of joint disease as described in materials and methods. Levels of cellular infiltrate and exudate observed in both wild type mice and tenascin-C null mice 24 hours post injection were not significantly different. However, whilst cellular mass continued to increase in wild type mice over time, this response was attenuated in tenascin-C null mice and cell numbers in the joint decreased over time (FIG. 4e). Increasingly high levels of chondrocyte death occurred in the cartilage of wild type mice over time, but no significant death was observed in tenascin-C null mice (FIG. 4f. No cartilage surface erosion and bone erosion was evident in wild type mice at 24 hours or 3 days (not shown) but significant tissue destruction had occurred by 7 days. In contrast tenascin-C null mice exhibited no tissue destruction at 24 hours, 3 days (not shown) or 7 days (FIG. 4f). These data indicate that whilst the initiation of joint inflammation (cell influx into the synovium and joint space) is unaffected in tenascin-C null mice, unlike in wild type mice disease does not progress to tissue destruction and cell death. These results demonstrate that expression of tenascin-C is required for persistent synovial inflammation and joint destruction in this model.

EXAMPLE 4

Cell Culture

Patient Specimens

Human monocytes were isolated from peripheral blood (London Blood Bank) and macrophages were derived from monocytes after differentiation for 4 days with 100 ng/ml of M-CSF as previously described (Foxwell (1998)).

RA membrane cells (representing a mixed population of all synovial cell types) were to isolated from synovial membranes obtained from patients undergoing joint replacement surgery as previously described (Brennan (1989)). RA synovial fibroblasts were isolated from the mixed population of RA membrane cells as previously described (Brennan (1989)). The study was approved by the local Trust ethics committee (Riverside NHS Research Committee), and waste tissue (synovium after joint replacement surgery) was obtained only after receiving signed informed consent from the patient and anonymyzing the tissue to protect patient identity.

Immediately after isolation, RA membrane cells and macrophages were cultured at $1 \times 10^5$ cells/well in RPMI 1640 containing 10% (v/v) FBS and 100 U/ml (Units/ml) penicillin/streptomycin in 96-well tissue culture plates for 24 hours before stimulation. Synovial fibroblasts (used only at either passage number 2 or 3) were cultured at $1 \times 10^4$ cells/well in DMEM containing 10% (v/v) FBS and 100 U/ml penicillin/streptomycin in 96-well tissue culture plates for 24 hours before stimulation.

Mouse Embryonic Fibroblasts (MEFs) and Bone Marrow Derived Macrophages (BMDMs)

MEFs express high levels of mRNA of all 9 murine TLRs and are specifically and highly responsive to TLR ligand activation. MEFs from mice with targeted deletions of TLR2, TLR4 and MyD88 demonstrate profound defects in their IL-6 response to specific ligands (Kurt-Jones (2004)). MEFs were isolated from d13 embryos harvested from age-matched, pregnant female wild type, TLR2, TLR4 and null mice (as described in Todaro (1963)). Fibroblasts were cultured at $2 \times 10^4$ cells/well in DMEM containing 10% (v/v) FBS and 100 U/ml penicillin/streptomycin in 96-well tissue culture plates for 24 hours before stimulation.

BMDMs were derived by aspirating the femurs of age matched female wild type, TLR2 and TLR4 null mice as described in Butler (1999)) and culturing the cells for 7 days in DMEM, 20% (v/v) FBS, 10 ml/L (v/v) antibiotic-antimycotic solution PSA, 50 μM β-Mercaptoethanol and 10 ng/ml M-CSF. Macrophages were then cultured at $1 \times 10^5$ cells/well in DMEM, 20% (v/v) FBS, 10 ml/L (v/v) antibiotic-antimycotic solution PSA, 50 μM β-Mercaptoethanol in 96-well tissue culture plates for 24 hours before stimulation.

HEK293 Cell Lines

HEK293 cell lines expressing TLR2 and TLR4/CD14/MD-2 were cultured at $1 \times 10^4$ cells/well in DMEM containing 10% (v/v) FBS and 10 μg/ml blasticidin in 96-well tissue culture plates for 24 hours before stimulation.

Cell Stimulation and Assessment of Cytokine Synthesis

Cells were incubated for 24 hours at 37° C. with the indicated doses of tenascin-C and recombinant tenascin-C fragments (1.0 μM-1.0 nM). Cells were also stimulated where indicated with LPS (1 ng/ml for human macrophages, 10 ng/ml for human fibroblasts, RA membrane cells and HEKs, 100 ng/ml for MEFS and BMDMs and 10 ng/ml for HEKS), PAM3 (10 ng/ml for human macrophages, human fibroblasts, and HEKs, 100 ng/ml for MEFs and BMDMs), murine IL-1 (5 ng/ml for MEFS) and murine TNF-α (100 ng/ml for MEFS). Unless specifically stated otherwise rough LPS was used for in vitro studies.

For adenoviral gene transfer experiments, human RA synovial fibroblasts were incubated with adenoviral vectors at a multiplicity of infection of 100, washed after 2 hours, cultured in complete medium for 24 hours, then stimulated for 24 hours, after which time supernatants were collected.

Where stated, cells were pre-incubated with 10 μg/ml anti-CD14 antibody, 10 μg/ml IL1 receptor antagonist, 10 μg/ml anti-TLR2 antibody, 25 μg/ml anti-TLR4 antibody, 10 or 25 μg/ml isotype control antibody, 25 μg/ml polymyxin B, or 1 μg/ml msbB LPS, for 30 minutes at 37° C. before stimulation. Where stated, recombinant tenascin-C and FBG, and LPS were boiled for 15 minutes before addition to cells.

In all cases, viability of the cells was not significantly affected throughout the experimental time period when examined by the MTT cell viability assay (Sigma, Poole, UK).

Supernatants were subsequently examined for the presence of the cytokines TNF-α, IL-6, and IL-8 by enzyme-linked immunosorbent assay (ELISA) according to the manufacturer's instructions. Absorbance was read on a spectrophotometric ELISA plate reader (Labsystems Multiscan Biochromic, Vantaa, Finland) and analyzed using the Ascent software program (Thermo Labsystems, Altrincham, UK).

Results

Tenascin-C Induces TNF-α, IL-6 and IL-8 Synthesis in Primary Human RA Synovial Fibroblasts and Macrophages We next investigated whether tenascin-C might activate the innate immune response. tenascin-C was used to stimulate primary human macrophages and RA synovial fibroblasts and the production of the pro-inflammatory cytokines TNF-α, IL-6 and IL-8 examined. The bacterial cell wall component LPS was used as a positive control. tenascin-C induced a cell type specific cytokine profile which was significantly different from LPS. It dose dependently stimulated the production of TNF-α, IL-6 and IL-8 in human macrophages (FIG. 5a). However, tenascin-C only induced IL-6 synthesis in synovial fibroblasts, whereas LPS induced both IL-6 and IL-8 (FIG. 5b). Neither LPS nor tenascin-C induced TNF-α synthesis in fibroblasts (data not shown). tenascin-C stimulation of IL-6 (FIG. 5c), IL-8 and TNF-α by human macrophages and IL-6 by synovial fibroblasts (not shown) was heat sensitive and unaffected by the LPS inhibitor, polymyxin B. Together these results provide strong evidence that cytokine induction by tenascin-C is not due to LPS contamination.

The Fibrinogen-Like Globe (FBG) Mediates Tenascin-C Activation of Cells.

Tenascin-C is a large hexameric molecule, each domain of which binds to different cell surface receptors (reviewed in Orend (2005)). Understanding the mechanism of action of tenascin-C will require identification of which domain(s) are critical for promoting cytokine production. We synthesized recombinant proteins comprising different domains of the molecule (FIG. 10). Each domain was made in E. coli, purified (FIG. 11), and found to contain <10 pg/ml LPS by subjecting neat protein to the Limulus amaebocyte lysate assay. Only one domain of tenascin-C was active. The fibrinogen-like globe (FBG) stimulated TNF-α synthesis in human macrophages (FIG. 6a), IL-6 and IL-8 synthesis in human macrophages (not shown) and IL-6 in RA synovial fibroblasts (not shown) to an equal extent to full-length tenascin-C. Like full-length tenascin-C, FBG did not induce IL-8 synthesis in RA synovial fibroblasts where LPS did (data not shown). FBG induced cytokine synthesis was also heat sensitive and unaffected by polymyxin B (data not shown).

The FBG Domain of Tenascin-C Induces Cytokine Production in Human RA Synovium and Joint Inflammation in Mice.

We investigated whether FBG could promote expression of inflammatory cytokines in synovial membranes from RA patients. This tissue model of RA (comprising a mixed population of all synovial cell types) spontaneously produces high levels of IL-6, IL-8 and TNF-α (Brennan (1989)) (FIG. 6b). FBG further enhanced synthesis of all these cytokines (FIG. 6b). To determine whether FBG could induce inflammation in vivo, wild type mice were injected intra-articularly with FBG. We observed a transient and dose dependent stimulation of joint inflammation. No inflammation or proteoglycan loss occurred in non-injected mice or in mice injected with PBS (FIG. 6c-e) or 100 ng FBG (data not shown). In mice injected with 1 μg FBG inflammatory cell infiltration (FIG. 6f), mild synovitis, pannus formation (FIG. 6g) and proteoglycan loss (FIG. 6h) was observed. A similar response was seen in mice injected with 3 μg FBG (data not shown). Upon histological quantification, high levels of cellular infiltrate and exudate and chondrocyte death were observed in mice injected with FBG, together with a modest amount of cartilage surface erosion and bone damage (FIG. 6i).

FBG Mediated Cytokine Synthesis is Dependent on Myd88

Many DAMPs, including fibrinogen (Smiley (2001)), have been shown to stimulate the innate immune response by activation of TLRs. Therefore, we investigated whether TLRs might also mediate tenascin-C induced cytokine production. Myeloid differentiation factor 88 (MyD88) is required for signalling by all TLRs, except TLR3 (O'Neill (2008)). Infection of synovial fibroblasts with adenovirus expressing dominant negative MyD88, but not GFP control virus, abolished FBG induction of IL-6 (FIG. 7a). These data suggest that FBG induced inflammation is dependent on functional MyD88. This effect of FBG did not appear to be mediated by IL-1 as addition of IL-1 receptor antagonist did not inhibit induction of cytokines (data not shown). To confirm that FBG action is MyD88 dependent we demonstrated that FBG does not stimulate cytokine synthesis in embryonic fibroblasts isolated from mice with targeted deletions in the MyD88 gene. The TLR2 ligand PAM3, TLR4 ligand LPS and IL-1 all signal via MyD88. Stimulation with these was also abolished in MEFs from deficient mice. However, TNF-α, which does not signal via MyD88, was unaffected (FIG. 7b). Re-transfection of wild type MyD88 restored the responsiveness of these cells to FBG, PAM3, LPS and IL-1 (data not shown).

FBG Signals Via TLR4

TLRs exhibit specificity for endogenous ligands; proteins are recognised by one or both of TLR2 and 4 (reviewed in O'Neill (2008)). Neutralising antibodies to TLR4 inhibited both FBG and LPS induced IL-6, IL-8 and TNF-α synthesis in human macrophages and IL-6 synthesis in RA synovial fibroblasts but had no effect on the function of the TLR2 ligand, PAM3. Antibodies to TLR2 inhibited PAM3 mediated cytokine synthesis but had no effect on LPS or FBG induced cytokine synthesis. Isotype matched controls had no effect on cytokine synthesis induced by any ligand (TNF-α synthesis by human macrophages is shown in FIG. 8a). To confirm that FBG action is TLR4 dependent we demonstrated that FBG does not stimulate cytokine synthesis in embryonic fibroblasts or macrophages isolated from mice with targeted deletions in the TLR4 gene. FBG mediated cytokine synthesis was unaffected in embryonic fibroblasts or macrophages isolated from mice with targeted deletions in the TLR2 gene. Cells isolated from TLR2 deficient mice were unresponsive to PAM3 but responsive to LPS and IL-1. Cells isolated from TLR4 deficient mice were unresponsive to LPS but did respond to PAM3 and IL-1 (FIG. 8b, c). In addition, expression of TLR4 was required for the arthritogenic action of FBG in vivo; FBG was able to induce joint inflammation in TLR2 null mice but not in TLR4 null mice (FIG. 12).

Different Co-Receptor Requirements for FBG and LPS

LPS signalling via TLR4 is mediated by a receptor complex including the soluble protein MD-2 and GPI-linked cell surface or soluble CD14 (reviewed in Fitzgerald (2004)). We next examined whether CD14 and MD-2 are required for FBG activation of TLR4. As a positive control here we examined the activity of smooth glycosylated LPS which requires both MD-2 and CD14 (Jiang (2005)). LPS mediated IL-6, IL-8 and TNF-α synthesis by human macrophages and IL-6 synthesis by RA synovial fibroblasts was inhibited by anti-CD14 antibodies and an antagonistic LPS derived from the msbB mutant *E. coli* which competes for LPS binding to MD-2 (Coats (2007)). Conversely, both PAM3, which does not require these co-receptors for activation of TLR2, and FBG-mediated cytokine synthesis was unaffected by anti CD14 antibodies or msbB mutant LPS (FIG. 8d shows TNF-α synthesis by human macrophages). These data suggest that neither CD14 nor MD-2 is required for FBG mediated cytokine synthesis. Therefore, whilst LPS and FBG both signal via activation of TLR4, they may have different co-receptor requirements.

EXAMPLE 5

Inhibition of Tenascin-C Action and Synthesis in Human Tissue

This example studies the effect of (1) prevention ofn the pro-inflammatory action of tenascin-C and (2) inhibition of tenascin-C expression in the human RA synovium.

Methods

Peptide Synthesis

Nine overlapping peptides comprising the entire FBG domain (table 2) were synthesized by Biogenes, Germany. Peptides were cleaved at room temperature (cleavage mixture: 90% trifluoroacetate, 5% thioanisol, 3% ethanedithiol, 2% anisole), purified by reverse phase high performance liquid chromatography, and characterized by MALDI TOF mass spectral analysis. The purity of the peptides was >85% as determined high performance liquid chromatography.

The facility was unable to synthesize peptide 7, presumably due to the formation of secondary structure that prevented elongation of the peptide chain (as previously reported (LaFleur (1997))).

TABLE 2

Overlapping peptides that span the entire FBG domain of human tenascin-C

| Peptide # | Amino acid sequence |
|---|---|
| 1 | TIGLLYPFPKDCSQAMLNGDTTSGLYTIYL [SEQ ID NO: 20] |
| 2 | YTIYLNGDKAEALEVFCDMTSDGGGWIVFL [SEQ ID NO: 21] |
| 3 | WIVFLRRKNGRENFYQNWKAYAAGFGDRRE [SEQ ID NO: 22] |
| 4 | GDRREEFWLGLDNLNKITAQGQYELRVD [SEQ ID NO: 23] |
| 5 | ELRVDLRDHGETAFAVYDKFSVGDAKTRYK [SEQ ID NO: 24] |
| 6 | KTRYKLKVEGYSGTAGDSMAYHNGRSFST [SEQ ID NO: 25] |
| 7 | RSFSTFDKDTDSAITNCALSYKGAFWYRN [SEQ ID NO: 26] |
| 8 | WYRNCHRVNLMGRYGDNNHSQGVNWFHWKG [SEQ ID NO: 27] |
| 9 | FHWKGHEHSIQFAEMKLRPSNFRNLEGRRKRA [SEQ ID NO: 28] |

Patient Specimens and Cell Culture

RA membrane cells (representing a mixed population of all synovial cell types) were isolated from synovial membranes obtained from patients undergoing joint replacement surgery (Brennan (1989)). Synovial membrane tissue was digested in RPMI 1640 (GIBCO) containing 5% fetal calf serum (FCS) (GIBCO), 5 mg/ml collagenase type IV (Sigma) and 0 15 mg/ml DNAse type I (Sigma) and incubated at 37° C. for 2 h.

After incubation the tissue was pipetted through a nylon mesh into a sterile beaker. The cells were then washed three times in complete medium (RPMI 1640 supplemented with 10% FCS). RA synovial fibroblasts were isolated from the mixed population of RA membrane cells by selection in DMEM (Bio-Whittaker) supplemented with 10% FBS, 1 µM glutamine, 100 U/ml penicillin, and streptomycin. Human monocytes were isolated from peripheral blood (London Blood Bank) and macrophages were derived from monocytes after differentiation for 4 days with 100 ng/ml of M-CSF.

The study was approved by the local Trust ethics committee, and waste tissue (synovium after joint replacement surgery) was obtained only after receiving signed informed consent from the patient and anonymising the tissue to protect patient identity.

Cell Stimulation and Assessment of Cytokine Synthesis

Immediately after isolation, RA membrane cells were cultured at $1\times10^5$ cells/well in RPMI 1640 containing 10% (v/v) FBS and 100 U/ml penicillin/streptomycin in 96-well tissue culture plates. Cells were incubated for 24 h at 37° C. with no addition, buffer control (PBS, 1% BSA, 0.01% $NaN_3$), or with 25 µm, 100 µM or 250 µM of each FBG spanning peptide.

Synovial fibroblasts (used only at either passage number 2 or 3) were seeded at a concentration of $5\times10^4$ cells in a 3.5-cm dish. siRNA was transfected at a final concentration of 10 nM using Lipofectamine 2000 (Invitrogen) for 4 h in serum-free OptiMEM I. Two different siRNAs against human tenascin-C were used (s7069 and s229491) (Applied Biosystems).

siRNA sequences of s7069 are: (sense 5' CGCGAGAAC-UUCUACCAAAtt 3' [SEQ ID NO: 29], antisense 5' UUUGGUAGAAGUUCUCGCGtc 3' [SEQ ID NO: 30]) and of s229491 are (5' GGAAUAUGAAUAAAGAAGAtt 3' [SEQ ID NO: 31], antisense 5' UCUUCUUUAUU-CAUAUUCCgg 3' [SEQ ID NO: 32]). siRNA against luciferase (Dharmacon) was transfected as a non-targeting control.

Four hours after transfection, medium was changed with pre-equilibrated Dulbecco's modified Eagle's medium containing 10% FBS (v/v) and cells were incubated for a further 48 h and 72 h. Cells were then stimulated with 10 ng/ml LPS for 24 h at 37° C. Tenascin-C mRNA and protein levels were quantitated by PCR and western blotting respectively. Total RNA was extracted from cells using a QiaAmp RNA Blood mini kit (Qiagen, Germany). cDNA was synthesised from equivalent amounts of total RNA using SuperScript® III Reverse Transcriptase (Invitrogen) and 18-mer oligo dTs (Eurofins MWG Operon).

Gene expression was analysed by delta-delta ct methods based on quantitative real-time PCR with TaqMan primer set human tenascin-C(Hs01115663-m1) and human ribosomal protein endogenous control (RPLPO) (4310879E) (Applied Biosystems) in a Corbett Rotor-gene 6000 machine (Corbett Research Ltd). Tenascin-C protein was detected in cell supernatants and cell lysates by by SDS PAGE and western blotting using antibody MAB1908 (Millipore).

Macrophages were cultured at $1\times10^5$ cells/well in RPMI 1640 containing 5% (v/v) FBS and 100 U/ml penicillin/streptomycin in 96-well tissue culture plates for 24 h before stimulation. Cells were incubated for 24 h at 37° C. with no addition, 1.0 µM FBG, 1 ng/ml LPS or 1 or 20 µM FBG peptide. Where stated, cells were pre-incubated with 20 µM FBG peptides for 15 min.

The viability of the cells was not significantly affected throughout the experimental time period when examined by the MTT cell viability assay (Sigma, Poole, UK). Supernatants were examined for the presence of the cytokines TNF-α, IL-6, and IL-8 by enzyme-linked immunosorbent assay (ELISA) according to the manufacturer's instructions (R&D systems). Absorbance was read on a spectrophotometric ELISA plate reader (Labsystems Multiscan Biochromic, Vantaa, Finland) and analyzed using the Ascent software program (Thermo Labsystems, Altrincham, UK).

Statistical Methods

Mean, SD and SEM were calculated using GraphPad (GraphPad Software Inc., San Diego, Calif.).

Results

Blockade of Cytokine Synthesis in RA Membrane Cultures by Specific FBG Peptides

The approach of peptide inhibition has been used successfully to pinpoint the αvβ3 integrin binding site in the FBG domain of tenascin-C and to prevent cell adhesion in response to this domain of tenascin-C (Lafleur (1997) and Yokoyama (2000)).

We synthesized a series of 8 overlapping peptides of ~30 amino acids that span the entire sequence of FBG (Table 2). Peptides were tested for the ability to block spontaneous cytokine synthesis in RA synovial membrane cultures. TNF and IL8 synthesis was inhibited by peptides 3 and 8, but not by any other peptide (TNF shown in FIG. 15). Peptides 3 and 8 dose dependently inhibited cytokine synthesis with the highest concentrations achieving 95% and 56% inhibition respectively (FIG. 16). Whilst peptide 5 had no effect on TNF synthesis, it dose dependently blocked IL8 synthesis in RA membrane cells with a maximal inhibition of 81% (FIG. 16).

To map the active domain within FBG responsible for inducing cytokine production we stimulated primary human macrophages with each FBG peptide. Peptides 1, 5 and 6 all induced cytokine synthesis in a dose dependent manner. (FIG. 17).

To determine if any peptide could block FBG induced cytokine synthesis in human macrophages, cells were pre-incubated with each FBG peptide before stimulation with either whole FBG or LPS. Peptide 5 specifically blocked FBG mediated cytokine synthesis, whilst peptide 8 blocked cytokine synthesis in response to both LPS and FBG (FIG. 18).

Peptide 8 therefore non-specifically blocks cytokine production induced by any stimuli. This domain is the integrin binding domain of FBG that mediates cell adhesion and thus may be acting to prevent cell attachment to tissue culture plates. Peptide 5 specifically blocks FBG-induced cytokine synthesis suggesting that targeting this domain may be useful in preventing tenascin-C induced inflammation.

Silencing Tenascin-C Gene Expression Inhibits Cytokine Synthesis in RA Synovial Fibroblasts Examination of the effect of inhibiting tenascin-C expression in the human RA synovium has identified synovial fibroblasts as the major source of tenascin-C in RA (FIG. 1C) (in Goh 2010).

siRNA mediated knockdown of tenascin-C expression in these cells has been shown with a maximal efficiency between 94-96% (FIG. 19). In cells transfected with tenascin-C siRNA, both the basal level of cytokine synthesis and LPS induced cytokine production was inhibited by 38% and 44% respectively compared to control cells (FIG. 19).

These data reveal that silencing tenascin-C in RA synovial fibroblasts reduces the synthesis of pro-inflammatory cytokines and suggest that ablation of tenascin-C expression is a viable strategy to inhibit inflammation in the synovium.

This work has established that blocking tenascin-C activity (with peptides) and tenascin-C expression (with siRNA) reduces inflammatory cytokine synthesis in human RA synovia. These data shows that tenascin-C blockade is of potential clinical benefit in treating RA and other inflammatory diseases.

EXAMPLE 6

In Vitro Citrullination

Equal volumes of protein and 2× citrullination buffer (200 mM Tris HCl, pH 7.4, 20 mM CaCl2, 10 mM DTT) were mixed. 8.75 U rabbit skeletal PAD (product number P1584 from Sigma) per mg substrate protein was added and incubated for 3 hours at 37° C. or 2 hours at 50° C. Citrullination was confirmed by size shift visualized by coomassie blue staining of SDS PAGE or by AMC detection.

The results shown in FIG. 20 demonstrate that purified fibrinogen and FBG can be citrullinated in vitro.

In vitro citrullination of purified full length tenascin-C is shown by the results in FIG. 21.

EXAMPLE 7

AMC (Anti-Modified Citrulline) Detection of Citrullinated Proteins

Citrullination was detected using a protocol from an anti-citrulline (Modified) Detection Kit (Millipore (catalogue: 17-347)).

A. Nitrocellulose Blot Preparation
1. Run SDS-PAGE and transfer to nitrocellulose. Wash blot with water 2×5 min.
2. Incubate blot in 10 ml 0.1% ovalbumin in TBS 15 min RT 3. Wash with water 2×10 min
B. Modification of Citrulline Residues
1. Mix 3 ml Reagent A and 3 ml Reagent B. Prepare just before use.
2. Add modification buffer to blot in light-proof container, incubate at 37° C. 5-7 hrs.
3. Rinse blot 4-5 times in water.
C. Detection of Modified Citrulline Residues
1. Block blot in freshly prepared 3% non-fat dried milk in TBS for 30 min-1 hr.
2. Incubate blot with 5-8 ml of 1:1000 dil of anti-modified citrulline antibody diluted in TBS-MLK overnight with agitation at 4° C. (Seems to work with a 2-3 hr incubation RT).
3. Rinse blot 3× with water, then wash 1×15 min, then 3×5 min.
4. Incubate the blot with 5-8 ml of 1:5000 dil of goat anti-rabbit HRP-conjugated IgG in TBS-MLK for 1 hr at RT with agitation.
5. Wash blot as in step 3.
6. Wash blot in TBS-0.05% Tween 20 for 3-5 min.
7. Rinse blot in 4-5 changes of water.
8. Use ECL-plus for detection.

FIG. 22 shows confirmation of the citrullination of FBG and tenascin-C by western blot.

EXAMPLE 8

FBG is Citrullinated by PAD In Vitro

FIG. 23 shows FBG is citrullinated by PAD in vitro. In particular, an increased molecular weight of FBG in Coomassie-blue stained SDS PAGE and Western Blotting with an anti-modified citrulline specific antibody demonstrates that FBG is citrullinated by rPAD2, hPAD2 and hPAD4 in a dose- and time dependent manner.

EXAMPLE 9

Demonstration that Citrullination Modulates the Pro-Inflammatory Activity of Tenascin-C Primary human macrophages were isolated as described above and cultured at $1 \times 10^5$ cells/well in RPMI 1640 containing 5% (v/v) FBS and 100 U/ml penicillin/streptomycin in 96-well tissue culture plates for 24 h before stimulation. Cells were incubated for 24 h at 37° C. with no addition (UN), different concentrations (uM) of native FBG (nFBG) or cit FBG (cFBG) or citrullination buffer alone (CIT) or cit buffer plus PAD enzyme (CIT+PAD).

The viability of the cells was not significantly affected throughout the experimental time period when examined by the MTT cell viability assay (Sigma, Poole, UK). Supernatants were examined for the presence of the cytokines TNF-α by enzyme-linked immunosorbent assay (ELISA) according to the manufacturer's instructions (R&D systems). Absorbance was read on a spectrophotometric ELISA plate reader (Labsystems Multiscan Biochromic, Vantaa, Finland) and analyzed using the Ascent software program (Thermo Labsystems, Altrincham, UK).

FIG. 24 shows that citrullination enhances cytokine production stimulated by FBG.

EXAMPLE 10

Serum from RA Patients Reacts with Citrullinated Tenascin-C and Citrullinated FBG Unlike Healthy Controls SDS PAGE of Citrullinated Proteins
33.33 ul of citrullination reaction (cit-TNC alone or cit-TNC combined with cit-FBG) was loaded into NuPAGE® Novex 4-12% Bis-tris gel using a 1.0 mm 2D single lane well.

Western Blot Detection with RA Serum
After electrophoresis proteins were transferred to nitrocellulose and the membrane blocked and then cut into strips (up to 8 strips ~0.7 cm wide). Strips were incubated with serum from RA patients or normal healthy individuals diluted 1:100 in 5% milk TBS-tween. Strips were incubated in 15 ml falcon tubes on rollers 1 h room temperature, then washed 3×5 min, 1×15 min in tubes with TBS-Tween. Strips were then incubated with secondary mouse anti-human Ig 1:5000 1 h in room temperature, then washed 3×5 min, 1×15 min in the dish with TBS-tween. Strips were finally incubated with ECL reagents and exposed to film.

Figure 2:
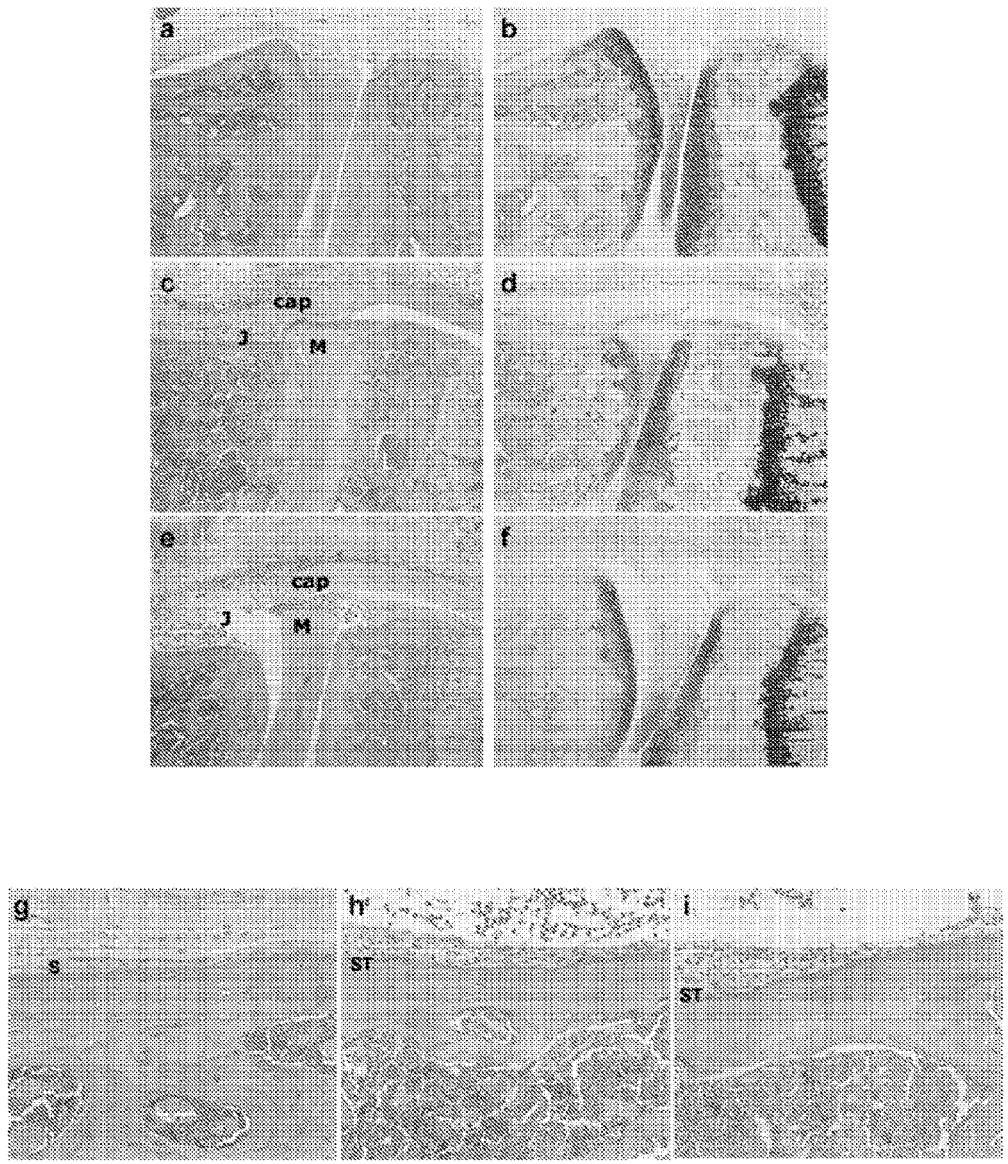
Figure 3:
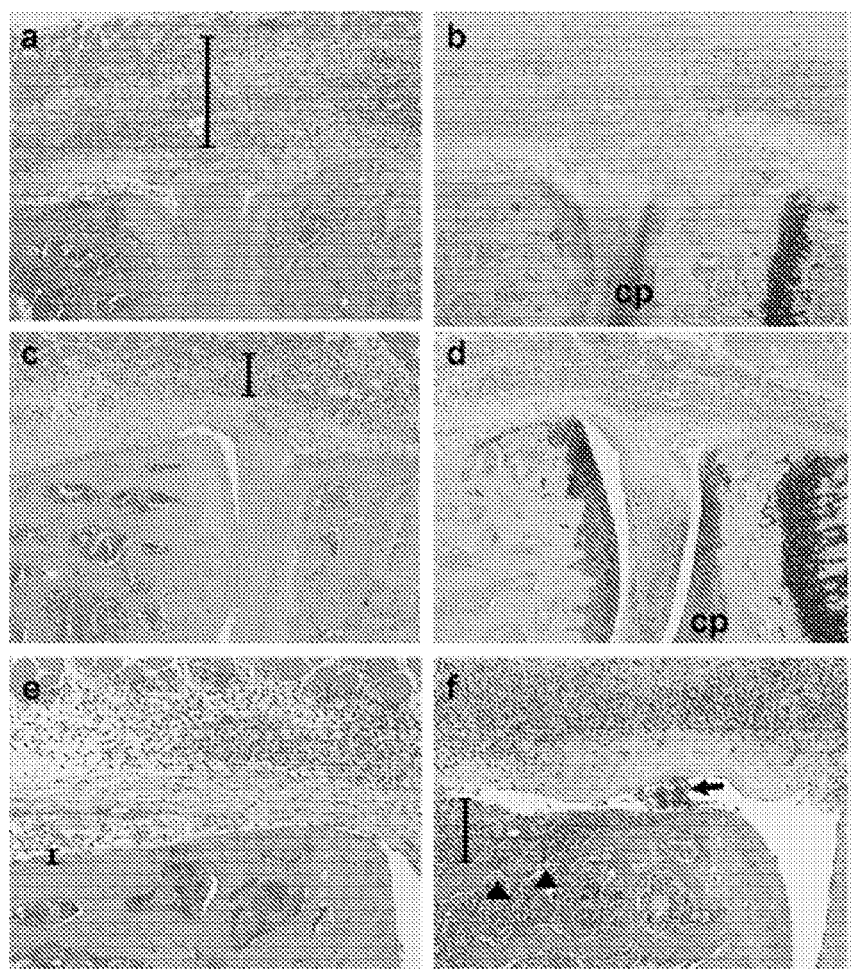
Figure 4:
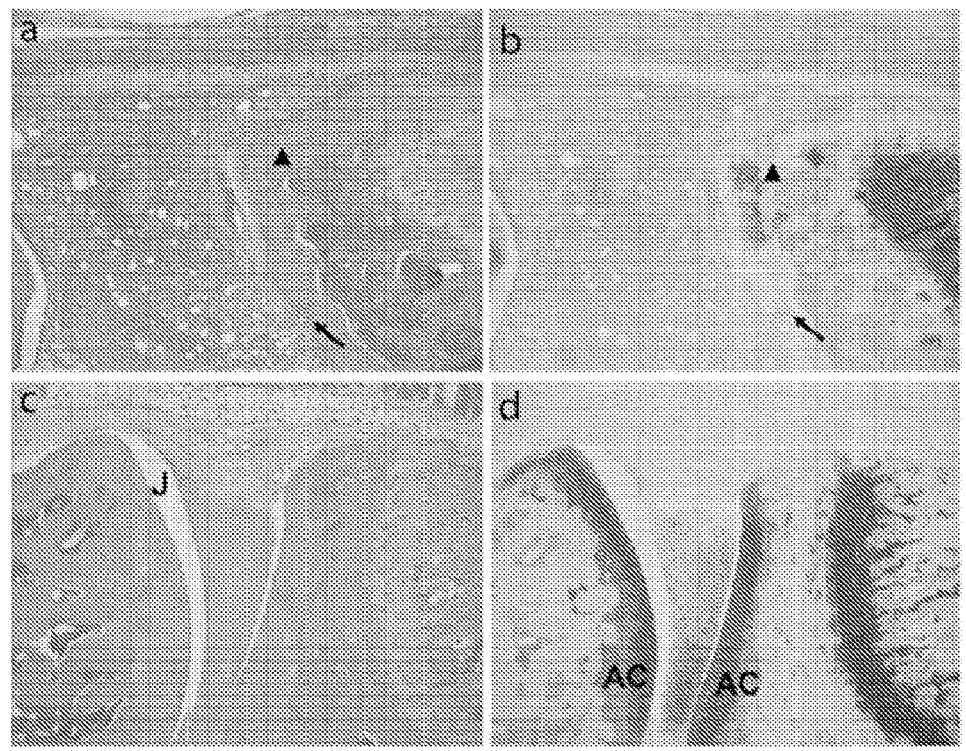
Figure 6:
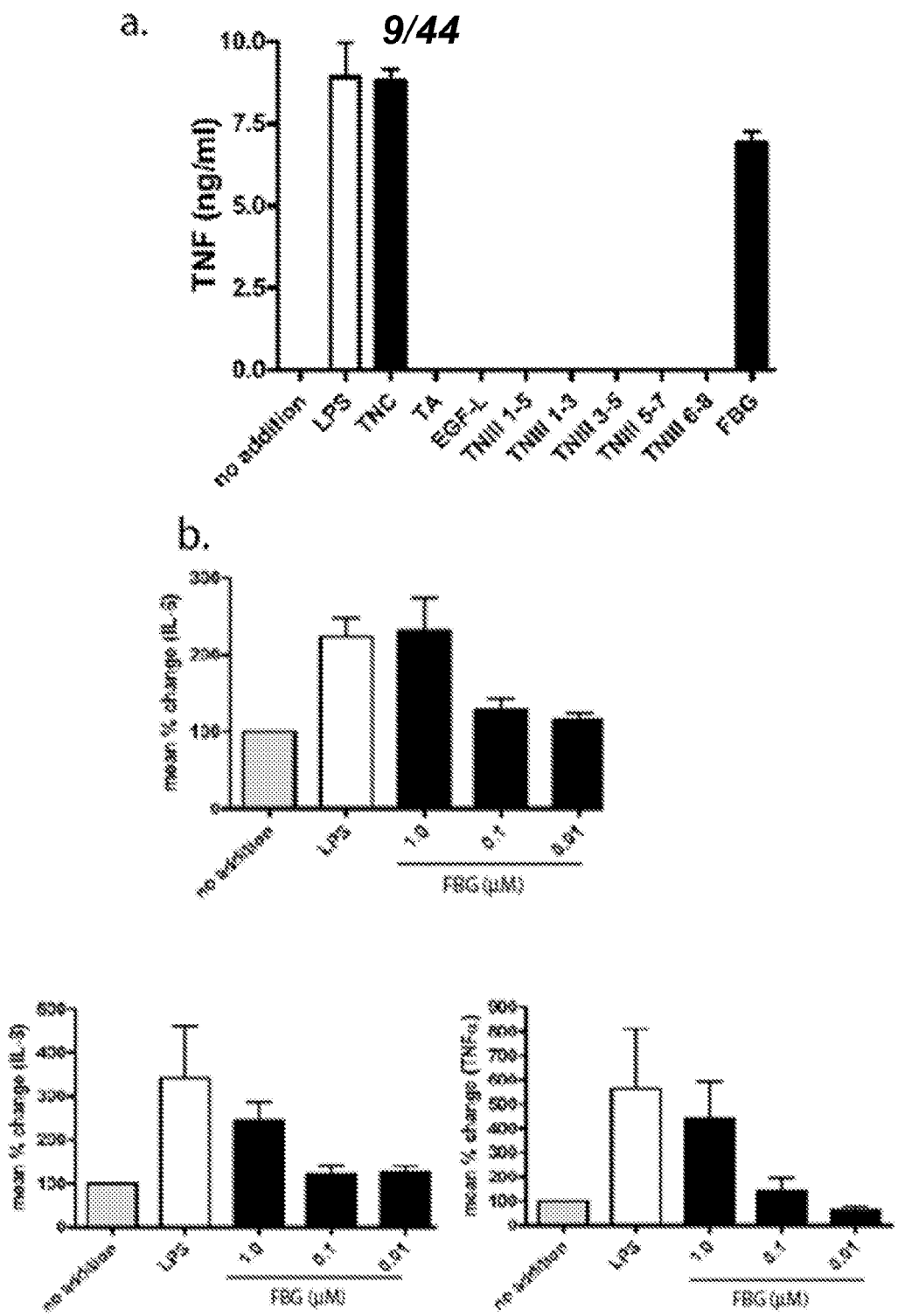
Figure 7:
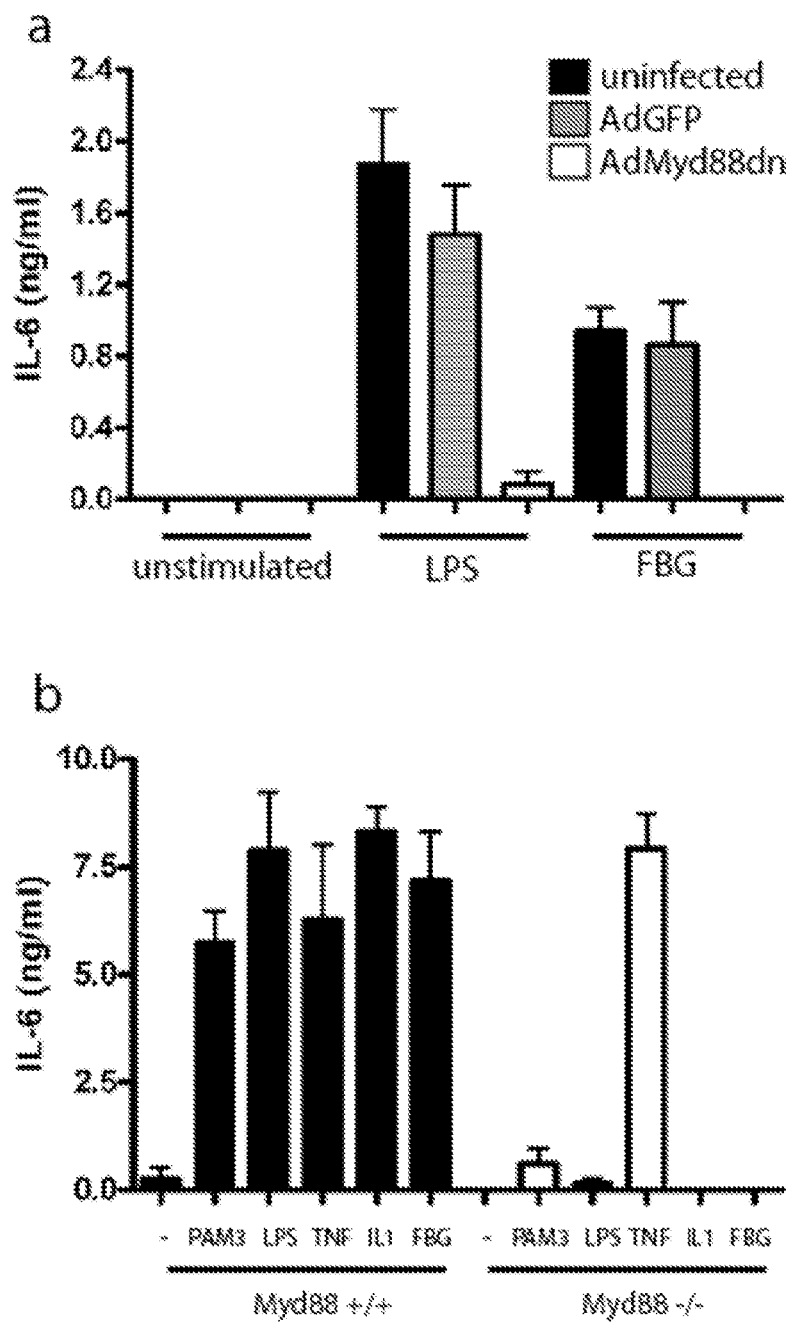
Figure 8:
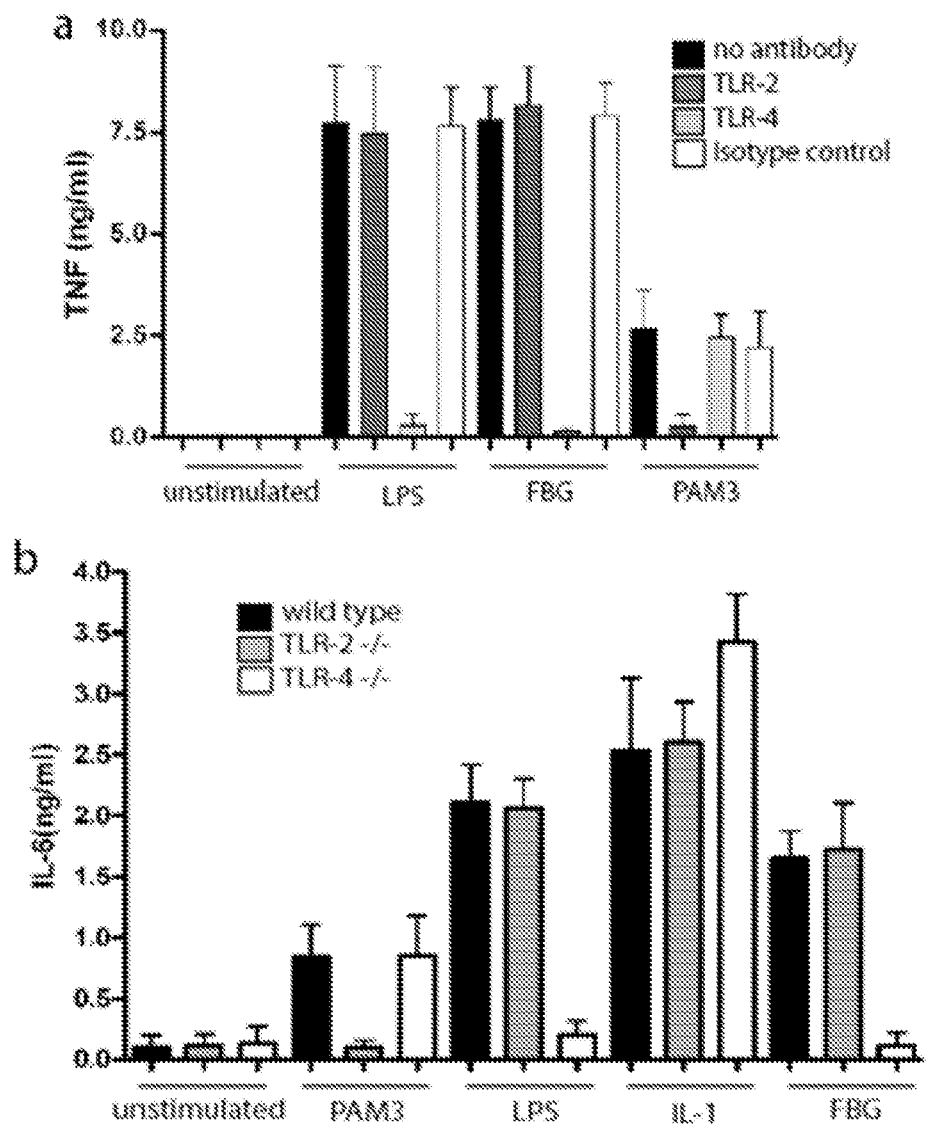
Figure 9:
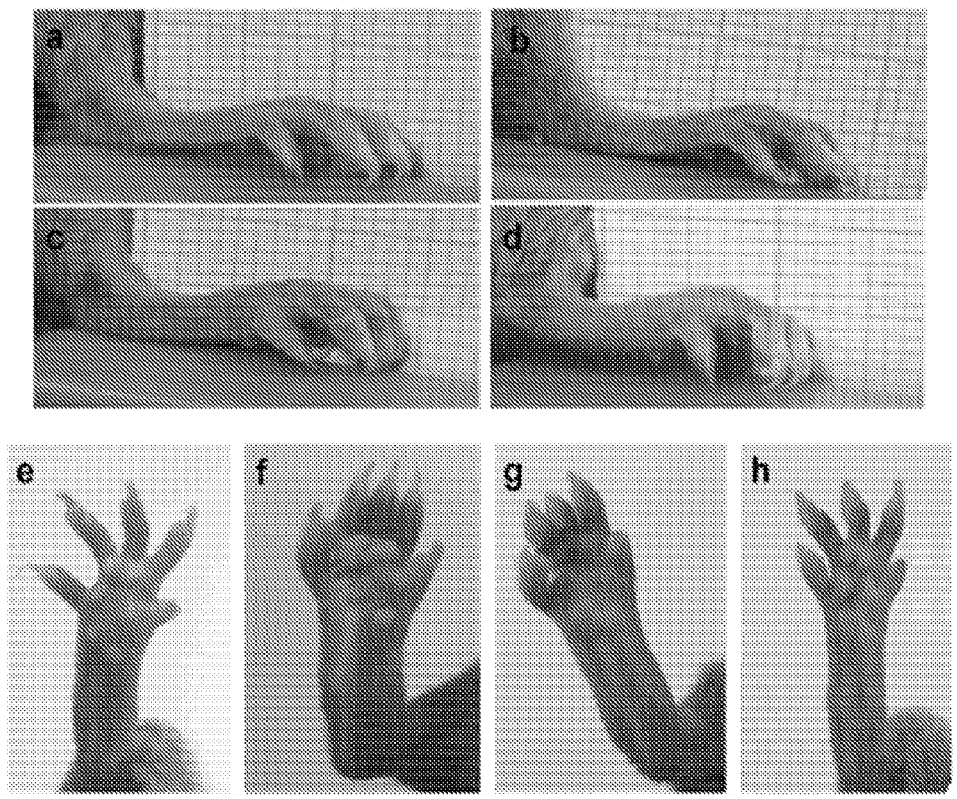
Figure 10:
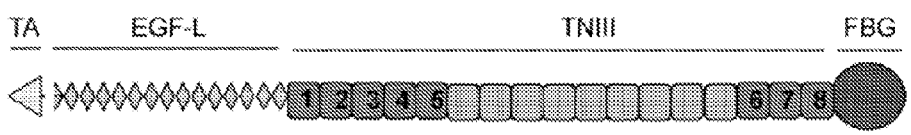
Figure 11:
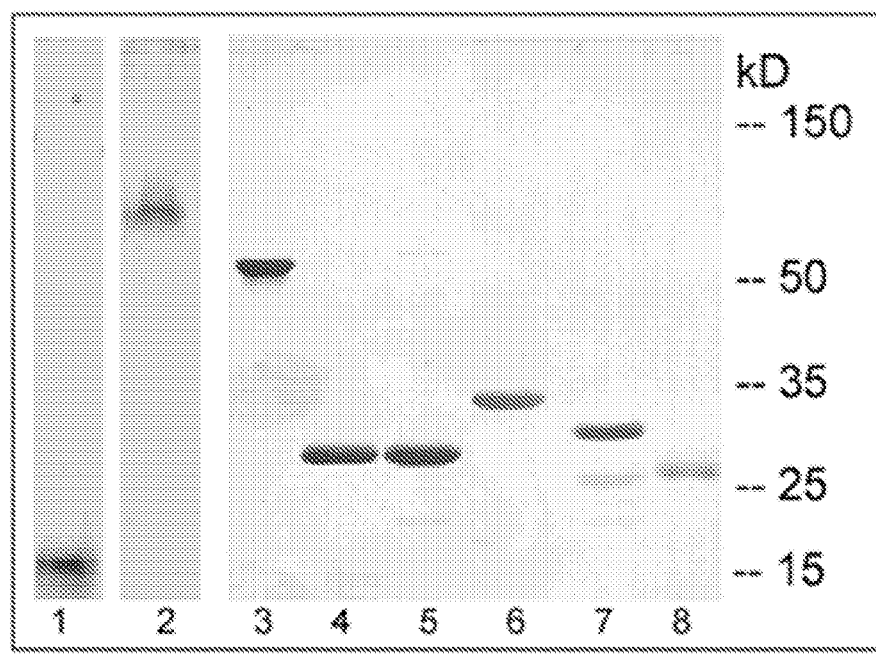
Figure 12:
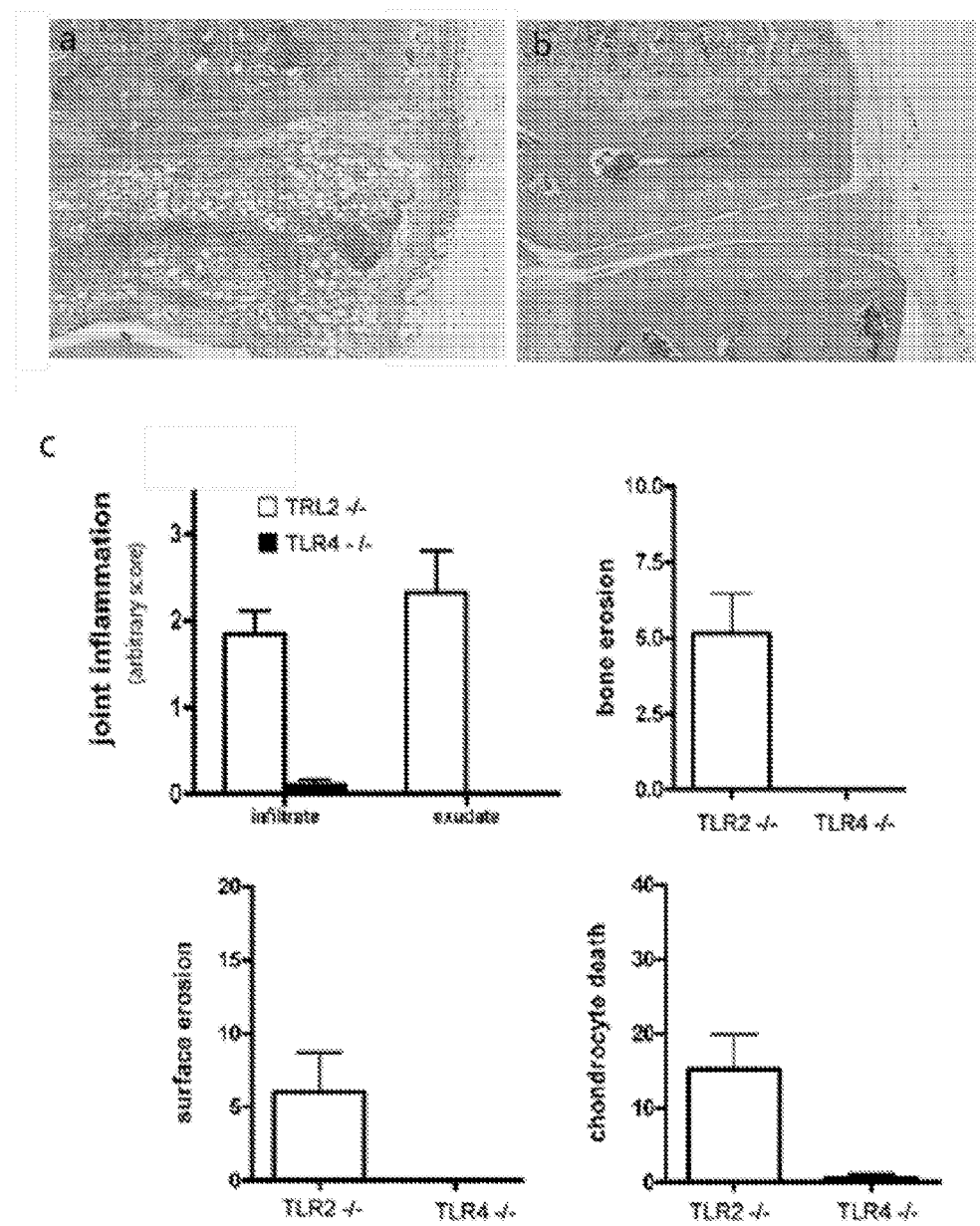
Figure 15:
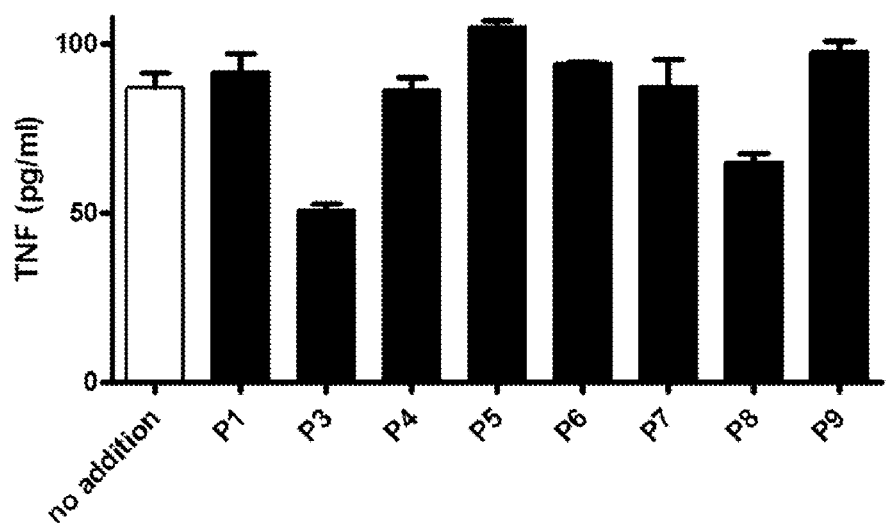
Figure 17:
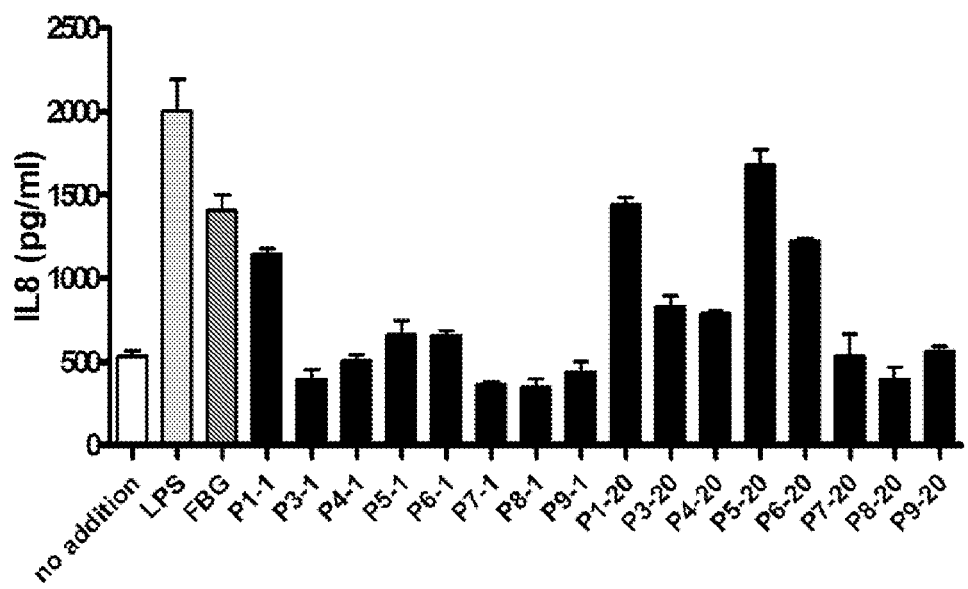
Figure 20:
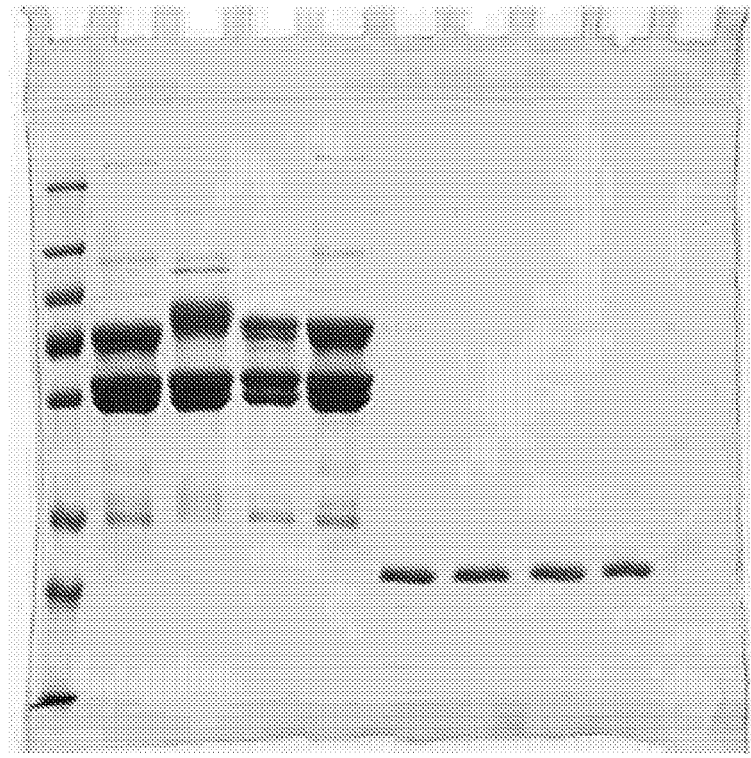
Figure 21:
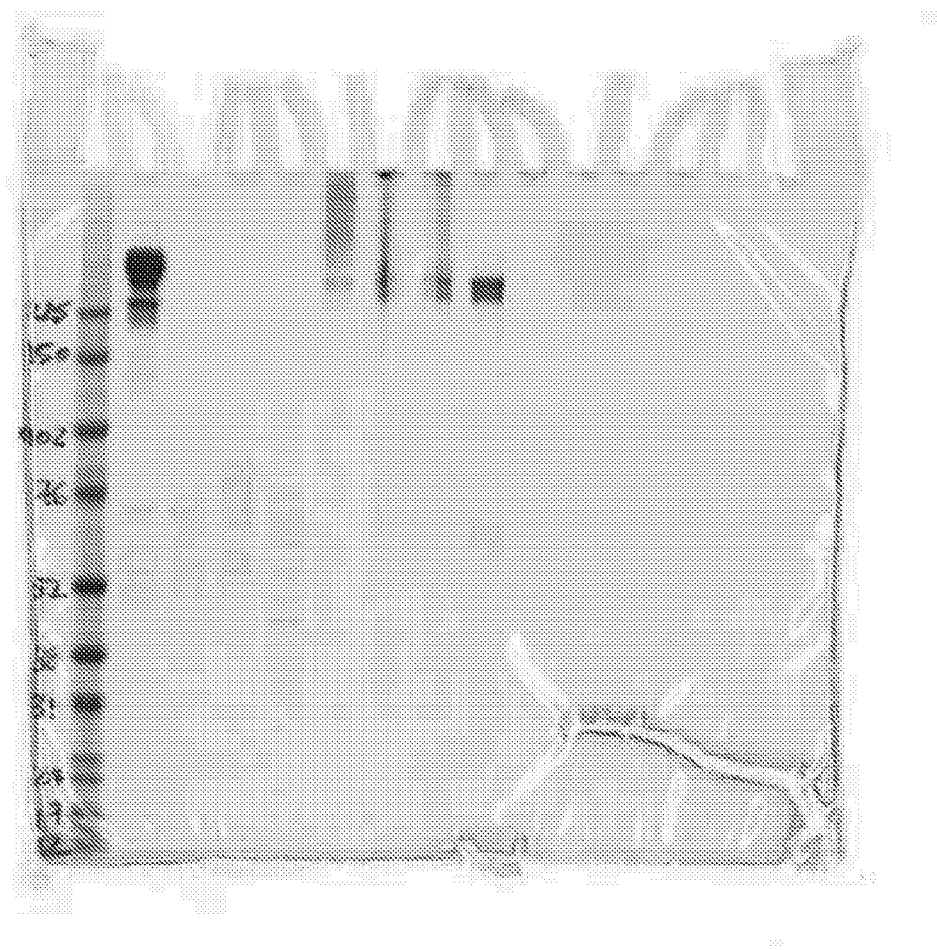
Figure 22:
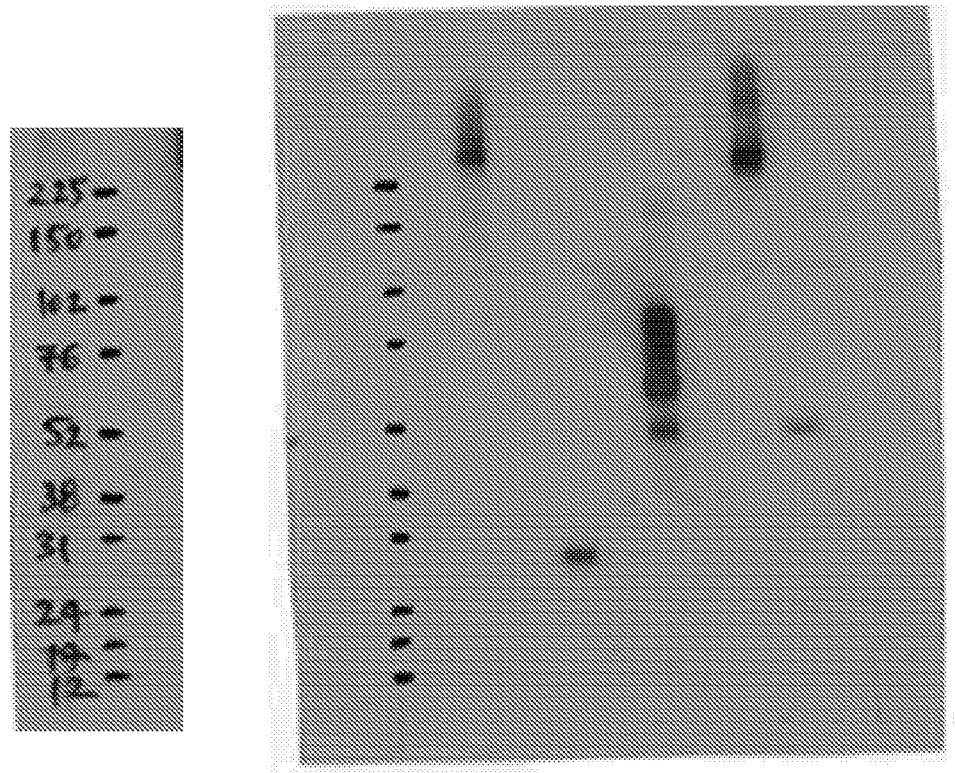
Figure 23:
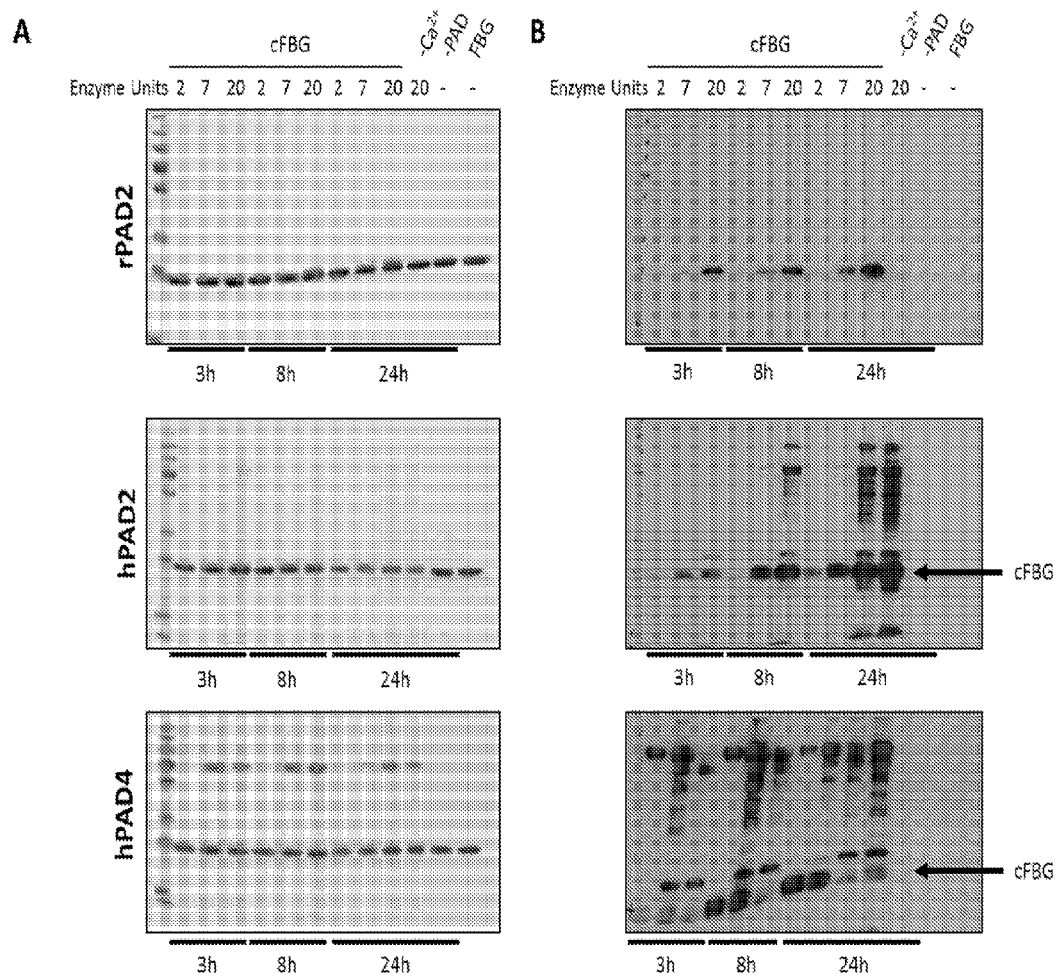
Figure 24:
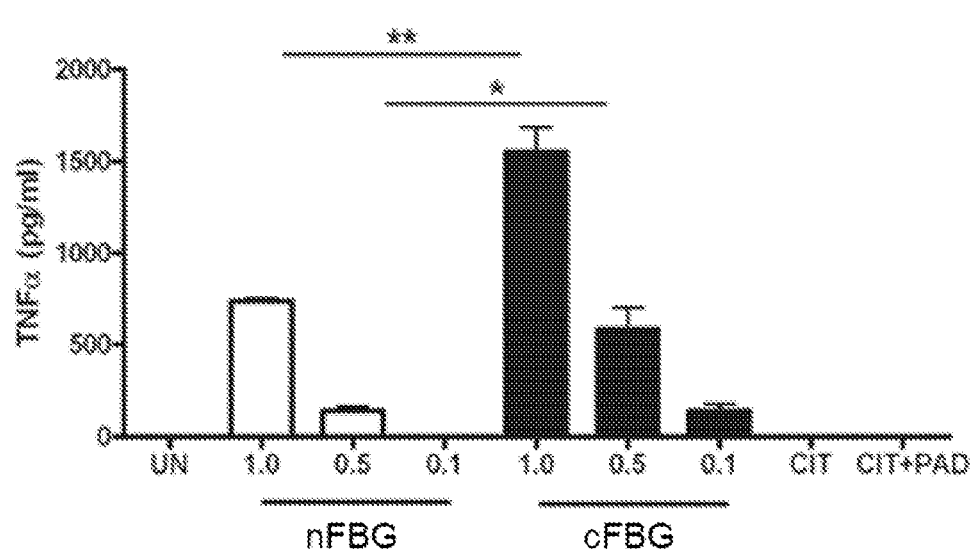
Figure 25:
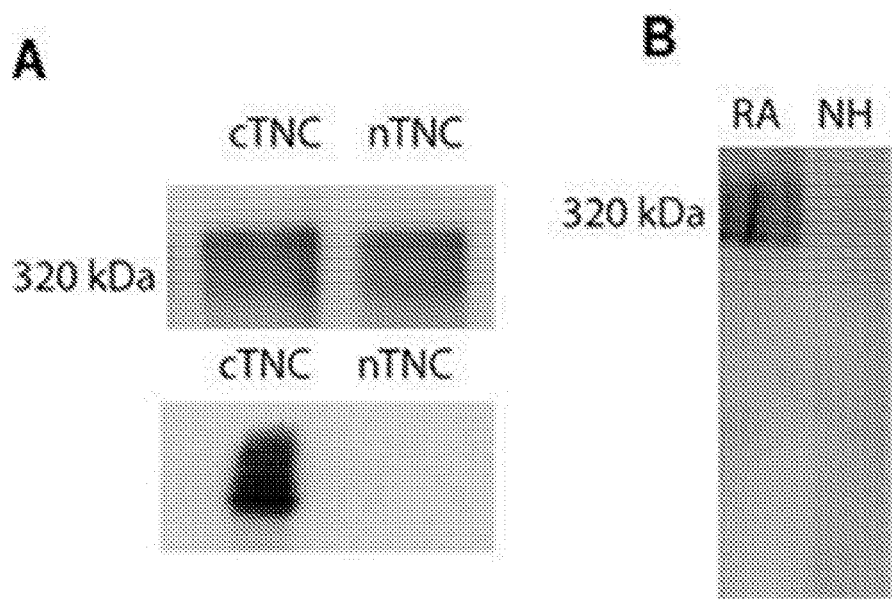
FIG. 25A shows a coomassie stained gel of native (nTNC) and citrullinated (cTNC) purified human recombinant tenascin-C (top panel) and citrullination of tenascin-C demonstrated by western blot with the AMC (Anti-modified citrulline) kit (bottom panel).
FIG. 25B shows a representative western blot of cTNC probed with serum from RA patients (RA) or normal healthy controls (NH) (n=50). No reactivity was observed with any sera in blots of nTNC (not shown).
Figure 26:
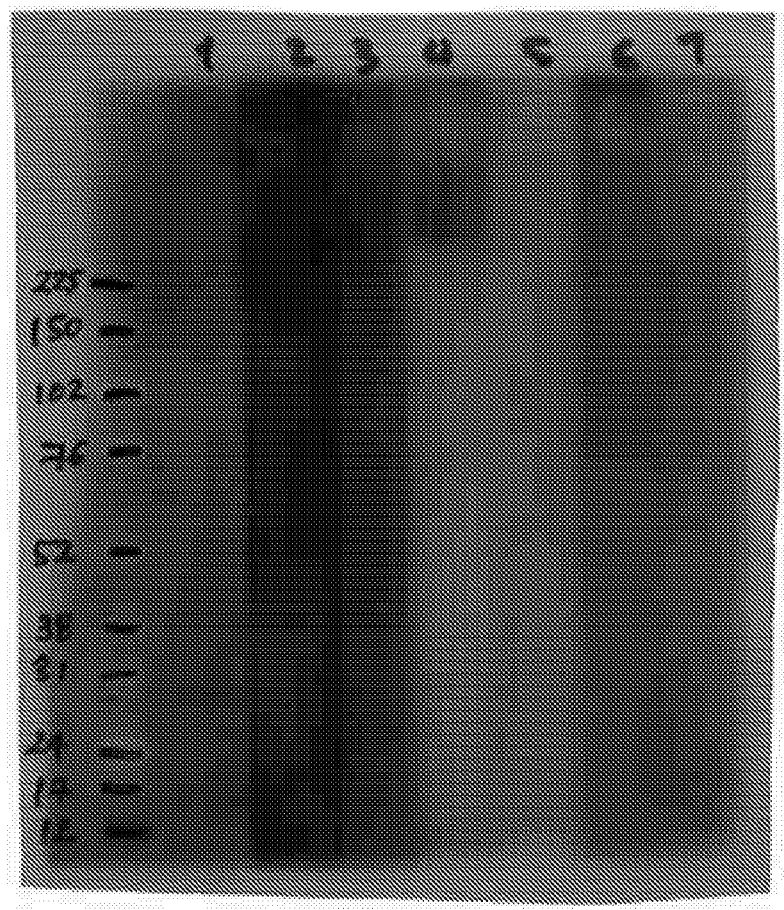
FIGS. 26 and 27 shows that serum from a subset of RA patients exhibits reactivity with citTNC (see RA patient sample in lane 4).
Figure 27:
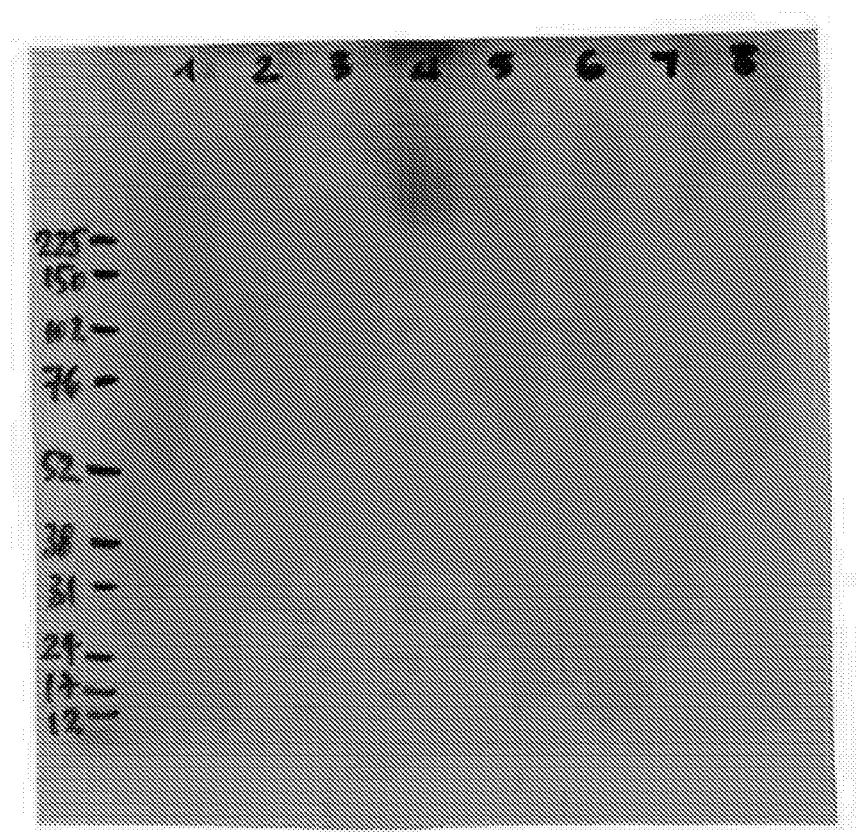
Figure 28:
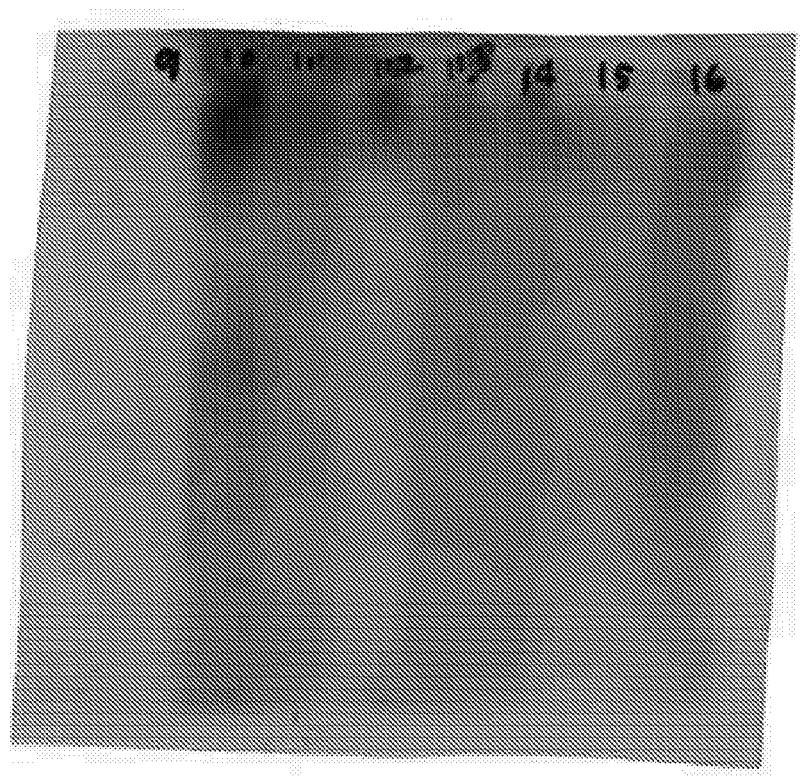
FIG. 28 shows that serum from normal healthy controls exhibit no reactivity with citTNC.
Figure 29:
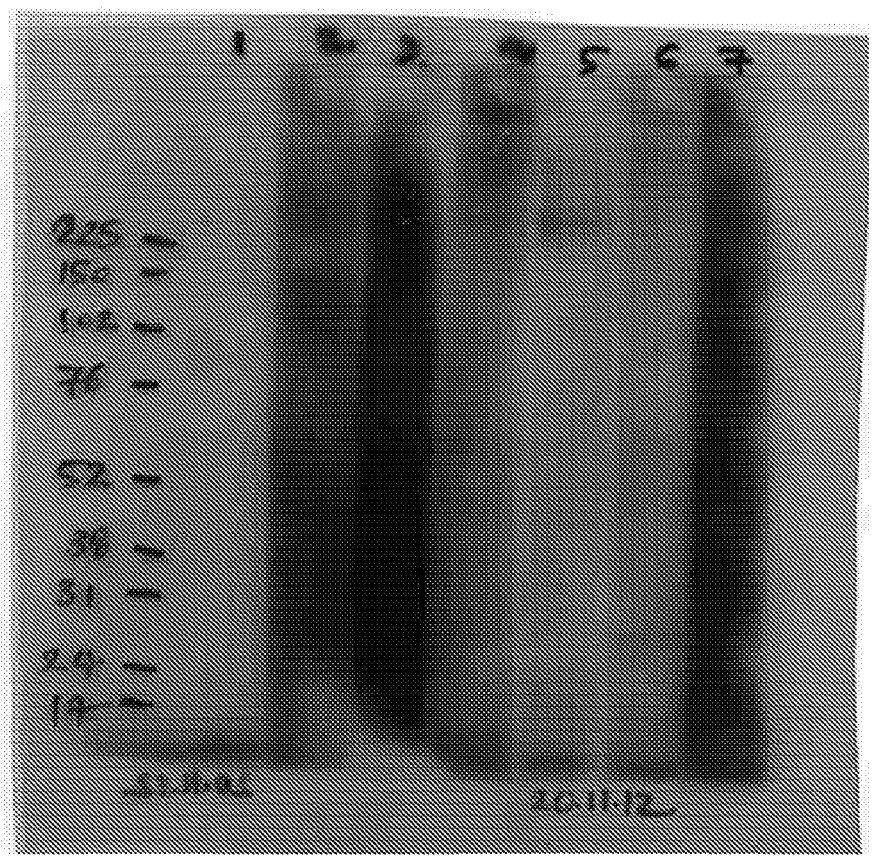

FIG. 29 shows RA serum against citrullinated tenascin-C and citrullinated FBG. A western blot of cTNC plus cFBG was run together in the same well, probed with serum from 7 different RA patients. Patient subsets were observed that reacted with full length tenascin-C (320 kD) but not FBG (lanes 4, 5) or patients that reacted with citrullinated FBG (27 kd) but not full length tenascin-C (lane 6).

Gels run with full length citrullinated tenascin-C and with citrullinated FBG in the same lane show some patients react with full length tenascin-C. Of those that do react with tenascin-C only a subset also react with FBG thus they must by definition recognize a different domain.

EXAMPLE 11

Defining the Sites of Citrullination by LC-MS/MS

Figure 30:
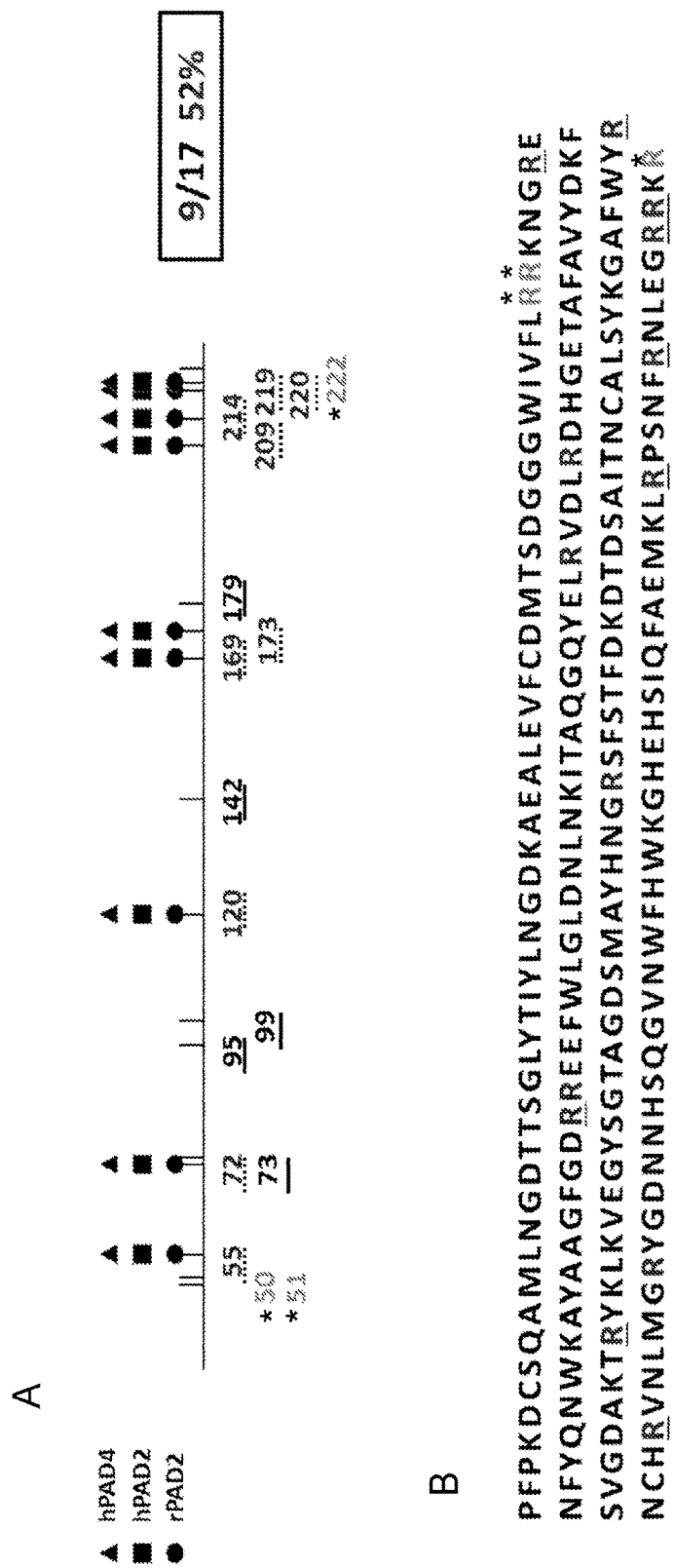

With reference to FIG. 30 and table 3, citrullinated arginine residues were identifed by LC-MS/MS. From 17 Arginines, 5 are not citrullinated, 3 arginines are not covered by this LC-MS/MS analysis, and 9 arginine residues are modified to citrulline residues, independent of the enzyme used for citrullination.

TABLE 3

| Position R | Sequence | m/z | Charge |
|---|---|---|---|
| 55 | NGR(+.98)ENFYQNWK [SEQ ID NO: 33] | 728.8331 | 2+ |
| 72 | AYAAGFGDR(+.98)R [SEQ ID NO: 34] | 542.7619 | 2+ |

TABLE 3-continued

| Position R | Sequence | m/z | Charge |
|---|---|---|---|
| 120 | TR(+.98)YKLK [SEQ ID NO: 35] | 405.2478 | 2+ |
| 169 | GAFWYR(+.98)RNC(+57.02)HR [SEQ ID NO: 36] | 684.3063 | 2+ |
| 173 | NC(+57.02)HR(+.98)VNLM(+15.99)GR [SEQ ID NO: 37] | 637.2995 | 2+ |
| 173 | NC(+57.02)HR(+.98)VNLMGR [SEQ ID NO: 38] | 629.3023 | 2+ |
| 173 | NC(+57.02)HR(+.98)VNLM(+15.99)GR [SEQ ID NO: 39] | 425.2011 | 3+ |
| 173 | N(+27.99)C(+57.02)HR(+.98)VNLMGR [SEQ ID NO: 40] | 643.2988 | 2+ |
| 209 | L(+57.02)R(+.98)PSNFR [SEQ ID NO: 41] | 474.2563 | 2+ |
| 214 | L(+27.99)RPSNFR(+.98)NLEGR [SEQ ID NO: 42] | 744.3896 | 2+ |
| 214 | LRPSNFR(+.98)NLEGR [SEQ ID NO: 43] | 730.3915 | 2+ |
| 214 | LRPSN(+.98)FR(+.98)NLEGR [SEQ ID NO: 44] | 487.5948 | 3+ |
| 214 | L(+27.99)RPSNFR(+.98)NLEGR [SEQ ID NO: 45] | 496.5952 | 3+ |
| 214 | LRPSNFR(+.98)NLEGRR [SEQ ID NO: 46] | 404.7247 | 4+ |
| 214 | LRPSNFR(+.98)NLEGR [SEQ ID NO: 47] | 487.2641 | 3+ |
| 219 | N(+27.99)LEGR(+.98)RK [SEQ ID NO: 48] | 451.2462 | 2+ |
| 219 | L(+27.99)RPSNFRNLEGR(+.98)R [SEQ ID NO: 49] | 548.6292 | 3+ |
| 214/219 | LRPSN(+.98)FR(+.98)NLEGR(+.98)R [SEQ ID NO: 50] | 539.9565 | 3+ |
| 214/219 | LRPSNFR(+.98)NLEGR(+.98) [SEQ ID NO: 51] | 730.8856 | 2+ |
| 214/219 | LRPSNFR(+.98)NLEGR(+.98)R [SEQ ID NO: 52] | 808.9345 | 2+ |
| 214/219 | LRPSNFR(+.98)NLEGR(+.98)R [SEQ ID NO: 53] | 539.6262 | 3+ |

EXAMPLE 12

Identifying the Citrullinated Antibody Epitope

Figure 31:
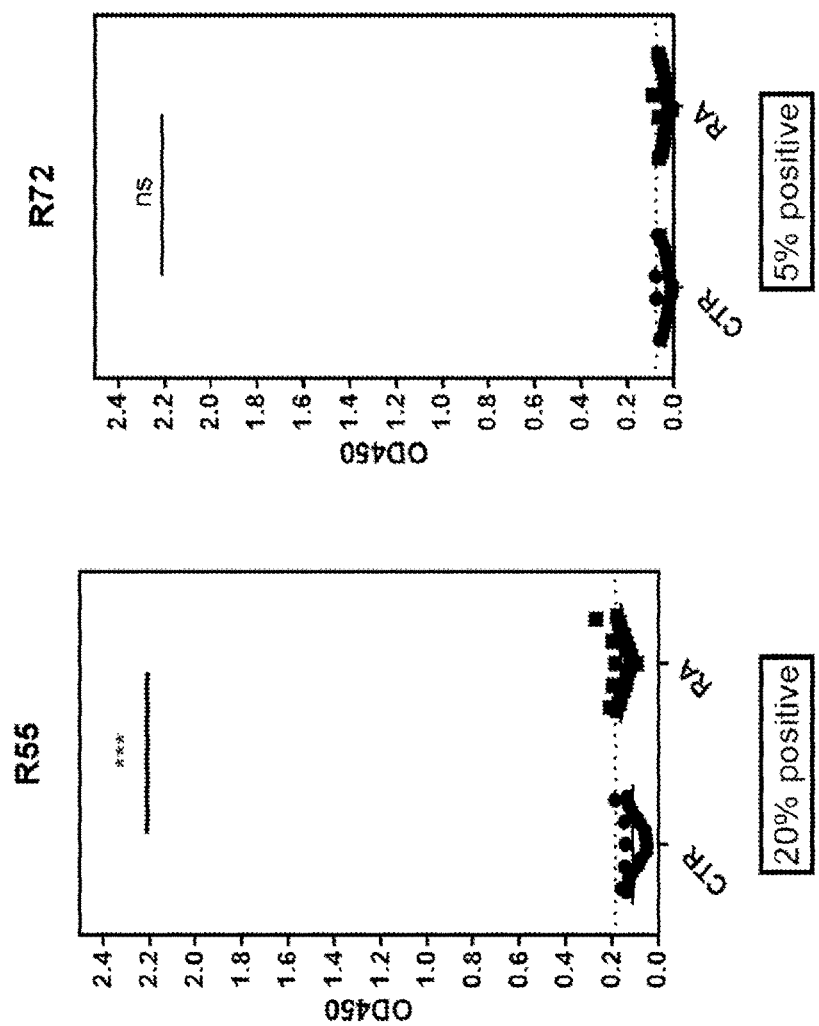
Figure 31:
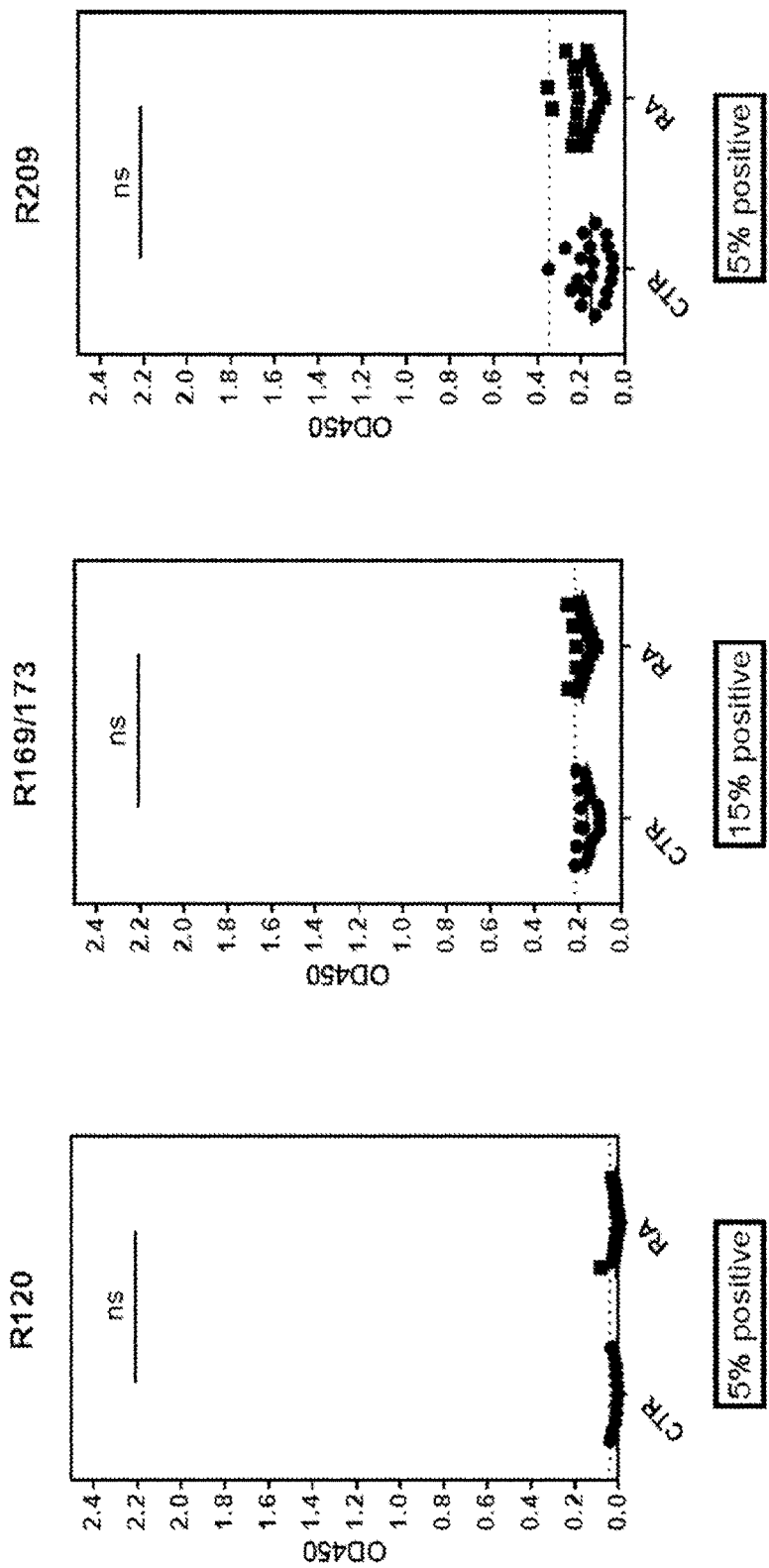
Figure 31:
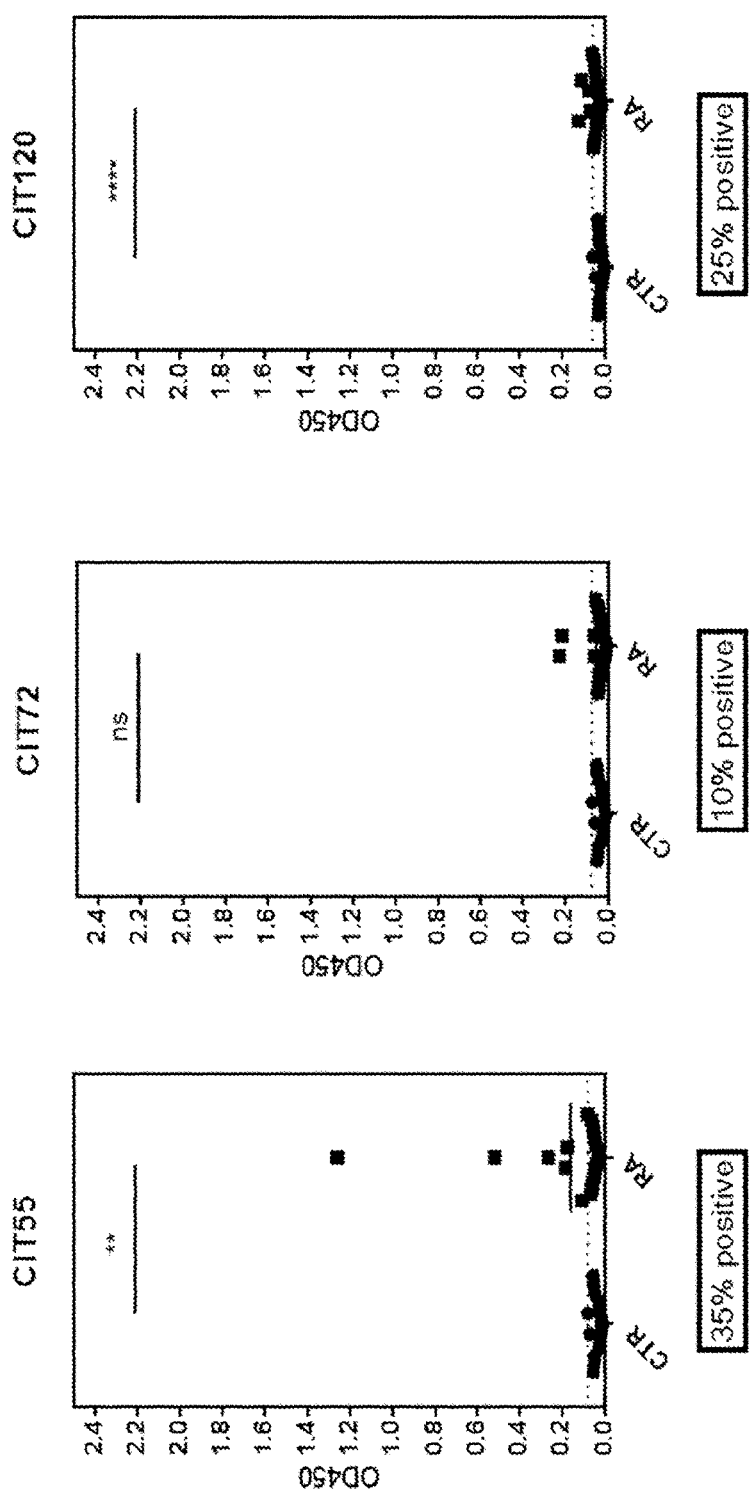
Figure 31:
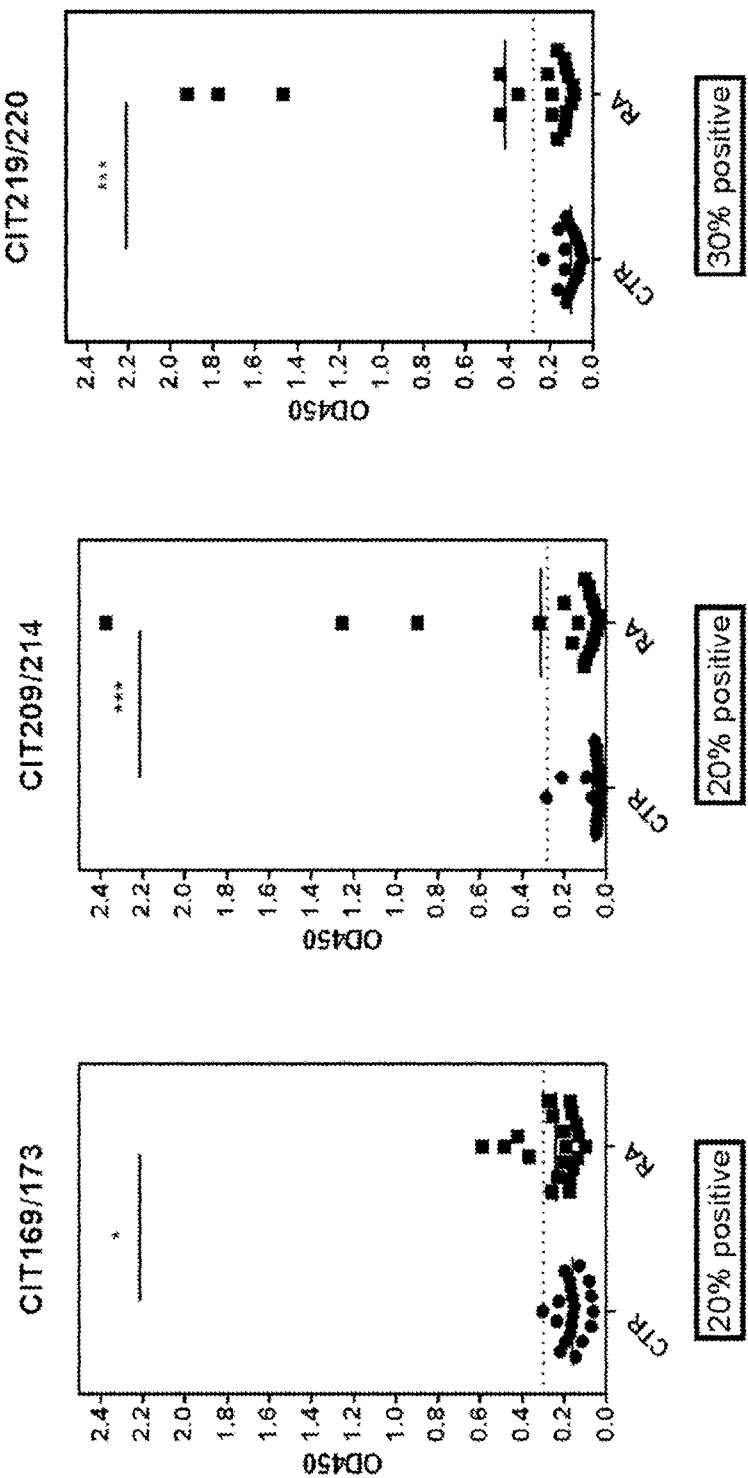

With reference to FIG. 31, the antibody response in 20 RA and 20 control sera to 6 cyclic FBG peptides, encompassing citrulline residues was evaluated.

The peptides evaluated where as follows:

R55:
[SEQ ID NO: 54]
CVFLRRKNG-R-ENFYQNWC

CIT55:
[SEQ ID NO: 55]
CVFLRRKNG-Cit-ENFYQNWC

R72:
[SEQ ID NO: 56]
CAYAAGFGD-R-REEFWLGLC

CIT72:
[SEQ ID NO:57]
CAYAAGFGD-Cit-REEFWLGLC

R120:
[SEQ ID NO: 58]
CFSVGDAKT-R-YKLKVEGYC

CIT120:
[SEQ ID NO: 59]
CFSVGDAKT-Cit-YKLKVEGYC

R169/173:
[SEQ ID NO: 60]
CKGAFWY-R-NCH-R-VNLMGRC

CIT169/173:
[SEQ ID NO: 61]
CKGAFWY-Cit-NCH-Cit-VNLMGRC

R209/214/219/220:
[SEQ ID NO: 62]
CEMKL-R-PSNF-R-NLEG-R-R-KRC

CIT209/214:
[SEQ ID NO: 63]
CEMKL-Cit-PSNF-Cit-NLEGRRKRC

CIT219/220:
[SEQ ID NO: 64]
CEMKLRPSNFRNLEG-Cit-Cit-KRC

A strong antibody response towards citrulline containing peptides CIT55, CIT209/214 and CIT219/220 was detected in RA sera but not control sera, and no response was observed against arginine containing control peptides. Data from this small cohort shows that about 35% of RA patients will be positive for the CIT55 epitope, 20% for the CIT 209/214 and 30% for the CIT219/220 whilst none of the healthy controls exhibited positivity, defined using the 95th percentile of the normal group. The same calculations may be used to diagnose RA compared to a group of healthy controls and a similar percentage in these groups may be expected.

These data will enable the stratification of patients based on citFBG antibody positivity or on citFBG positivity. Those patients that were positive would be candidates for treatment with any agents designed to target the activity of citrullinated FBG. The presence of different epitopes also informs how to target citFBG—e.g. if CIT55 was present treatment may comprise blocking the immunogenic activity of FBG, but if the integrin binding site was citrullinated treatment may comprise blocking the action of this domain.

EXAMPLE 13

Citrullination of FBG Reduces Cell Adhesion of HDF and RAF

Figure 32:
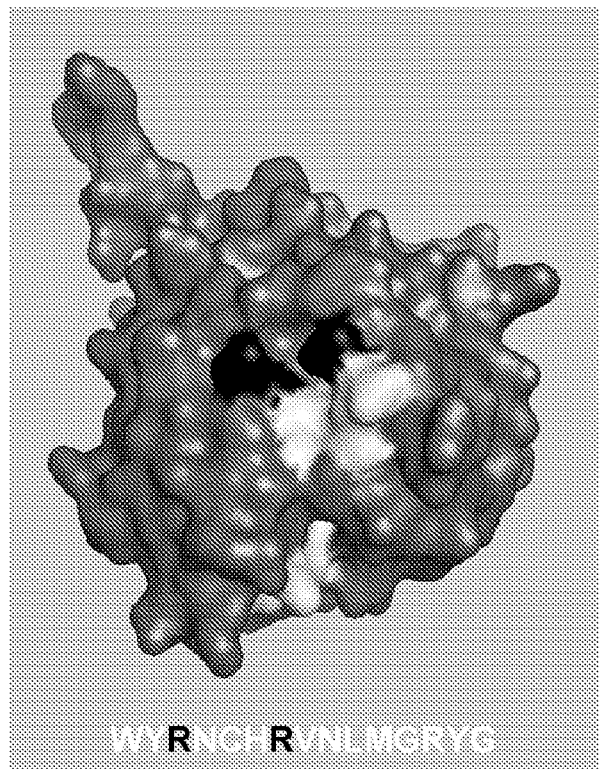
Figure 32:
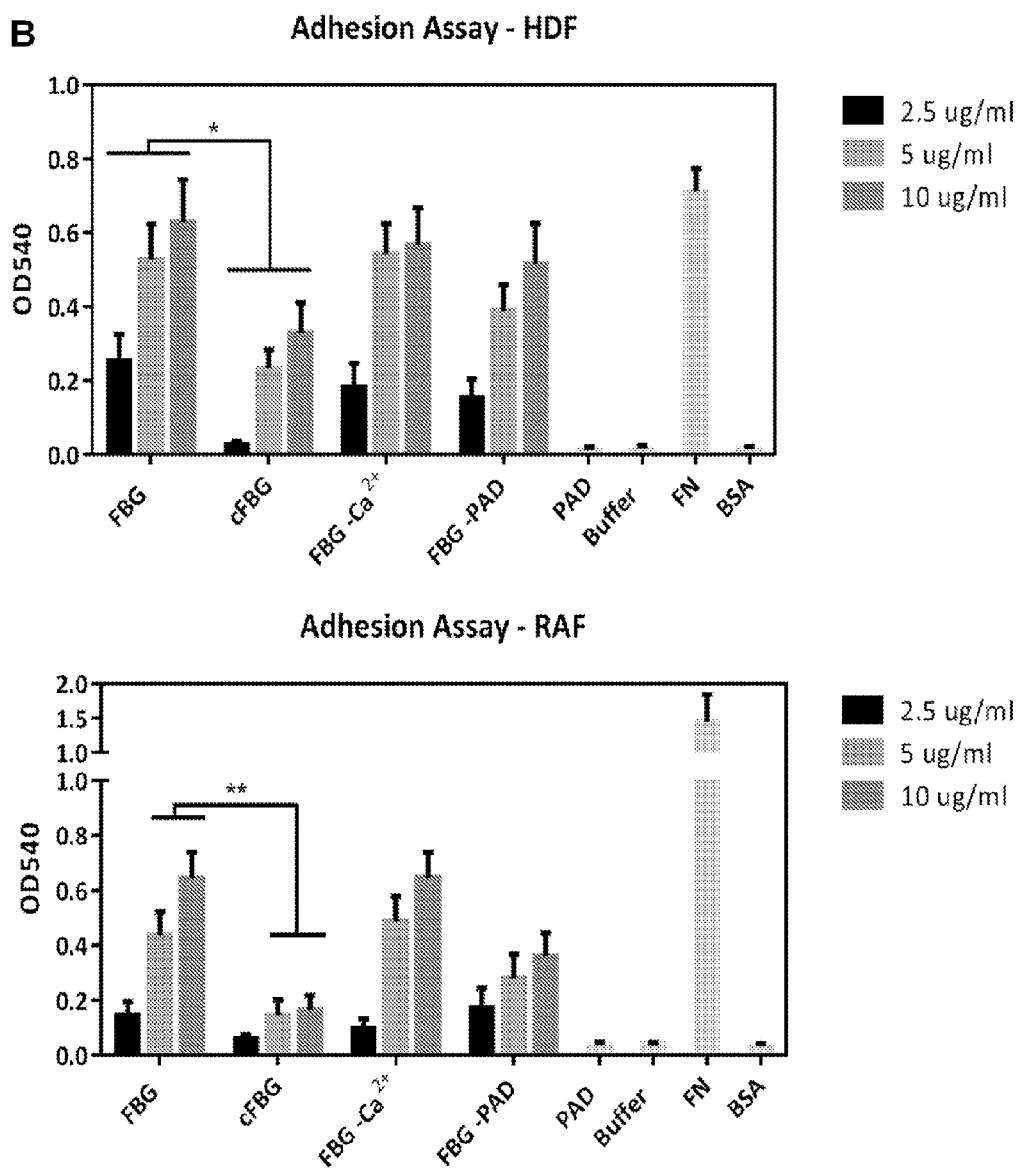

With reference to FIG. 32, FBG is proadhesive for human dermal fibroblasts (HDF) and synovial fibroblasts from RA joints (RAF). Citrullination of FBG reduces adhesion of HDF and RAF. Two arginines within the sequence known to bind integrin αvβ3 are citrullinated, therefore reduced adhesion may be due to reduced binding of cFBG to integrin αvβ3. Yokoyama et al. determined that this peptide sequence within FBG mediates cell adhesion via binding to cell surface αvβ3 integrins. Here it is shown 1) citrullination occurs in vitro in the integrin binding site, 2) this reduces cell adhesion, and 3) this happens in RASF meaning that, in an RA joint, citrullination of FBG at this site may reduce the adhesion of RASF. This can have many implications for disease progression, for example, it may promote cell migration (e.g. invasion into and degradation of healthy joint tissue), and it may facilitate RASF proliferation (thus perpetuating synovial hyperplasia).

REFERENCES

1. Smolen, J. S. & Maini, R. N. Interleukin-6: a new therapeutic target. *Arthritis Res Ther* 8 Suppl 2, S5 (2006).
2. Williams, R. O., Paleolog, E. & Feldmann, M. Cytokine inhibitors in rheumatoid arthritis and other autoimmune diseases. *Curr Opin Pharmacol* 7, 412-417 (2007).
3. Brentano, F., Kyburz, D., Schorr, O., Gay, R. & Gay, S. The role of Toll-like receptor signalling in the pathogenesis of arthritis. *Cell Immunol* 233, 90-96 (2005).
4. O'Neill, L. A. Primer: Toll-like receptor signaling pathways-what do rheumatologists need to know? *Nat Clin Pract Rheumatol* (2008).
5. Matzinger, P. The danger model: a renewed sense of self. *Science* 296, 301-305 (2002).
6. Bianchi, M. E. DAMPs, PAMPs and alarmins: all we need to know about danger. *J Leukoc Biol* 81, 1-5 (2007).
7. Gordon, S. Pattern recognition receptors: doubling up for the innate immune response. *Cell* 111, 927-930 (2002).
8. Medzhitov, R. & Janeway, C. A., Jr. Decoding the patterns of self and nonself by the innate immune system. *Science* 296, 298-300 (2002).
9. Radstake, T. R., et al. Expression of toll-like receptors 2 and 4 in rheumatoid synovial tissue and regulation by proinflammatory cytokines interleukin-12 and interleukin-18 via interferon-gamma. *Arthritis Rheum* 50, 3856-3865 (2004).
10. Roelofs, M. F., et al. The expression of toll-like receptors 3 and 7 in rheumatoid arthritis synovium is increased and costimulation of toll-like receptors 3, 4, and 7/8 results in synergistic cytokine production by dendritic cells. *Arthritis Rheum* 52, 2313-2322 (2005).
11. Sacre, S. M., et al. The Toll-like receptor adaptor proteins MyD88 and Mal/TIRAP contribute to the inflammatory and destructive processes in a human model of rheumatoid arthritis. *Am J Pathol* 170, 518-525 (2007).
12. Choe, J. Y., Crain, B., Wu, S. R. & Corr M. Interleukin 1 receptor dependence of serum transferred arthritis can be circumvented by toll-like receptor 4 signaling. *J Exp Med* 197, 537-542 (2003).
13. Lee, E. K., Kang, S. M., Paik, D. J., Kim, J. M. & Youn, J. Essential roles of Toll-like receptor-4 signaling in arthritis induced by type II collagen antibody and LPS. *Int Immunol* 17, 325-333 (2005).
14. Abdollahi-Roodsaz, S., et al. Inhibition of Toll-like receptor 4 breaks the inflammatory loop in autoimmune destructive arthritis. *Arthritis Rheum* 56, 2957-2967 (2007).
15. Vanags, D., et al. Therapeutic efficacy and safety of chaperonin 10 in patients with rheumatoid arthritis: a double-blind randomised trial. *Lancet* 368, 855-863 (2006).
16. Chiquet-Ehrismann, R. & Chiquet, M. Tenascins: regulation and putative functions during pathological stress. *J Pathol* 200, 488-499 (2003).
17. Cutolo, M., Picasso, M., Ponassi, M., Sun, M. Z. & Balza, E. Tenascin and fibronectin distribution in human normal and pathological synovium. *J Rheumatol* 19, 1439-1447 (1992).
18. McCachren, S. S. & Lightner, V. A. Expression of human tenascin in synovitis and its regulation by interleukin-1. *Arthritis Rheum* 35, 1185-1196 (1992).
19. Salter, D. M. Tenascin is increased in cartilage and synovium from arthritic knees. *Br J Rheumatol* 32, 780-786 (1993).
20. Chevalier, X., Groult, N., Larget-Piet, B., Zardi, L. & Hornebeck, W. Tenascin distribution in articular cartilage from normal subjects and from patients with osteoarthritis and rheumatoid arthritis. *Arthritis Rheum* 37, 1013-1022 (1994).
21. Hasegawa, M., et al. Expression of large tenascin-C splice variants in synovial fluid of patients with rheumatoid arthritis. *J Orthop Res* 25, 563-568 (2007).
22. Orend, G. Potential oncogenic action of tenascin-C in tumorigenesis. *Int J Biochem Cell Biol* 37, 1066-1083 (2005).
23. Brackertz, D., Mitchell, G. F. & Mackay, I. R. Antigen-induced arthritis in mice. I. Induction of arthritis in various strains of mice. *Arthritis Rheum* 20, 841-850 (1977).
24. Brennan, F. M., Chantry, D., Jackson, A., Maini, R. & Feldmann, M. Inhibitory effect of TNF alpha antibodies on synovial cell interleukin-1 production in rheumatoid arthritis. *Lancet* 2, 244-247 (1989).
25. Smiley, S. T., King, J. A. & Hancock, W. W. Fibrinogen stimulates macrophage chemokine secretion through toll-like receptor 4. *J Immunol* 167, 2887-2894 (2001).
26. Fitzgerald, K. A., Rowe, D. C. & Golenbock, D. T. Endotoxin recognition and signal transduction by the TLR4/MD2-complex. *Microbes Infect* 6, 1361-1367 (2004).
27. Jiang, Z., et al. CD14 is required for MyD88-independent LPS signaling. *Nat Immunol* 6, 565-570 (2005).
28. Coats, S. R., Do, C. T., Karimi-Naser, L. M., Braham, P. H. & Darveau, R. P. Antagonistic lipopolysaccharides block *E. coli* lipopolysaccharide function at human TLR4 via interaction with the human MD-2 lipopolysaccharide binding site. *Cell Microbiol* 9, 1191-1202 (2007).
29. Siri, A., et al. Human tenascin: primary structure, pre-mRNA splicing patterns and localization of the epitopes recognized by two monoclonal antibodies. *Nucleic Acids Res* 19, 525-531 (1991).
30. Gondokaryono, S. P., et al. The extra domain A of fibronectin stimulates murine mast cells via toll-like receptor 4. *J Leukoc Biol* 82, 657-665 (2007).
31. Taylor, K. R., et al. Recognition of hyaluronan released in sterile injury involves a unique receptor complex dependent on Toll-like receptor 4, CD44, and MD-2. *J Biol Chem* 282, 18265-18275 (2007).
32. Kim, H. M., et al. Crystal structure of the TLR4-MD-2 complex with bound endotoxin antagonist Eritoran. *Cell* 130, 906-917 (2007).
33. Schaefer, L., et al. The matrix component biglycan is proinflammatory and signals through Toll-like receptors 4 and 2 in macrophages. *J Clin Invest* 115, 2223-2233 (2005).
34. Foell, D., Wittkowski, H. & Roth, J. Mechanisms of disease: a 'DAMP' view of inflammatory arthritis. *Nat Clin Pract Rheumatol* 3, 382-390 (2007).

35. Taniguchi, N., et al. High mobility group box chromosomal protein 1 plays a role in the pathogenesis of rheumatoid arthritis as a novel cytokine. *Arthritis Rheum* 48, 971-981 (2003).
36. Pullerits, R., et al. High mobility group box chromosomal protein 1, a DNA binding cytokine, induces arthritis. *Arthritis Rheum* 48, 1693-1700 (2003).
37. Kokkola, R., et al. Successful treatment of collagen-induced arthritis in mice and rats by targeting extracellular high mobility group box chromosomal protein 1 activity. *Arthritis Rheum* 48, 2052-2058 (2003).
38. Gutowski, N. J., Newcombe, J. & Cuzner, M. L. Tenascin-R and C in multiple sclerosis lesions: relevance to extracellular matrix remodelling. *Neuropathol Appl Neurobiol* 25, 207-214 (1999).
39. Amin, K., et al. Inflammation and structural changes in the airways of patients with primary Sjogren's syndrome. *Respir Med* 95, 904-910 (2001).
40. Loots, M. A., et al. Differences in cellular infiltrate and extracellular matrix of chronic diabetic and venous ulcers versus acute wounds. *J Invest Dermatol* 111, 850-857 (1998).
41. Lange, K., et al. Endothelin receptor type B counteracts tenascin-C-induced endothelin receptor type A-dependent focal adhesion and actin stress fiber disorganization. *Cancer Res* 67, 6163-6173 (2007).
42. Saga, Y., Yagi, T., Ikawa, Y., Sakakura, T. & Aizawa, S. Mice develop normally without tenascin. *Genes Dev* 6, 1821-1831 (1992).
43. Hoshino, K., et al. Cutting edge: Toll-like receptor 4 (TLR4)-deficient mice are hyporesponsive to lipopolysaccharide: evidence for TLR4 as the Lps gene product. *J Immunol* 162, 3749-3752 (1999).
44. Takeuchi, O., et al. Differential roles of TLR2 and TLR4 in recognition of gram-negative and gram-positive bacterial cell wall components. *Immunity* 11, 443-451 (1999).
45. Keystone, E. C., Schorlemmer, H. U., Pope, C. & Allison, A. C. Zymosan-induced arthritis: a model of chronic proliferative arthritis following activation of the alternative pathway of complement. *Arthritis Rheum* 20, 1396-1401 (1977).
46. van Lent, P. L., et al. Fcgamma receptors directly mediate cartilage, but not bone, destruction in murine antigen-induced arthritis: uncoupling of cartilage damage from bone erosion and joint inflammation. *Arthritis Rheum* 54, 3868-3877 (2006).
47. Foxwell, B., et al. Efficient adenoviral infection with IkappaB alpha reveals that macrophage tumor necrosis factor alpha production in rheumatoid arthritis is NF-kappaB dependent. *Proc Natl Acad Sci USA* 95, 8211-8215 (1998).
48. Kurt-Jones, E. A., et al. Use of murine embryonic fibroblasts to define Toll-like receptor activation and specificity. *J Endotoxin Res* 10, 419-424 (2004).
49. Todaro, G. J. & Green, H. Quantitative studies of the growth of mouse embryo cells in culture and their development into established lines. *J Cell Biol* 17, 299-313 (1963).
50. Butler, D. M., Malfait, A. M., Maini, R. N., Brennan, F. M. & Feldmann, M. Anti-IL-12 and anti-TNF antibodies synergistically suppress the progression of murine collagen-induced arthritis. *Eur J Immunol* 29, 2205-2212 (1999).
51. Ho, S. N., Hunt, H. D., Horton, R. M., Pullen, J. K. & Pease, L. R. Site-directed mutagenesis by overlap extension using the polymerase chain reaction. *Gene* 77, 51-59 (1989).
52. Clark, R. A., Erickson, H. P. & Springer, T. A. Tenascin supports lymphocyte rolling. *J Cell Biol* 137, 755-765 (1997).
53. El-Karef, A., et al. Deficiency of tenascin-C attenuates liver fibrosis in immune-mediated chronic hepatitis in mice. *J Pathol* 211, 86-94 (2007).
54. Loike, J. D., Cao, L., Budhu, S., Hoffman, S. & Silverstein, S. C. Blockade of alpha 5 beta 1 integrins reverses the inhibitory effect of tenascin on chemotaxis of human monocytes and polymorphonuclear leukocytes through three-dimensional gels of extracellular matrix proteins. *J Immunol* 166, 7534-7542 (2001).
55. Talts, J. F., Wirl, G., Dictor, M., Muller, W. J. & Fassler, R. tenascin-C modulates tumor stroma and monocyte/macrophage recruitment but not tumor growth or metastasis in a mouse strain with spontaneous mammary cancer. *J Cell Sci* 112 (Pt 12), 1855-1864 (1999).
56. Jones (2000) *Matrix Biol.*, 19, 581-96
57. Harandl (2009) Expert Review of Vaccines, 8, 293-298
58. McIntyre (2006) *BMC Biotechnol.* 6: 1
59. Paddison (2002) *Genes Dev.* 16 (8): 948-58
60. Andreakos (2004) Blood, 103, 2229-37
61. Goh, F. G., Piccinini, A. M., Krausgruber, T., Udalova, I. A. & Midwood, K. S. Transcriptional regulation of the endogenous danger signal tenascin-C: a novel autocrine loop in inflammation. *J Immunol* 184, 2655-2662 (2010).
62. Midwood, K. et al. Tenascin-C is an endogenous activator of Toll-like receptor 4 that is essential for maintaining inflammation in arthritic joint disease. *Nat Med* 15, 774-780 (2009).
63. LaFleur, D. W. et al. Aortic smooth muscle cells interact with tenascin-C through its fibrinogen-like domain. *J Biol Chem* 272, 32798-32803 (1997).
64. Taylor, P. C. & Feldmann, M. Anti-TNF biologic agents: still the therapy of choice for rheumatoid arthritis. *Nat Rev Rheumatol* 5, 578-582 (2009).
65. Yokoyama, K., Erickson, H. P., Ikeda, Y. & Takada, Y. Identification of amino acid sequences in fibrinogen gamma-chain and tenascin C C-terminal domains critical for binding to integrin alpha vbeta 3. *J Biol Chem* 275, 16891-16898 (2000).
66. Sacre S M, Lo A, Gregory B, Simmonds R E, Williams L, Feldmann M, Brennan F M, Foxwell B M. J Immunol. 2008 Dec. 1; 181(11):8002-9.
67. Wegner N, Lundberg K, Kinloch A, Fisher B, Malmstrom V, Feldmann M, Venables P J: Autoimmunity to specific citrullinated proteins gives the first clues to the etiology of rheumatoid arthritis. *Immunol Rev* 2010, 233: 34-54.
68. Fisher B A, Plant D, Brode M, van Vollenhoven R F, Mathsson L, Symmons D, Lundberg K, Ronnelid J, Venables P J: Antibodies to citrullinated alpha-enolase peptide 1 and clinical and radiological outcomes in rheumatoid arthritis. *Ann Rheum Dis* 2011, 70:1095-1098.
69. Kinloch A, Tatzer V, Wait R, Peston D, Lundberg K, Donatien P, Moyes D, Taylor P C, Venables P J: Identification of citrullinated alpha-enolase as a candidate autoantigen in rheumatoid arthritis. *Arthritis Res Ther* 2005, 7:R1421-1429.
70. Kinloch A J, Alzabin S, Brintnell W, Wilson E, Barra L, Wegner N, Bell D A, Cairns E, Venables P J: Immunization with *Porphyromonas gingivalis* enolase induces autoimmunity to mammalian alpha-enolase and arthritis in DR4-I E-transgenic mice. *Arthritis Rheum* 2011, 63:3818-3823.
71. Lundberg K, Kinloch A, Fisher B A, Wegner N, Wait R, Charles P, Mikuls T R, Venables P J: Antibodies to 71. citrullinated alpha-enolase peptide 1 are specific for rheumatoid arthritis and cross-react with bacterial enolase. *Arthritis Rheum* 2008, 58:3009-3019.
72. Snir O, Widhe M, Hermansson M, von Spee C, Lindberg J, Hensen S, Lundberg K, Engstrom A, Venables P J, Toes R E, Holmdahl R, Klareskog L, Malmstrom V: Antibodies to several citrullinated antigens are enriched in the joints of rheumatoid arthritis patients. *Arthritis Rheum* 2010, 62:44-52.
73. Snir O, Widhe M, von Spee C, Lindberg J, Padyukov L, Lundberg K, Engstrom A, Venables P J, Lundeberg J, Holmdahl R, Klareskog L, Malmstrom V: Multiple antibody reactivities to citrullinated antigens in sera from patients with rheumatoid arthritis: association with HLA-DRB1 alleles. *Ann Rheum Dis* 2009, 68:736-743.
74. Wegner N, Wait R, Sroka A, Eick S, Nguyen K A, Lundberg K, Kinloch A, Culshaw S, Potempa J, Venables P J: Peptidylarginine deiminase from *Porphyromonas gingivalis* citrullinates human fibrinogen and alpha-enolase: implications for autoimmunity in rheumatoid arthritis. *Arthritis Rheum* 2010, 62:2662-2672.
75. Kuhn K A, Kulik L, Tomooka B, Braschler K J, Arend W P, Robinson W H, Holers V M: Antibodies against citrullinated proteins enhance tissue injury in experimental autoimmune arthritis. *J Clin Invest* 2006, 116:961-973.
76. Uysal H, Bockermann R, Nandakumar K S, Sehnert B, Bajtner E, Engstrom A, Serre G, Burkhardt H, Thunnissen M M, Holmdahl R: Structure and pathogenicity of antibodies specific for citrullinated collagen type I I in experimental arthritis. *J Exp Med* 2009, 206:449-462.
77. Clavel C, Nogueira L, Laurent L, lobagiu C, Vincent C, Sebbag M, Serre G: Induction of macrophage secretion of tumor necrosis factor alpha through Fcgamma receptor IIa engagement by rheumatoid arthritis-specific autoantibodies to citrullinated proteins complexed with fibrinogen. *Arthritis Rheum* 2008, 58:678-688. Page 10 of 10
78. Sokolove J, Zhao X, Chandra P E, Robinson W H: Immune complexes containing citrullinated fibrinogen costimulate macrophages via Toll-like receptor 4 and Fcgamma receptor. *Arthritis Rheum* 2011, 63:53-62.
79. Midwood K, Sacre S, Piccinini A M, Inglis J, Trebaul A, Chan E, Drexler S, Sofat N, Kashiwagi M, Orend G, Brennan F, Foxwell B: Tenascin-C is an endogenous activator of Toll-like receptor 4 that is essential for maintaining inflammation in arthritic joint disease. *Nat Med* 2009, 15:774-780.
80. Ruhmann M, Piccinini A M, Kong P L, Midwood K S: Endogenous activation of adaptive immunity: tenascin-C drives interleukin-17 synthesis in murine arthritic joint disease. *Arthritis Rheum* 2012, 64:2179-2190.
81. Goh F G, Piccinini A M, Krausgruber T, Udalova I A, Midwood K S: Transcriptional regulation of the endogenous danger signal tenascin-C: a novel autocrine loop in inflammation. *J Immunol* 2010, 184:2655-2662.
82. Page T H, Charles P J, Piccinini A M, Nicolaidou V, Taylor P C, Midwood K S: Raised circulating tenascin-C in rheumatoid arthritis. *Arthritis Res Ther* 2012, 14:R260.

The invention claimed is:

1. A method of detecting a citrullinated fibrinogen-like globe (FBG) domain of tenascin-C or a citrullinated fragment of the FBG domain of tenascin-C associated with the presence of rheumatoid arthritis (RA) in a subject, the method comprising:
   detecting in a biological sample obtained from the subject a citrullinated FBG domain of tenascin-C or a citrullinated fragment of the FBG domain of tenascin-C by (i) contacting the sample with an antibody that specifically binds to citrullinated arginine residues in the FBG domain of tenascin-C or to a citrullinated fragment of the FBG domain of, tenascin-C and detecting binding of the antibody to the citrullinated FBG domain of tenascin-C or to a citrullinated fragment of the FBG domain of tenascin-C; or by (ii) detecting a citrullinated FBG domain of tenascin-C or a citrullinated fragment of the FBG domain of tenascin-C using mass spectrometry.

2. The method of claim 1, further comprising measuring the level of (i) citrullinated fibrinogen-like globe (FBG) domain of tenascin-C or a citrullinated fragment of the FBG domain of tenascin-C in the sample by antibody binding or mass spectrometry relative to normal and/or reference values.

3. The method of claim 1, wherein the antibody that binds to said citrullinated arginine residues in the FBG domain of tenascin-C or to a citrullinated fragment of the FBG domain of tenascin-C is an immobilized antibody.

4. A method of monitoring the progression of rheumatoid arthritis (RA) in a subject or monitoring the efficacy of treatment for RA administered to a subject, the method comprising:

(a) detecting in a biological sample obtained from a subject at a first time point the levels of
      (i) citrullinated fibrinogen-like globe (FBG) domain of tenascin-C or a citrullinated fragment of the FBG domain of tenascin-C by measuring binding of said citrullinated FBG domain of tenascin-C or a citrullinated fragment of the FBG domain of tenascin-C in the subject's sample to an immobilized antibody directed against the citrullinated FBG domain of tenascin-C or a citrullinated fragment of the FBG domain of tenascin-C, relative to normal and/or reference values; and/or
      (ii) autoantibodies with specificity for binding to the citrullinated FBG domain of tenascin-C or to a citrullinated fragment of the FBG domain of tenascin-C by measuring binding of autoantibodies in the subject's sample to an immobilized citrullinated FBG domain of tenascin-C or to immobilized citrullinated FBG domain fragments of tenascin-C, relative to normal and/or reference values; and (b) detecting in a biological sample obtained from the subject at a second and, optionally, a subsequent, time point the levels of
      (i) citrullinated FBG domain of tenascin-C or citrullinated fragments of the FBG domain of tenascin-C as in step (a) (i) relative to reference values; and/or
      (ii) autoantibodies with specificity for the citrullinated FBG domain of tenascin-C or the citrullinated fragments of the FBG domain of tenascin-C as in step (a) (ii) relative to reference values.

5. The method of claim 4 wherein the reference values are the initial levels of (i) the citrullinated FBG domain of tenascin-C or the citrullinated fragments of the FBG domain of tenascin-C; and/or (ii) autoantibodies with specificity for the citrullinated FBG domain of tenascin-C or citrullinated fragments of the FBG domain of tenascin-C in the subject, or the levels of (i) the citrullinated FBG domain of tenascin-C or citrullinated fragments of the FBG domain of tenascin-C; and/or (ii) autoantibodies with specificity for the citrullinated FBG domain of tenascin-C or citrullinated fragments of the FBG domain of tenascin-C in the subject when they were previously tested, or both.

6. The method of claim 1, wherein the sample is selected from blood, serum, plasma, synovial fluid or joint tissue obtained from the subject.

7. The method of claim 4, further comprising:
  (c) detecting:
    (i) decreased levels of a citrullinated fibrinogen-like globe (FBG) domain of tenascin-C or a citrullinated fragment of the FBG domain of tenascin-C, and/or decreased levels of autoantibodies with specificity for a citrullinated FBG domain of tenascin-C or for a citrullinated fragment of the FBG domain of tenascin-C in the sample obtained at the second or subsequent time point relative to the levels in the sample obtained at the first time point as indicative of reduced progression of RA in the subject or of effective treatment of RA in the subject; or
    (ii) increased levels of a citrullinated fibrinogen-like globe (FBG) domain of tenascin-C or a citrullinated fragment of the FBG domain of tenascin-C, and/or increased levels of autoantibodies with specificity for a citrullinated fibrinogen-like globe (FBG) domain of tenascin-C or a citrullinated fragment of the FBG domain of tenascin-C in the sample obtained at the second or subsequent time point relative to the levels in the sample obtained at the first time point as indicative of progression of RA in the subject or of ineffective treatment of RA in the subject.

8. The method of claim 4, wherein the antibody is immobilized on a support and/or the citrullinated FBG domain of tenascin-C and/or a citrullinated fragment of the FBG domain of tenascin-C is immobilized on a support.

9. The method of claim 4, wherein the sample is selected from blood, serum, plasma, synovial fluid or joint tissue obtained from the subject.

10. A method of detecting autoantibodies against a citrullinated fibrinogen-like globe (FBG) domain of tenascin-C and/or a citrullinated fragment of the FBG domain of tenascin-C associated with rheumatoid arthritis (RA) in a subject, the method comprising:
  (a) contacting a biological sample obtained from the subject with citrullinated FBG domain of tenascin-C and/or a citrullinated fragment of the FBG domain of tenascin-C attached to or immobilized on a support; and
  (b) detecting autoantibodies against the citrullinated FBG domain of tenascin-C and/or against a citrullinated fragment of the FBG domain of tenascin-C by detecting specific binding of the attached or immobilized citrullinated FBG domain of tenascin-C and/or the immobilized citrullinated fragment of the FBG domain of tenascin-C to the autoantibodies in the sample.

11. The method of claim 10, wherein the binding is detected by one or more of immunoassay, spectrometry, immunosorbent assay, enzyme linked immunosorbent assay (ELISA), sandwich ELISA, immunoprecipitation, immunoblotting, Western blot, slot blot assay, dot blot assay, isoelectric focusing, SDS-polyacrylamide gel electrophoresis and antibody microarray, immunohistological staining, radioimmunoassay (RIA), fluoroimmunoassay, or avidin-biotin or streptavidin-biotin immunoassay.

12. The method of claim 10, wherein the sample is selected from blood, serum, plasma, synovial fluid or joint tissue obtained from the subject.

13. The method of claim 1, wherein the antibody binding is detected by one or more of immunoassay, immunosorbent assay, enzyme linked immunosorbent assay (ELISA), sandwich ELISA, immunoprecipitation, immunoblotting, Western blot, slot blot assay, dot blot assay, antibody microarray, immunohistological staining, radioimmunoassay (RIA), fluoroimmunoassay, or avidin-biotin or streptavidin-biotin immunoassay.

14. The method of claim 4, wherein the binding is detected by one or more of immunoassay, spectrometry, immunosorbent assay, enzyme linked immunosorbent assay (ELISA), sandwich ELISA, immunoprecipitation, immunoblotting, Western blot, slot blot assay, dot blot assay, isoelectric focusing, SDS-polyacrylamide gel electrophoresis and antibody microarray, immunohistological staining, radioimmunoassay (RIA), fluoroimmunoassay, or avidin-biotin or streptavidin-biotin immunoassay.

15. A method of detecting (i) citrullinated tenascin-C and/or one or more citrullinated fragments of tenascin-C; and/or (ii) autoantibodies that specifically bind citrullinated tenascin-C and/or one or more citrullinated fragments of tenascin-C in a sample from a subject, said method comprising:
  a) obtaining a sample from the subject;
  b) contacting the sample with an antibody or an antigen binding fragment thereof directed against citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO: 70 and/or one or more citrullinated fragments of citrullinated tenascin-C comprising one or more citrullinated amino acid residues selected from cit50, cit51, cit55, cit72,cit120, cit169, cit173, cit209, cit214, cit219m, cit220, or cit222 of SEQ ID NO: 70, wherein said antibody or an antigen binding fragment thereof is immobilized on a support, and detecting specific binding between the antibody or an antigen binding fragment thereof and the citrullinated tenascin-C and/or the one or more citrullinated fragments of citrullinated tenascin-C, wherein said binding is indicative of the presence of citrullinated tenascin-C and/or one or more citrullinated fragments of citrullinated tenascin-C in the subject; and/or
  c) contacting the sample with citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO: 70 and/or the one or more citrullinated fragments of citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO: 70, immobilized on a support, and detecting specific binding between autoantibodies in the sample and the immobilized citrullinated tenascin-C and/or the one or more citrullinated fragments of the citrullinated tenascin-C, wherein said binding is indicative of the presence of autoantibodies that bind the citrullinated tenascin-C and/or one or more citrullinated fragments of the citrullinated tenascin-C in the sample.

16. The method of claim 15, wherein the sample is selected from blood, serum, plasma, synovial fluid or joint tissue obtained from the subject.

17. The method of claim 15, wherein the binding is detected by one or more of immunoassay, spectrometry, immunosorbent assay, enzyme linked immunosorbent assay (ELISA), sandwich ELISA, immunoprecipitation, immunoblotting, Western blot, slot blot assay, dot blot assay, isoelectric focusing, SDS-polyacrylamide gel electrophoresis and antibody microarray, immunohistological staining, radioimmunoassay (RIA), fluoroimmunoassay, or avidin-biotin or streptavidin-biotin immunoassay.

18. The method of claim 15, further comprising measuring the levels of the citrullinated tenascin-C and/or the one or more of the citrullinated fragments of citrullinated tenascin-C in step (b) relative to a control or reference; and/or measuring the levels of the autoantibodies that bind to the citrullinated tenascin-C and/or to the one or more citrullinated fragments of the citrullinated tenascin-C in step (c) relative to a control or reference.

19. A method of diagnosing and treating rheumatoid arthritis (RA) in a subject, the method comprising:
    (a) detecting in a sample obtained from the subject specific binding of citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO: 70, and/or one or more citrullinated fragments of citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO:70 in the subject's sample to an immobilized antibody directed to citrullinated tenascin-C and/or one or more citrullinated fragments of citrullinated tenascin-C; and/or
    (b) detecting specific binding of autoantibodies in the subject's sample to immobilized citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO: 70 and/or to one or more immobilized citrullinated fragments of citrullinated tenascin-C comprising one or more citrullinated amino acid residues selected from cit50, cit51, cit55, cit72, cit120, cit169, cit173, cit209, cit214, cit219m, cit220, or cit222 of SEQ ID NO: 70;
    (c) diagnosing RA in the subject when specific binding of the citrullinated tenascin-C and/or of the one or more citrullinated fragments of citrullinated tenascin-C in the subject's sample to the immobilized antibody is detected relative to control or reference levels; and/or when specific binding of autoantibodies in the subject's sample to the immobilized citrullinated tenascin-C and/or to the one or more immobilized citrullinated fragments of citrullinated tenascin-C is detected relative to control or reference levels; and
    (d) treating RA in the diagnosed subject.

20. The method of claim 19, wherein the treatment comprises administering to the subject one or more of an anti-TNF drug; an anti-IL17 therapy; a T-cell co-stimulation modulator; an interleukin-6 (IL-6) inhibitor; an anti-CD20 antibody; a B cell activating factor; an inhibitor of Janus kinase (JAK); an inhibitor of spleen tyrosine kinase (Syk); an anti-TNC antibody; an antibody to citrullinated domains of citrullinated tenascin-C; or an agent that modulates the biological activity of citrullinated and/or non-citrullinated tenascin-C.

21. The method of claim 20, wherein the T-cell co-stimulation modulator is abatacept, a fusion protein comprising the Fc region of IgG1 fused to the extracellular domain of CTLA-4; the interleukin-6 (IL-6) inhibitor is tocilizumab, a humanized monoclonal antibody which binds to the interleukin-6 receptor; the anti-CD20 antibody is rituximab, a chimeric monoclonal antibody which binds to the B cell surface protein CD20; the B cell activating factor is anti-B cell activating factor (BAFF); the inhibitor of Janus kinase (JAK) is compound 3-[(3R,4R)-4-methyl-3-[methyl (7H-pyrrolo[2,3-d]pyrimidin-4-yl)amino]piperidin-1-yl]-3-oxopropanenitrile; and the inhibitor of spleen tyrosine kinase (Syk) is compound [6-({5-Fluoro-2-[(3,4,5-trimethoxyphenyl)amino]pyrimidin-4-yl}amino)-2,2-dimethyl-3-oxo-2,3-dihydro-4H-pyrido[3,2-b][1,4]oxazin-4-yl] methyl dihydrogen phosphate.

22. The method of claim 19, wherein the subject's sample is selected from blood, peripheral blood, serum, plasma, cerebrospinal fluid (CSF), urine, saliva, stool or synovial fluid.

23. The method of claim 19, wherein the binding is detected by one or more of immunoassay, spectrometry, immunosorbent assay, enzyme linked immunosorbent assay (ELISA), sandwich ELISA, immunoprecipitation, immunoblotting, Western blot, slot blot assay, dot blot assay, isoelectric focusing, SDS-polyacrylamide gel electrophoresis and antibody microarray, immunohistological staining, radioimmunoassay (RIA), fluoroimmunoassay, or avidin-biotin or streptavidin-biotin immunoassay.

24. The method of claim 15, wherein the citrullinated tenascin-C or the one or more citrullinated fragments of citrullinated tenascin-C comprise a peptide selected from SEQ ID NO: 55, SEQ ID NO: 57, SEQ ID NO: 59, SEQ ID NO: 61, SEQ ID NO: 63, or SEQ ID NO: 64.

25. The method of claim 15, wherein the citrullinated tenascin-C or the one or more citrullinated fragments of citrullinated tenascin-C comprise one or more citrullinated amino acid residues selected from cit55, cit209, cit214, cit219, or cit220 of SEQ ID NO: 70.

26. The method of claim 19, wherein the citrullinated tenascin-C or the one or more citrullinated fragments of citrullinated tenascin-C comprise a peptide selected from SEQ ID NO: 55, SEQ ID NO: 57, SEQ ID NO: 59, SEQ ID NO: 61, SEQ ID NO: 63, or SEQ ID NO: 64.

27. The method of claim 19, wherein the citrullinated tenascin-C or the one or more citrullinated fragments of citrullinated tenascin-C comprise one or more citrullinated amino acid residues selected from cit55, cit209, cit214, cit219, or cit220 of SEQ ID NO: 70.

* * * * *

SEQUENCE LISTING

```
<160> NUMBER OF SEQ ID NOS: 70

<210> SEQ ID NO 1
<211> LENGTH: 51
<212> TYPE: DNA
<213> ORGANISM: Artificial Sequence
<220> FEATURE:
<223> OTHER INFORMATION: Primer

<400> SEQUENCE: 1
atacatatgc atcatcatca tcatcatggg gtcctcaaga aagtcatccg g        51

<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
gccggatcct tagcctgctc ctgcagtaca ttg                              33

<210> SEQ ID NO 3
<211> LENGTH: 47
<212> TYPE: DNA
<213> ORGANISM: Artificial Sequence
<220> FEATURE:
<223> OTHER INFORMATION: Primer

<400> SEQUENCE: 3
acagtggtac caccatgggg gccatggggg ccatgactca gctgttg              47

<210> SEQ ID NO 4
<211> LENGTH: 45
<212> TYPE: DNA
```

<213> ORGANISM: Artificial Sequence
<220> FEATURE:
<223> OTHER INFORMATION: Primer

<400> SEQUENCE: 4
cttgtcatcg tcgtccttgt agtcaccttc ggtagcgagg gcaag        45

<210> SEQ ID NO 5
<211> LENGTH: 44
<212> TYPE: DNA
<213> ORGANISM: Artificial Sequence
<220> FEATURE:
<223> OTHER INFORMATION: Primer

<400> SEQUENCE: 5
gactagaagg acgacgatga caagtgctgt ctccagcctg ccac        44

<210> SEQ ID NO 6
<211> LENGTH: 56
<212> TYPE: DNA
<213> ORGANISM: Artificial Sequence
<220> FEATURE:
<223> OTHER INFORMATION: Primer

<400> SEQUENCE: 6
gacagcggat ccttaatgat gatgatgatg atgtgagcag tcttctccgc tgtagc        56

<210> SEQ ID NO 7
<211> LENGTH: 47
<212> TYPE: DNA
<213> ORGANISM: Artificial Sequence
<220> FEATURE:
<223> OTHER INFORMATION: Primer

<400> SEQUENCE: 7
atacatatgc atcatcatca tcatcatgag gtgtctcctc ccaaaga        47

<210> SEQ ID NO 8
<211> LENGTH: 33
<212> TYPE: DNA
<213> ORGANISM: Artificial Sequence
<220> FEATURE:
<223> OTHER INFORMATION: Primer

<400> SEQUENCE: 8
gccggtacct taagtggatg ccttcacacg tgc        33

<210> SEQ ID NO 9
<211> LENGTH: 47
<212> TYPE: DNA
<213> ORGANISM: Artificial Sequence
<220> FEATURE:
<223> OTHER INFORMATION: Primer

<400> SEQUENCE: 9
atacatatgc atcatcatca tcatcatgag gtgtctcctc ccaaaga        47

<210> SEQ ID NO 10
<211> LENGTH: 33
<212> TYPE: DNA
<213> ORGANISM: Artificial Sequence
<220> FEATURE:
<223> OTHER INFORMATION: Primer

<400> SEQUENCE: 10
gccggtacct tatgttgtga aggtctcttt ggc        33

<210> SEQ ID NO 11
<211> LENGTH: 50
<212> TYPE: DNA
<213> ORGANISM: Artificial Sequence
<220> FEATURE:
<223> OTHER INFORMATION: Primer

<400> SEQUENCE: 11
atacatatgc atcatcatca tcatcatcgc ttggatgccc ccagccagat            50

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
gccggtacct taagtggatg ccttcacacg tgc                              33

<210> SEQ ID NO 13
<211> LENGTH: 48
<212> TYPE: DNA
<213> ORGANISM: Artificial Sequence
<220> FEATURE:
<223> OTHER INFORMATION: Primer

<400> SEQUENCE: 13
atacatatgc atcatcatca tcatcatgag ttggacacgc ccaaggac              48

<210> SEQ ID NO 14
<211> LENGTH: 38
<212> TYPE: DNA
<213> ORGANISM: Artificial Sequence
<220> FEATURE:
<223> OTHER INFORMATION: Primer

<400> SEQUENCE: 14
gccggatcct tatgttgtga acttggcagt gatggttg                         38

<210> SEQ ID NO 15
<211> LENGTH: 48
<212> TYPE: DNA
<213> ORGANISM: Artificial Sequence
<220> FEATURE:
<223> OTHER INFORMATION: Primer

<400> SEQUENCE: 15
atacatatgc atcatcatca tcatcatgcc atgggctccc caaaggaa              48

<210> SEQ ID NO 16
<211> LENGTH: 36
<212> TYPE: DNA
<213> ORGANISM: Artificial Sequence
<220> FEATURE:
<223> OTHER INFORMATION: Primer

<400> SEQUENCE: 16
gccggatcct tatgtggtga agatggtctg gatcat                           36

<210> SEQ ID NO 17
<211> LENGTH: 49
<212> TYPE: DNA
<213> ORGANISM: Artificial Sequence
<220> FEATURE:

-continued

<223> OTHER INFORMATION: Primer

<400> SEQUENCE: 17
atacatatgc atcatcatca tcatcatatt ggactcctgt accccttcc        49

<210> SEQ ID NO 18
<211> LENGTH: 35
<212> TYPE: DNA
<213> ORGANISM: Artificial Sequence
<220> FEATURE:
<223> OTHER INFORMATION: Primer

<400> SEQUENCE: 18
gccggatcct tatgcccgtt tgcgcctgcc ttcaa        35

<210> SEQ ID NO 19
<211> LENGTH: 18
<212> TYPE: DNA
<213> ORGANISM: Artificial Sequence
<220> FEATURE:
<223> OTHER INFORMATION: His tag sequence

<400> SEQUENCE: 19
catcatcatc atcatcat        18

<210> SEQ ID NO 20
<211> LENGTH: 30
<212> TYPE: PRT
<213> ORGANISM: Homo sapiens

<400> SEQUENCE: 20

Thr Ile Gly Leu Leu Tyr Pro Phe Pro Lys Asp Cys Ser Gln Ala Met
1               5                   10                  15

Leu Asn Gly Asp Thr Thr Ser Gly Leu Tyr Thr Ile Tyr Leu
            20                  25                  30

<210> SEQ ID NO 21
<211> LENGTH: 30
<212> TYPE: PRT
<213> ORGANISM: Homo sapiens

<400> SEQUENCE: 21

Tyr Thr Ile Tyr Leu Asn Gly Asp Lys Ala Glu Ala Leu Glu Val Phe
1               5                   10                  15

Cys Asp Met Thr Ser Asp Gly Gly Gly Trp Ile Val Phe Leu
            20                  25                  30

<210> SEQ ID NO 22
<211> LENGTH: 30
<212> TYPE: PRT
<213> ORGANISM: Homo sapiens

<400> SEQUENCE: 22

Trp Ile Val Phe Leu Arg Arg Lys Asn Gly Arg Glu Asn Phe Tyr Gln
1               5                   10                  15

Asn Trp Lys Ala Tyr Ala Ala Gly Phe Gly Asp Arg Arg Glu
            20                  25                  30

<210> SEQ ID NO 23
<211> LENGTH: 28
<212> TYPE: PRT
<213> ORGANISM: Homo sapiens

<400> SEQUENCE: 23

Gly Asp Arg Arg Glu Glu Phe Trp Leu Gly Leu Asp Asn Leu Asn Lys
1               5                   10                  15

Ile Thr Ala Gln Gly Gln Tyr Glu Leu Arg Val Asp
            20                  25

<210> SEQ ID NO 24
<211> LENGTH: 30
<212> TYPE: PRT
<213> ORGANISM: Homo sapiens

<400> SEQUENCE: 24

Glu Leu Arg Val Asp Leu Arg Asp His Gly Glu Thr Ala Phe Ala Val
1               5                   10                  15

Tyr Asp Lys Phe Ser Val Gly Asp Ala Lys Thr Arg Tyr Lys
            20                  25                  30

<210> SEQ ID NO 25
<211> LENGTH: 29
<212> TYPE: PRT
<213> ORGANISM: Homo sapiens

<400> SEQUENCE: 25

Lys Thr Arg Tyr Lys Leu Lys Val Glu Gly Tyr Ser Gly Thr Ala Gly
1               5                   10                  15

Asp Ser Met Ala Tyr His Asn Gly Arg Ser Phe Ser Thr
            20                  25

<210> SEQ ID NO 26
<211> LENGTH: 29
<212> TYPE: PRT
<213> ORGANISM: Homo sapiens

<400> SEQUENCE: 26

Arg Ser Phe Ser Thr Phe Asp Lys Asp Thr Asp Ser Ala Ile Thr Asn
1               5                   10                  15

Cys Ala Leu Ser Tyr Lys Gly Ala Phe Trp Tyr Arg Asn
            20                  25

<210> SEQ ID NO 27
<211> LENGTH: 30
<212> TYPE: PRT
<213> ORGANISM: Homo sapiens

<400> SEQUENCE: 27

Trp Tyr Arg Asn Cys His Arg Val Asn Leu Met Gly Arg Tyr Gly Asp
1               5                   10                  15

Asn Asn His Ser Gln Gly Val Asn Trp Phe His Trp Lys Gly
            20                  25                  30

<210> SEQ ID NO 28
<211> LENGTH: 32
<212> TYPE: PRT
<213> ORGANISM: Homo sapiens

<400> SEQUENCE: 28

Phe His Trp Lys Gly His Glu His Ser Ile Gln Phe Ala Glu Met Lys
1               5                   10                  15

Leu Arg Pro Ser Asn Phe Arg Asn Leu Glu Gly Arg Arg Lys Arg Ala
            20                  25                  30

<210> SEQ ID NO 29

```
<211> LENGTH: 21
<212> TYPE: DNA
<213> ORGANISM: Artificial Sequence
<220> FEATURE:
<223> OTHER INFORMATION: siRNA

<400> SEQUENCE: 29
cgcgagaacu ucuaccaaat t                                        21

<210> SEQ ID NO 30
<211> LENGTH: 21
<212> TYPE: DNA
<213> ORGANISM: Artificial Sequence
<220> FEATURE:
<223> OTHER INFORMATION: siRNA

<400> SEQUENCE: 30 uuuggguagaa guucucgcgt c                                       21

<210> SEQ ID NO 31
<211> LENGTH: 21
<212> TYPE: DNA
<213> ORGANISM: Artificial Sequence
<220> FEATURE:
<223> OTHER INFORMATION: siRNA

<400> SEQUENCE: 31
ggaauaugaa uaaagaagat t                                        21

<210> SEQ ID NO 32
<211> LENGTH: 21
<212> TYPE: DNA
<213> ORGANISM: Artificial Sequence
<220> FEATURE:
<223> OTHER INFORMATION: siRNA

<400> SEQUENCE: 32
ucuucuuuau ucauauuccg g                                        21

<210> SEQ ID NO 33
<211> LENGTH: 11
<212> TYPE: PRT
<213> ORGANISM: Homo sapiens

<400> SEQUENCE: 33

Asn Gly Arg Glu Asn Phe Tyr Gln Asn Trp Lys
1               5                   10

<210> SEQ ID NO 34
<211> LENGTH: 10
<212> TYPE: PRT
<213> ORGANISM: Homo sapiens

<400> SEQUENCE: 34

Ala Tyr Ala Ala Gly Phe Gly Asp Arg Arg
1               5                   10

<210> SEQ ID NO 35
<211> LENGTH: 6
<212> TYPE: PRT
<213> ORGANISM: Homo sapiens

<400> SEQUENCE: 35

Thr Arg Tyr Lys Leu Lys
1               5
```

<210> SEQ ID NO 36
<211> LENGTH: 11
<212> TYPE: PRT
<213> ORGANISM: Homo sapiens

<400> SEQUENCE: 36

Gly Ala Phe Trp Tyr Arg Arg Asn Cys His Arg
1               5                   10

<210> SEQ ID NO 37
<211> LENGTH: 10
<212> TYPE: PRT
<213> ORGANISM: Homo sapiens

<400> SEQUENCE: 37

Asn Cys His Arg Val Asn Leu Met Gly Arg
1               5                   10

<210> SEQ ID NO 38
<211> LENGTH: 10
<212> TYPE: PRT
<213> ORGANISM: Homo sapiens

<400> SEQUENCE: 38

Asn Cys His Arg Val Asn Leu Met Gly Arg
1               5                   10

<210> SEQ ID NO 39
<211> LENGTH: 10
<212> TYPE: PRT
<213> ORGANISM: Homo sapiens

<400> SEQUENCE: 39

Asn Cys His Arg Val Asn Leu Met Gly Arg
1               5                   10

<210> SEQ ID NO 40
<211> LENGTH: 10
<212> TYPE: PRT
<213> ORGANISM: Homo sapiens

<400> SEQUENCE: 40

Asn Cys His Arg Val Asn Leu Met Gly Arg
1               5                   10

<210> SEQ ID NO 41
<211> LENGTH: 7
<212> TYPE: PRT
<213> ORGANISM: Homo sapiens

<400> SEQUENCE: 41

Leu Arg Pro Ser Asn Phe Arg
1               5

<210> SEQ ID NO 42
<211> LENGTH: 12
<212> TYPE: PRT
<213> ORGANISM: Homo sapiens

<400> SEQUENCE: 42

Leu Arg Pro Ser Asn Phe Arg Asn Leu Glu Gly Arg
1               5                   10

<210> SEQ ID NO 43

```
<211> LENGTH: 12
<212> TYPE: PRT
<213> ORGANISM: Homo sapiens

<400> SEQUENCE: 43

Leu Arg Pro Ser Asn Phe Arg Asn Leu Glu Gly Arg
1               5                   10

<210> SEQ ID NO 44
<211> LENGTH: 12
<212> TYPE: PRT
<213> ORGANISM: Homo sapiens

<400> SEQUENCE: 44

Leu Arg Pro Ser Asn Phe Arg Asn Leu Glu Gly Arg
1               5                   10

<210> SEQ ID NO 45
<211> LENGTH: 12
<212> TYPE: PRT
<213> ORGANISM: Homo sapiens

<400> SEQUENCE: 45

Leu Arg Pro Ser Asn Phe Arg Asn Leu Glu Gly Arg
1               5                   10

<210> SEQ ID NO 46
<211> LENGTH: 13
<212> TYPE: PRT
<213> ORGANISM: Homo sapiens

<400> SEQUENCE: 46

Leu Arg Pro Ser Asn Phe Arg Asn Leu Glu Gly Arg Arg
1               5                   10

<210> SEQ ID NO 47
<211> LENGTH: 12
<212> TYPE: PRT
<213> ORGANISM: Homo sapiens

<400> SEQUENCE: 47

Leu Arg Pro Ser Asn Phe Arg Asn Leu Glu Gly Arg
1               5                   10

<210> SEQ ID NO 48
<211> LENGTH: 7
<212> TYPE: PRT
<213> ORGANISM: Homo sapiens

<400> SEQUENCE: 48

Asn Leu Glu Gly Arg Arg Lys
1               5

<210> SEQ ID NO 49
<211> LENGTH: 13
<212> TYPE: PRT
<213> ORGANISM: Homo sapiens

<400> SEQUENCE: 49

Leu Arg Pro Ser Asn Phe Arg Asn Leu Glu Gly Arg Arg
1               5                   10

<210> SEQ ID NO 50
<211> LENGTH: 13
<212> TYPE: PRT
```

```
<213> ORGANISM: Homo sapiens

<400> SEQUENCE: 50

Leu Arg Pro Ser Asn Phe Arg Asn Leu Glu Gly Arg Arg
1               5                   10

<210> SEQ ID NO 51
<211> LENGTH: 12
<212> TYPE: PRT
<213> ORGANISM: Homo sapiens

<400> SEQUENCE: 51

Leu Arg Pro Ser Asn Phe Arg Asn Leu Glu Gly Arg
1               5                   10

<210> SEQ ID NO 52
<211> LENGTH: 13
<212> TYPE: PRT
<213> ORGANISM: Homo sapiens

<400> SEQUENCE: 52

Leu Arg Pro Ser Asn Phe Arg Asn Leu Glu Gly Arg Arg
1               5                   10

<210> SEQ ID NO 53
<211> LENGTH: 13
<212> TYPE: PRT
<213> ORGANISM: Homo sapiens

<400> SEQUENCE: 53

Leu Arg Pro Ser Asn Phe Arg Asn Leu Glu Gly Arg Arg
1               5                   10

<210> SEQ ID NO 54
<211> LENGTH: 18
<212> TYPE: PRT
<213> ORGANISM: Artificial Sequence
<220> FEATURE:
<223> OTHER INFORMATION: Cyclic FBG peptide

<400> SEQUENCE: 54

Cys Val Phe Leu Arg Arg Lys Asn Gly Arg Glu Asn Phe Tyr Gln Asn
1               5                   10                  15

Trp Cys

<210> SEQ ID NO 55
<211> LENGTH: 18
<212> TYPE: PRT
<213> ORGANISM: Artificial Sequence
<220> FEATURE:
<223> OTHER INFORMATION: Cyclic FBG peptide
<220> FEATURE:
<221> NAME/KEY: MOD_RES
<222> LOCATION: (10)..(10)
<223> OTHER INFORMATION: X = citrulline

<400> SEQUENCE: 55

Cys Val Phe Leu Arg Arg Lys Asn Gly Xaa Glu Asn Phe Tyr Gln Asn
1               5                   10                  15

Trp Cys

<210> SEQ ID NO 56
<211> LENGTH: 19
<212> TYPE: PRT
<213> ORGANISM: Artificial Sequence
```

```
<220> FEATURE:
<223> OTHER INFORMATION: Cyclic FBG peptide

<400> SEQUENCE: 56

Cys Ala Tyr Ala Ala Gly Phe Gly Asp Arg Arg Glu Glu Phe Trp Leu
1               5                   10                  15

Gly Leu Cys

<210> SEQ ID NO 57
<211> LENGTH: 19
<212> TYPE: PRT
<213> ORGANISM: Artificial Sequence
<220> FEATURE:
<223> OTHER INFORMATION: Cyclic FBG peptide
<220> FEATURE:
<221> NAME/KEY: MOD_RES
<222> LOCATION: (10)..(10)
<223> OTHER INFORMATION: X = citrulline

<400> SEQUENCE: 57

Cys Ala Tyr Ala Ala Gly Phe Gly Asp Xaa Arg Glu Glu Phe Trp Leu
1               5                   10                  15

Gly Leu Cys

<210> SEQ ID NO 58
<211> LENGTH: 19
<212> TYPE: PRT
<213> ORGANISM: Artificial Sequence
<220> FEATURE:
<223> OTHER INFORMATION: Cyclic FBG peptide

<400> SEQUENCE: 58

Cys Phe Ser Val Gly Asp Ala Lys Thr Arg Tyr Lys Leu Lys Val Glu
1               5                   10                  15

Gly Tyr Cys

<210> SEQ ID NO 59
<211> LENGTH: 19
<212> TYPE: PRT
<213> ORGANISM: Artificial Sequence
<220> FEATURE:
<223> OTHER INFORMATION: cyclic FBG peptide
<220> FEATURE:
<221> NAME/KEY: MOD_RES
<222> LOCATION: (10)..(10)
<223> OTHER INFORMATION: X = citrulline

<400> SEQUENCE: 59

Cys Phe Ser Val Gly Asp Ala Lys Thr Xaa Tyr Lys Leu Lys Val Glu
1               5                   10                  15

Gly Tyr Cys

<210> SEQ ID NO 60
<211> LENGTH: 19
<212> TYPE: PRT
<213> ORGANISM: Artificial Sequence
<220> FEATURE:
<223> OTHER INFORMATION: Cyclic FBG peptide

<400> SEQUENCE: 60

Cys Lys Gly Ala Phe Trp Tyr Arg Asn Cys His Arg Val Asn Leu Met
1               5                   10                  15

Gly Arg Cys
```

```
<210> SEQ ID NO 61
<211> LENGTH: 19
<212> TYPE: PRT
<213> ORGANISM: Artificial Sequence
<220> FEATURE:
<223> OTHER INFORMATION: Cyclic FBG peptide
<220> FEATURE:
<221> NAME/KEY: MOD_RES
<222> LOCATION: (8)..(8)
<223> OTHER INFORMATION: X = citrulline
<220> FEATURE:
<221> NAME/KEY: MOD_RES
<222> LOCATION: (12)..(12)
<223> OTHER INFORMATION: X = citrulline

<400> SEQUENCE: 61

Cys Lys Gly Ala Phe Trp Tyr Xaa Asn Cys His Xaa Val Asn Leu Met
1               5                   10                  15

Gly Arg Cys

<210> SEQ ID NO 62
<211> LENGTH: 20
<212> TYPE: PRT
<213> ORGANISM: Artificial Sequence
<220> FEATURE:
<223> OTHER INFORMATION: Cyclic FBG peptide

<400> SEQUENCE: 62

Cys Glu Met Lys Leu Arg Pro Ser Asn Phe Arg Asn Leu Glu Gly Arg
1               5                   10                  15

Arg Lys Arg Cys
            20

<210> SEQ ID NO 63
<211> LENGTH: 20
<212> TYPE: PRT
<213> ORGANISM: Artificial Sequence
<220> FEATURE:
<223> OTHER INFORMATION: Cyclic FBG peptide
<220> FEATURE:
<221> NAME/KEY: MOD_RES
<222> LOCATION: (6)..(6)
<223> OTHER INFORMATION: X = citrulline
<220> FEATURE:
<221> NAME/KEY: MOD_RES
<222> LOCATION: (11)..(11)
<223> OTHER INFORMATION: X = citrulline

<400> SEQUENCE: 63

Cys Glu Met Lys Leu Xaa Pro Ser Asn Phe Xaa Asn Leu Glu Gly Arg
1               5                   10                  15

Arg Lys Arg Cys
            20

<210> SEQ ID NO 64
<211> LENGTH: 20
<212> TYPE: PRT
<213> ORGANISM: Artificial Sequence
<220> FEATURE:
<223> OTHER INFORMATION: Cyclic FBG peptide
<220> FEATURE:
<221> NAME/KEY: MOD_RES
<222> LOCATION: (16)..(16)
<223> OTHER INFORMATION: X = citrulline
<220> FEATURE:
<221> NAME/KEY: MOD_RES
<222> LOCATION: (17)..(17)
<223> OTHER INFORMATION: X = citrulline

<400> SEQUENCE: 64
```

Cys Glu Met Lys Leu Arg Pro Ser Asn Phe Arg Asn Leu Glu Gly Xaa
1               5                   10                  15

Xaa Lys Arg Cys
            20

<210> SEQ ID NO 65
<211> LENGTH: 23
<212> TYPE: PRT
<213> ORGANISM: Homo sapiens

<400> SEQUENCE: 65

Gly Val Leu Lys Lys Val Ile Arg His Lys Arg Gln Ser Gly Val Asn
1               5                   10                  15

Ala Thr Leu Pro Glu Glu Asn
            20

<210> SEQ ID NO 66
<211> LENGTH: 476
<212> TYPE: PRT
<213> ORGANISM: Homo sapiens

<400> SEQUENCE: 66

Cys Cys Leu Gln Pro Ala Thr Gly Arg Leu Asp Thr Arg Pro Phe Cys
1               5                   10                  15

Ser Gly Arg Gly Asn Phe Ser Thr Glu Gly Cys Gly Cys Val Cys Glu
            20                  25                  30

Pro Gly Trp Lys Gly Pro Asn Cys Ser Glu Pro Glu Cys Pro Gly Asn
        35                  40                  45

Cys His Leu Arg Gly Arg Cys Ile Asp Gly Gln Cys Ile Cys Asp Asp
    50                  55                  60

Gly Phe Thr Gly Glu Asp Cys Ser Gln Leu Ala Cys Pro Ser Asp Cys
65                  70                  75                  80

Asn Asp Gln Gly Lys Cys Val Asn Gly Val Cys Ile Cys Phe Glu Gly
                85                  90                  95

Tyr Ala Gly Ala Asp Cys Ser Arg Glu Ile Cys Pro Val Pro Cys Ser
            100                 105                 110

Glu Glu His Gly Thr Cys Val Asp Gly Leu Cys Val Cys His Asp Gly
        115                 120                 125

Phe Ala Gly Asp Asp Cys Asn Lys Pro Leu Cys Leu Asn Asn Cys Tyr
    130                 135                 140

Asn Arg Gly Arg Cys Val Glu Asn Glu Cys Val Cys Asp Glu Gly Phe
145                 150                 155                 160

Thr Gly Glu Asp Cys Ser Glu Leu Ile Cys Pro Asn Asp Cys Phe Asp
                165                 170                 175

Arg Gly Arg Cys Ile Asn Gly Thr Cys Tyr Cys Glu Glu Gly Phe Thr
            180                 185                 190

Gly Glu Asp Cys Gly Lys Pro Thr Cys Pro His Ala Cys His Thr Gln
        195                 200                 205

Gly Arg Cys Glu Glu Gly Gln Cys Val Cys Asp Glu Gly Phe Ala Gly
    210                 215                 220

Leu Asp Cys Ser Glu Lys Arg Cys Pro Ala Asp Cys His Asn Arg Gly
225                 230                 235                 240

Arg Cys Val Asp Gly Arg Cys Glu Cys Asp Asp Gly Phe Thr Gly Ala
                245                 250                 255

Asp Cys Gly Glu Leu Lys Cys Pro Asn Gly Cys Ser Gly His Gly Arg
            260                 265                 270

```
Cys Val Asn Gly Gln Cys Val Cys Asp Glu Gly Tyr Thr Gly Glu Asp
            275                 280                 285

Cys Ser Gln Leu Arg Cys Pro Asn Asp Cys His Ser Arg Gly Arg Cys
        290                 295                 300

Val Glu Gly Lys Cys Val Cys Glu Gln Gly Phe Lys Gly Tyr Asp Cys
305                 310                 315                 320

Ser Asp Met Ser Cys Pro Asn Asp Cys His Gln His Gly Arg Cys Val
                325                 330                 335

Asn Gly Met Cys Val Cys Asp Asp Gly Tyr Thr Gly Glu Asp Cys Arg
            340                 345                 350

Asp Arg Gln Cys Pro Arg Asp Cys Ser Asn Arg Gly Leu Cys Val Asp
        355                 360                 365

Gly Gln Cys Val Cys Glu Asp Gly Phe Thr Gly Pro Asp Cys Ala Glu
370                 375                 380

Leu Ser Cys Pro Asn Asp Cys His Gly Gln Gly Arg Cys Val Asn Gly
385                 390                 395                 400

Gln Cys Val Cys His Glu Gly Phe Met Gly Lys Asp Cys Lys Glu Gln
            405                 410                 415

Arg Cys Pro Ser Asp Cys His Gly Gln Gly Arg Cys Val Asp Gly Gln
        420                 425                 430

Cys Ile Cys His Glu Gly Phe Thr Gly Leu Asp Cys Gly Gln His Ser
            435                 440                 445

Cys Pro Ser Asp Cys Asn Asn Leu Gly Gln Cys Val Ser Gly Arg Cys
        450                 455                 460

Ile Cys Asn Glu Gly Tyr Ser Gly Glu Asp Cys Ser
465                 470                 475

<210> SEQ ID NO 67
<211> LENGTH: 1352
<212> TYPE: PRT
<213> ORGANISM: Homo sapiens

<400> SEQUENCE: 67

Glu Val Ser Pro Pro Lys Asp Leu Val Val Thr Glu Val Thr Glu Glu
1               5                   10                  15

Thr Val Asn Leu Ala Trp Asp Asn Glu Met Arg Val Thr Glu Tyr Leu
            20                  25                  30

Val Val Tyr Thr Pro Thr His Glu Gly Gly Leu Glu Met Gln Phe Arg
        35                  40                  45

Val Pro Gly Asp Gln Thr Ser Thr Ile Ile Gln Glu Leu Glu Pro Gly
    50                  55                  60

Val Glu Tyr Phe Ile Arg Val Phe Ala Ile Leu Glu Asn Lys Lys Ser
65                  70                  75                  80

Ile Pro Val Ser Ala Arg Val Ala Thr Tyr Leu Pro Ala Pro Glu Gly
                85                  90                  95

Leu Lys Phe Lys Ser Ile Lys Glu Thr Ser Val Glu Val Glu Trp Asp
            100                 105                 110

Pro Leu Asp Ile Ala Phe Glu Thr Trp Glu Ile Ile Phe Arg Asn Met
        115                 120                 125

Asn Lys Glu Asp Glu Gly Glu Ile Thr Lys Ser Leu Arg Arg Pro Glu
    130                 135                 140

Thr Ser Tyr Arg Gln Thr Gly Leu Ala Pro Gly Gln Glu Tyr Glu Ile
145                 150                 155                 160

Ser Leu His Ile Val Lys Asn Asn Thr Arg Gly Pro Gly Leu Lys Arg
```

```
                165                 170                 175
Val Thr Thr Thr Arg Leu Asp Ala Pro Ser Gln Ile Glu Val Lys Asp
            180                 185                 190

Val Thr Asp Thr Thr Ala Leu Ile Thr Trp Phe Lys Pro Leu Ala Glu
            195                 200                 205

Ile Asp Gly Ile Glu Leu Thr Tyr Gly Ile Lys Asp Val Pro Gly Asp
            210                 215                 220

Arg Thr Thr Ile Asp Leu Thr Glu Asp Glu Asn Gln Tyr Ser Ile Gly
225                 230                 235                 240

Asn Leu Lys Pro Asp Thr Glu Tyr Glu Val Ser Leu Ile Ser Arg Arg
                245                 250                 255

Gly Asp Met Ser Ser Asn Pro Ala Lys Glu Thr Phe Thr Thr Gly Leu
                260                 265                 270

Asp Ala Pro Arg Asn Leu Arg Arg Val Ser Gln Thr Asp Asn Ser Ile
                275                 280                 285

Thr Leu Glu Trp Arg Asn Gly Lys Ala Ala Ile Asp Ser Tyr Arg Ile
            290                 295                 300

Lys Tyr Ala Pro Ile Ser Gly Gly Asp His Ala Glu Val Asp Val Pro
305                 310                 315                 320

Lys Ser Gln Gln Ala Thr Thr Lys Thr Thr Leu Thr Gly Leu Arg Pro
                325                 330                 335

Gly Thr Glu Tyr Gly Ile Gly Val Ser Ala Val Lys Glu Asp Lys Glu
                340                 345                 350

Ser Asn Pro Ala Thr Ile Asn Ala Ala Thr Glu Leu Asp Thr Pro Lys
                355                 360                 365

Asp Leu Gln Val Ser Glu Thr Ala Glu Thr Ser Leu Thr Leu Leu Trp
            370                 375                 380

Lys Thr Pro Leu Ala Lys Phe Asp Arg Tyr Arg Leu Asn Tyr Ser Leu
385                 390                 395                 400

Pro Thr Gly Gln Trp Val Gly Val Gln Leu Pro Arg Asn Thr Thr Ser
                405                 410                 415

Tyr Val Leu Arg Gly Leu Glu Pro Gly Gln Glu Tyr Asn Val Leu Leu
                420                 425                 430

Thr Ala Glu Lys Gly Arg His Lys Ser Lys Pro Ala Arg Val Lys Ala
            435                 440                 445

Ser Thr Glu Gln Ala Pro Glu Leu Glu Asn Leu Thr Val Thr Glu Val
450                 455                 460

Gly Trp Asp Gly Leu Arg Leu Asn Trp Thr Ala Ala Asp Gln Ala Tyr
465                 470                 475                 480

Glu His Phe Ile Ile Gln Val Gln Glu Ala Asn Lys Val Glu Ala Ala
                485                 490                 495

Arg Asn Leu Thr Val Pro Gly Ser Leu Arg Ala Val Asp Ile Pro Gly
                500                 505                 510

Leu Lys Ala Ala Thr Pro Tyr Thr Val Ser Ile Tyr Gly Val Ile Gln
                515                 520                 525

Gly Tyr Arg Thr Pro Val Leu Ser Ala Glu Ala Ser Thr Gly Glu Thr
                530                 535                 540

Pro Asn Leu Gly Glu Val Val Ala Glu Val Gly Trp Asp Ala Leu
545                 550                 555                 560

Lys Leu Asn Trp Thr Ala Pro Glu Gly Ala Tyr Glu Tyr Phe Phe Ile
                565                 570                 575

Gln Val Gln Glu Ala Asp Thr Val Glu Ala Ala Gln Asn Leu Thr Val
            580                 585                 590
```

```
Pro Gly Gly Leu Arg Ser Thr Asp Leu Pro Gly Leu Lys Ala Ala Thr
        595                 600                 605

His Tyr Thr Ile Thr Ile Arg Gly Val Thr Gln Asp Phe Ser Thr Thr
        610                 615                 620

Pro Leu Ser Val Glu Val Leu Thr Glu Val Pro Asp Met Gly Asn
625                 630                 635                 640

Leu Thr Val Thr Glu Val Ser Trp Asp Ala Leu Arg Leu Asn Trp Thr
                645                 650                 655

Thr Pro Asp Gly Thr Tyr Asp Gln Phe Thr Ile Gln Val Gln Glu Ala
                660                 665                 670

Asp Gln Val Glu Glu Ala His Asn Leu Thr Val Pro Gly Ser Leu Arg
                675                 680                 685

Ser Met Glu Ile Pro Gly Leu Arg Ala Gly Thr Pro Tyr Thr Val Thr
        690                 695                 700

Leu His Gly Glu Val Arg Gly His Ser Thr Arg Pro Leu Ala Val Glu
705                 710                 715                 720

Val Val Thr Glu Asp Leu Pro Gln Leu Gly Asp Leu Ala Val Ser Glu
                725                 730                 735

Val Gly Trp Asp Gly Leu Arg Leu Asn Trp Thr Ala Ala Asp Asn Ala
                740                 745                 750

Tyr Glu His Phe Val Ile Gln Val Gln Glu Val Asn Lys Val Glu Ala
        755                 760                 765

Ala Gln Asn Leu Thr Leu Pro Gly Ser Leu Arg Ala Val Asp Ile Pro
770                 775                 780

Gly Leu Glu Ala Ala Thr Pro Tyr Arg Val Ser Ile Tyr Gly Val Ile
785                 790                 795                 800

Arg Gly Tyr Arg Thr Pro Val Leu Ser Ala Glu Ala Ser Thr Ala Lys
                805                 810                 815

Glu Pro Glu Ile Gly Asn Leu Asn Val Ser Asp Ile Thr Pro Glu Ser
                820                 825                 830

Phe Asn Leu Ser Trp Met Ala Thr Asp Gly Ile Phe Glu Thr Phe Thr
        835                 840                 845

Ile Glu Ile Ile Asp Ser Asn Arg Leu Leu Glu Thr Val Glu Tyr Asn
850                 855                 860

Ile Ser Gly Ala Glu Arg Thr Ala His Ile Ser Gly Leu Pro Pro Ser
865                 870                 875                 880

Thr Asp Phe Ile Val Tyr Leu Ser Gly Leu Ala Pro Ser Ile Arg Thr
                885                 890                 895

Lys Thr Ile Ser Ala Thr Ala Thr Thr Glu Ala Leu Pro Leu Leu Glu
                900                 905                 910

Asn Leu Thr Ile Ser Asp Ile Asn Pro Tyr Gly Phe Thr Val Ser Trp
        915                 920                 925

Met Ala Ser Glu Asn Ala Phe Asp Ser Phe Leu Val Thr Val Val Asp
        930                 935                 940

Ser Gly Lys Leu Leu Asp Pro Gln Glu Phe Thr Leu Ser Gly Thr Gln
945                 950                 955                 960

Arg Lys Leu Glu Leu Arg Gly Leu Ile Thr Gly Ile Gly Tyr Glu Val
                965                 970                 975

Met Val Ser Gly Phe Thr Gln Gly His Gln Thr Lys Pro Leu Arg Ala
                980                 985                 990

Glu Ile Val Thr Glu Ala Glu Pro  Glu Val Asp Asn Leu  Leu Val Ser
        995                 1000                 1005
```

| | | | | | | | | | | | |
|---|---|---|---|---|---|---|---|---|---|---|---|
|Asp|Ala|Thr|Pro|Asp|Gly|Phe|Arg|Leu|Ser|Trp|Thr|Ala|Asp|Glu|
| |1010| | | |1015| | | |1020| | | | | |

Asp Ala Thr Pro Asp Gly Phe Arg Leu Ser Trp Thr Ala Asp Glu
    1010                    1015                  1020

Gly Val Phe Asp Asn Phe Val Leu Lys Ile Arg Asp Thr Lys Lys
    1025                    1030                  1035

Gln Ser Glu Pro Leu Glu Ile Thr Leu Leu Ala Pro Glu Arg Thr
    1040                    1045                  1050

Arg Asp Leu Thr Gly Leu Arg Glu Ala Thr Glu Tyr Glu Ile Glu
    1055                    1060                  1065

Leu Tyr Gly Ile Ser Lys Gly Arg Arg Ser Gln Thr Val Ser Ala
    1070                    1075                  1080

Ile Ala Thr Thr Ala Met Gly Ser Pro Lys Glu Val Ile Phe Ser
    1085                    1090                  1095

Asp Ile Thr Glu Asn Ser Ala Thr Val Ser Trp Arg Ala Pro Thr
    1100                    1105                  1110

Ala Gln Val Glu Ser Phe Arg Ile Thr Tyr Val Pro Ile Thr Gly
    1115                    1120                  1125

Gly Thr Pro Ser Met Val Thr Val Asp Gly Thr Lys Thr Gln Thr
    1130                    1135                  1140

Arg Leu Val Lys Leu Ile Pro Gly Val Glu Tyr Leu Val Ser Ile
    1145                    1150                  1155

Ile Ala Met Lys Gly Phe Glu Glu Ser Glu Pro Val Ser Gly Ser
    1160                    1165                  1170

Phe Thr Thr Ala Leu Asp Gly Pro Ser Gly Leu Val Thr Ala Asn
    1175                    1180                  1185

Ile Thr Asp Ser Glu Ala Leu Ala Arg Trp Gln Pro Ala Ile Ala
    1190                    1195                  1200

Thr Val Asp Ser Tyr Val Ile Ser Tyr Thr Gly Glu Lys Val Pro
    1205                    1210                  1215

Glu Ile Thr Arg Thr Val Ser Gly Asn Thr Val Glu Tyr Ala Leu
    1220                    1225                  1230

Thr Asp Leu Glu Pro Ala Thr Glu Tyr Thr Leu Arg Ile Phe Ala
    1235                    1240                  1245

Glu Lys Gly Pro Gln Lys Ser Ser Thr Ile Thr Ala Lys Phe Thr
    1250                    1255                  1260

Thr Asp Leu Asp Ser Pro Arg Asp Leu Thr Ala Thr Glu Val Gln
    1265                    1270                  1275

Ser Glu Thr Ala Leu Leu Thr Trp Arg Pro Pro Arg Ala Ser Val
    1280                    1285                  1290

Thr Gly Tyr Leu Leu Val Tyr Glu Ser Val Asp Gly Thr Val Lys
    1295                    1300                  1305

Glu Val Ile Val Gly Pro Asp Thr Thr Ser Tyr Ser Leu Ala Asp
    1310                    1315                  1320

Leu Ser Pro Ser Thr His Tyr Thr Ala Lys Ile Gln Ala Leu Asn
    1325                    1330                  1335

Gly Pro Leu Arg Ser Asn Met Ile Gln Thr Ile Phe Thr Thr
    1340                    1345                  1350

<210> SEQ ID NO 68
<211> LENGTH: 228
<212> TYPE: PRT
<213> ORGANISM: Homo sapiens

<400> SEQUENCE: 68

Ile Gly Leu Leu Tyr Pro Phe Pro Lys Asp Cys Ser Gln Ala Met Leu
1               5                   10                 15

Asn Gly Asp Thr Thr Ser Gly Leu Tyr Thr Ile Tyr Leu Asn Gly Asp
            20                  25                  30

Lys Ala Gln Ala Leu Glu Val Phe Cys Asp Met Thr Ser Asp Gly Gly
        35                  40                  45

Gly Trp Ile Val Phe Leu Arg Arg Lys Asn Gly Arg Glu Asn Phe Tyr
    50                  55                  60

Gln Asn Trp Lys Ala Tyr Ala Ala Gly Phe Gly Asp Arg Arg Glu Glu
65                  70                  75                  80

Phe Trp Leu Gly Leu Asp Asn Leu Asn Lys Ile Thr Ala Gln Gly Gln
                85                  90                  95

Tyr Glu Leu Arg Val Asp Leu Arg Asp His Gly Glu Thr Ala Phe Ala
            100                 105                 110

Val Tyr Asp Lys Phe Ser Val Gly Asp Ala Lys Thr Arg Tyr Lys Leu
        115                 120                 125

Lys Val Glu Gly Tyr Ser Gly Thr Ala Gly Asp Ser Met Ala Tyr His
    130                 135                 140

Asn Gly Arg Ser Phe Ser Thr Phe Asp Lys Asp Thr Asp Ser Ala Ile
145                 150                 155                 160

Thr Asn Cys Ala Leu Ser Tyr Lys Gly Ala Phe Trp Tyr Arg Asn Cys
                165                 170                 175

His Arg Val Asn Leu Met Gly Arg Tyr Gly Asp Asn Asn His Ser Gln
            180                 185                 190

Gly Val Asn Trp Phe His Trp Lys Gly His Glu His Ser Ile Gln Phe
        195                 200                 205

Ala Glu Met Lys Leu Arg Pro Ser Asn Phe Arg Asn Leu Glu Gly Arg
    210                 215                 220

Arg Lys Arg Ala
225

<210> SEQ ID NO 69
<211> LENGTH: 7616
<212> TYPE: DNA
<213> ORGANISM: Homo sapiens

<400> SEQUENCE: 69
attacagagg aaggagctcg ctatataagc cagccaaagt tggctgcacc ggccacagcc        60
tgcctactgt cacccgcctc tcccgcgcgc agatacacgc cccgcctcc gtgggcacaa       120
aggcagcgct gctggggaac tcgggggaac gcgcacgtgg gaaccgccgc agctccacac       180
tccaggtact tcttccaagg acctaggtct ctcgcccatc ggaaagaaaa taattctttc       240
aagaagatca gggacaactg atttgaagtc tactctgtgc ttctaaatcc ccaattctgc       300
tgaaagtgag atacctaga gccctagagc cccagcagca cccagccaaa cccacctcca       360
ccatggggc catgactcag ctgttggcag gtgtctttct tgctttcctt gccctcgcta       420
ccgaaggtgg ggtcctcaag aaagtcatcc ggcacaagcg acagagtggg gtgaacgcca       480
ccctgccaga agagaaccag ccagtggtgt taaccacgt ttacaacatc aagctgccag       540
tgggatccca gtgttcggtg gatctggagt cagccagtgg ggagaaagac ctggcaccgc       600
cttcagagcc cagcgaaagc tttcaggagc acacagtgga tggggaaaac cagattgtct       660
tcacacatcg catcaacatc ccccgccggg cctgtggctg tgccgcagcc cctgatgtta       720
aggagctgct gagcagactg gaggagctgg agaacctggt cttccctg agggagcaat       780
gtactgcagg agcaggctgc tgtctccagc ctgccacagg ccgcttggac accaggccct       840

-continued

| | |
|---|---|
| tctgtagcgg tcggggcaac ttcagcactg aaggatgtgg ctgtgtctgc gaacctggct | 900 |
| ggaaaggccc caactgctct gagcccgaat gtccaggcaa ctgtcacctt cgaggccggt | 960 |
| gcattgatgg gcagtgcatc tgtgacgacg gcttcacggg cgaggactgc agccagctgg | 1020 |
| cttgccccag cgactgcaat gaccagggca agtgcgtaaa tggagtctgc atctgtttcg | 1080 |
| aaggctacgc cggggctgac tgcagccgtg aaatctgccc agtgccctgc agtgaggagc | 1140 |
| acggcacatg tgtagatggc ttgtgtgtgt gccacgatgg ctttgcaggc gatgactgca | 1200 |
| acaagcctct gtgtctcaac aattgctaca accgtggacg atgcgtggag aatgagtgcg | 1260 |
| tgtgtgatga gggtttcacg ggcgaagact gcagtgagct catctgcccc aatgactgct | 1320 |
| tcgaccgggg ccgctgcatc aatggcacct gctactgcga agaaggcttc acaggtgaag | 1380 |
| actgcgggaa acccacctgc ccacatgcct gccacaccca gggccggtgt gaggaggggc | 1440 |
| agtgtgtatg tgatgagggc tttgccggtg tggactgcag cgagaagagg tgtcctgctg | 1500 |
| actgtcacaa tcgtggccgc tgtgtagacg ggcggtgtga gtgtgatgat ggtttcactg | 1560 |
| gagctgactg tggggagctc aagtgtccca atggctgcag tggccatggc cgctgtgtca | 1620 |
| atgggcagtg tgtgtgtgat gagggctata ctggggagga ctgcagccag ctacggtgcc | 1680 |
| ccaatgactg tcacagtcgg ggccgctgtg tcgagggcaa atgtgtatgt gagcaaggct | 1740 |
| tcaagggcta tgactgcagt gacatgagct gccctaatga ctgtcaccag cacggccgct | 1800 |
| gtgtgaatgg catgtgtgtt tgtgatgacg gctacacagg gaagactgc cgggatcgcc | 1860 |
| aatgccccag ggactgcagc aacaggggcc tctgtgtgga cggacagtgc gtctgtgagg | 1920 |
| acggcttcac cggccctgac tgtgcagaac tctcctgtcc aaatgactgc catggccagg | 1980 |
| gtcgctgtgt gaatgggcag tgcgtgtgcc atgaaggatt tatgggcaaa gactgcaagg | 2040 |
| agcaaagatg tcccagtgac tgtcatggcc agggccgctg cgtggacggc cagtgcatct | 2100 |
| gccacgaggg cttcacaggc ctggactgtg ccagcactc ctgccccagt gactgcaaca | 2160 |
| acttaggaca atgcgtctcg ggccgctgca tctgcaacga gggctacagc ggagaagact | 2220 |
| gctcagaggt gtctcctccc aaagacctcg ttgtgacaga agtgacggaa gagacggtca | 2280 |
| acctggcctg ggacaatgag atgcgggtca cagagtacct tgtcgtgtac acgcccaccc | 2340 |
| acgagggtgg tctggaaatg cagttccgtg tgcctgggga ccagacgtcc accatcatcc | 2400 |
| aggagctgga gcctggtgtg gagtacttta tccgtgtatt tgccatcctg gagaacaaga | 2460 |
| agagcattcc tgtcagcgcc agggtggcca cgtacttacc tgcacctgaa ggcctgaaat | 2520 |
| tcaagtccat caaggagaca tctgtggaag tggagtggga tcctctagac attgcttttg | 2580 |
| aaacctggga gatcatcttc cggaatatga ataaagaaga tgagggagag atcaccaaaa | 2640 |
| gcctgaggag gccagagacc tcttaccggc aaactggtct agctcctggg caagagtatg | 2700 |
| agatatctct gcacatagtg aaaaacaata cccgggccc tggcctgaag agggtgacca | 2760 |
| ccacacgctt ggatgccccc agccagatcg aggtgaaaga tgtcacagac accactgcct | 2820 |
| tgatcacctg gttcaagccc ctggctgaga tcgatggcat tgagctgacc tacggcatca | 2880 |
| aagacgtgcc aggagaccgt accaccatcg atctcacaga ggacgagaac cagtactcca | 2940 |
| tcgggaacct gaagcctgac actgagtacg aggtgtccct catctcccgc agaggtgaca | 3000 |
| tgtcaagcaa cccagccaaa gagaccttca caacaggcct cgatgctccc aggaatcttc | 3060 |
| gacgtgtttc ccagacagat aacagcatca ccctggaatg gaggaatggc aaggcagcta | 3120 |
| ttgacagtta cagaattaag tatgccccca tctctgagg ggaccacgct gaggttgatg | 3180 |
| ttccaaagag ccaacaagcc acaaccaaaa ccacactcac aggtctgagg ccgggaactg | 3240 |

```
aatatgggat tggagtttct gctgtgaagg aagacaagga gagcaatcca gcgaccatca    3300
acgcagccac agagttggac acgcccaagg accttcaggt ttctgaaact gcagagacca    3360
gcctgaccct gctctggaag acaccgttgg ccaaatttga ccgctaccgc ctcaattaca    3420
gtctccccac aggccagtgg gtgggagtgc agcttccaag aaacaccact tcctatgtcc    3480
tgagaggcct ggaaccagga caggagtaca atgtcctcct gacagccgag aaaggcagac    3540
acaagagcaa gcccgcacgt gtgaaggcat ccactgaaca agcccctgag ctggaaaacc    3600
tcaccgtgac tgaggttggc tgggatggcc tcagactcaa ctggaccgca gctgaccagg    3660
cctatgagca ctttatcatt caggtgcagg aggccaacaa ggtggaggca gctcggaacc    3720
tcaccgtgcc tggcagcctt cgggctgtgg acataccggg cctcaaggct gctacgcctt    3780
atacagtctc catctatggg gtgatccagg gctatagaac accagtgctc tctgctgagg    3840
cctccacagg ggaaactccc aatttgggag aggtcgtggt ggccgaggtg ggctgggatg    3900
ccctcaaact caactggact gctccagaag gggcctatga gtacttttc attcaggtgc    3960 aggaggctga cacagtagag gcagcccaga acctcaccgt cccaggagga ctgaggtcca    4020
cagacctgcc tgggctcaaa gcagccactc attataccat caccatccgc ggggtcactc    4080
aggacttcag cacaacccct ctctctgttg aagtcttgac agaggaggtt ccagatatgg    4140
gaaacctcac agtgaccgag gttagctggg atgctctcag actgaactgg accacgccag    4200
atggaaccta tgaccagttt actattcagg tccaggaggc tgaccaggtg aagaggctc    4260 acaatctcac ggttcctggc agcctgcgtt ccatggaaat cccaggcctc agggctggca    4320
ctccttacac agtcaccctg cacggcgagg tcaggggcca cagcactcga ccccttgctg    4380
tagaggtcgt cacagaggat ctcccacagc tgggagattt agccgtgtct gaggttggct    4440
gggatggcct cagactcaac tggaccgcag ctgacaatgc ctatgagcac tttgtcattc    4500
aggtgcagga ggtcaacaaa gtggaggcag cccagaacct cacgttgcct ggcagcctca    4560
gggctgtgga catcccgggc ctcgaggctg ccacgcctta tagtctccc atctatgggg    4620 tgatccgggg ctatagaaca ccagtactct ctgctgaggc ctccacagcc aaagaacctg    4680
aaattggaaa cttaaatgtt tctgacataa ctcccgagag cttcaatctc tcctggatgg    4740
ctaccgatgg gatcttcgag acctttacca ttgaaattat tgattccaat aggttgctgg    4800
agactgtgga atataatatc tctggtgctg aacgaactgc ccatatctca gggctacccc    4860
ctagtactga ttttattgtc tacctctctg gacttgctcc cagcatccgg accaaaacca    4920
tcagtgccac agccacgaca gaggccctgc cccttctgaa aaacctaacc atttccgaca    4980
ttaatcccta cgggttcaca gtttcctgga tggcatcgga gaatgccttt gacagctttc    5040
tagtaacggt ggtggattct gggaagctgc tggaccccca ggaattcaca ctttcaggaa    5100
cccagaggaa gctggagctt agaggcctca taactggcat tggctatgag gttatggtct    5160
ctggcttcac ccaagggcat caaaccaagc ccttgagggc tgagattgtt acagaagccg    5220
aaccggaagt tgacaacctt ctggtttcag atgccacccc agacggtttc cgtctgtcct    5280
ggacagctga tgaaggggtc ttcgacaatt ttgttctcaa aatcagagat accaaaaagc    5340
agtctgagcc actggaaata accctacttg ccccgaacg taccagggac ataacaggtc    5400
tcagagaggc tactgaatac gaaattgaac tctatggaat aagcaaagga aggcgatccc    5460
agacagtcag tgctatagca acaacagcca tgggctcccc aaaggaagtc atttctcag    5520 acatcactga aaattcggct actgtcagct ggaggcacc cacagcccaa gtggagagct    5580
```

-continued

```
tccggattac ctatgtgccc attacaggag gtacaccctc catggtaact gtggacggaa    5640
ccaagactca gaccaggctg gtgaaactca tacctggcgt ggagtacctt gtcagcatca    5700
tcgccatgaa gggctttgag gaaagtgaac ctgtctcagg gtcattcacc acagctctgg    5760
atggcccatc tggcctggtg acagccaaca tcactgactc agaagccttg gccaggtggc    5820
agccagccat tgccactgtg gacagttatg tcatctccta cacaggcgag aaagtgccag    5880
aaattacacg cacggtgtcc gggaacacag tggagtatgc tctgaccgac ctcgagcctg    5940
ccacggaata cacactgaga atctttgcag agaaagggcc ccagaagagc tcaaccatca    6000
ctgccaagtt cacaacagac ctcgattctc aagagactt gactgctact gaggttcagt     6060
cggaaactgc cctccttacc tggcgacccc cccgggcatc agtcaccggt tacctgctgg    6120
tctatgaatc agtggatggc acagtcaagg aagtcattgt gggtccagat accacctcct    6180
acagcctggc agacctgagc ccatccaccc actacacagc caagatccag gcactcaatg    6240
ggccctgag gagcaatatg atccagacca tcttcaccac aattggactc ctgtacccct     6300
tccccaagga ctgctcccaa gcaatgctga atggagacac gacctctggc ctctacacca    6360
tttatctgaa tggtgataag gctgaggcgc tggaagtctt ctgtgacatg acctctgatg    6420
ggggtggatg gattgtgttc ctgagacgca aaaacgacg cgagaacttc taccaaaact     6480
ggaaggcata tgctgctgga tttggggacc gcagagaaga attctggctt gggctggaca    6540
acctgaacaa aatcacagcc caggggcagt acgagtccg ggtggacctg cgggaccatg     6600
gggagacagc ctttgctgtc tatgacaagt tcagcgtggg agatgccaag actcgctaca    6660
agctgaaggt ggaggggtac agtgggacag caggtgactc catggcctac cacaatggca    6720
gatccttctc caccttgac aaggacacag attcagccat caccaactgt gctctgtcct     6780
acaaaggggc tttctggtac aggaactgtc accgtgtcaa cctgatgggg agatatgggg    6840
acaataacca cagtcagggc gttaactggt tccactggaa gggccacgaa cactcaatcc    6900
agtttgctga tgatgaagctg agaccaagca acttcagaaa tcttgaaggc aggcgcaaac    6960
gggcataaat tccagggacc actgggtgag agaggaataa ggcccagagc gaggaaagga    7020
ttttaccaaa gcatcaatac aaccagccca accatcggtc cacacctggg catttggtga    7080
gagtcaaagc tgaccatgga tccctgggc caacggcaac agcatgggcc tcacctcctc     7140
tgtgattct tcttcgcac caaagacatc agtctccaac atgtttctgt tttgttgttt      7200
gattcagcaa aaatctccca gtgacaacat cgcaatagtt ttttacttct cttaggtggc    7260
tctgggaatg ggagagggt aggatgtaca ggggtagttt gttttagaac cagccgtatt     7320
ttacatgaag ctgtataatt aattgtcatt attttgtta gcaaagatta aatgtgtcat     7380
tggaagccat ccctttttt acatttcata caacagaaac cagaaaagca atactgtttc    7440
catttaagg atatgattaa tattattaat ataataatga tgatgatgat gatgaaaact     7500
aaggattttt caagagatct ttctttccaa aacatttctg gacagtacct gattgtatt     7560
tttttttaaa taaaagcaca agtactttg agtttgttaa aaaaaaaaa aaaaaa          7616
```

<210> SEQ ID NO 70
<211> LENGTH: 222
<212> TYPE: PRT
<213> ORGANISM: Homo sapiens

<400> SEQUENCE: 70

```
Pro Phe Pro Lys Asp Cys Ser Gln Ala Met Leu Asn Gly Asp Thr Thr
1               5                   10                  15
```

```
Ser Gly Leu Tyr Thr Ile Tyr Leu Asn Gly Asp Lys Ala Glu Ala Leu
            20              25              30

Glu Val Phe Cys Asp Met Thr Ser Asp Gly Gly Trp Ile Val Phe
        35              40              45

Leu Arg Arg Lys Asn Gly Arg Glu Asn Phe Tyr Gln Asn Trp Lys Ala
    50              55              60

Tyr Ala Ala Gly Phe Gly Asp Arg Arg Glu Glu Phe Trp Leu Gly Leu
65              70              75              80

Asp Asn Leu Asn Lys Ile Thr Ala Gln Gly Gln Tyr Glu Leu Arg Val
            85              90              95

Asp Leu Arg Asp His Gly Glu Thr Ala Phe Ala Val Tyr Asp Lys Phe
            100             105             110

Ser Val Gly Asp Ala Lys Thr Arg Tyr Lys Leu Lys Val Glu Gly Tyr
            115             120             125

Ser Gly Thr Ala Gly Asp Ser Met Ala Tyr His Asn Gly Arg Ser Phe
    130             135             140

Ser Thr Phe Asp Lys Asp Thr Asp Ser Ala Ile Thr Asn Cys Ala Leu
145             150             155             160

Ser Tyr Lys Gly Ala Phe Trp Tyr Arg Asn Cys His Arg Val Asn Leu
            165             170             175

Met Gly Arg Tyr Gly Asp Asn Asn His Ser Gln Gly Val Asn Trp Phe
            180             185             190

His Trp Lys Gly His Glu His Ser Ile Gln Phe Ala Glu Met Lys Leu
            195             200             205

Arg Pro Ser Asn Phe Arg Asn Leu Glu Gly Arg Arg Lys Arg
    210             215             220
```